(12) United States Patent
Daily et al.

(10) Patent No.: US 6,530,900 B1
(45) Date of Patent: Mar. 11, 2003

(54) DRUG DELIVERY DEVICE

(75) Inventors: David Daily, Herzliya (IL); Oz Cabiri, Macabim (IL); Mario Rozanowich, Ezer (IL); Miki Sahar, Ramat Hasharon (IL); Jacob Stern, Shoam (IL); Diana Davidson, Framingham, MA (US); Izrail Tsals, Sudbury, MA (US); Gilad Lavi, Holon (IL); Avi Azoulay, Ashdod (IL); Eran Shor, Moshav Bitzaron (IL); Craig Brodeur, Marlborough, MA (US)

(73) Assignee: Elan Pharma International Limited, Shannon (IL)

( * ) Notice: Subject to any disclaimer, the term of this patent is extended or adjusted under 35 U.S.C. 154(b) by 0 days.

(21) Appl. No.: 09/577,033

(22) Filed: May 23, 2000

Related U.S. Application Data

(63) Continuation-in-part of application No. 09/072,875, filed on May 5, 1998.
(60) Provisional application No. 60/045,745, filed on May 6, 1997.

(51) Int. Cl.[7] .............................................. A61M 37/00
(52) U.S. Cl. ...................... 604/132; 604/891.1; 604/141
(58) Field of Search ................................. 604/132, 141, 604/148, 145, 146, 246–249, 167.01–167.05, 19, 48, 65, 93.01, 131, 133, 140, 173, 174, 180, 890.1, 891.1

(56) References Cited

U.S. PATENT DOCUMENTS 4,684,367 A   8/1987   Schaffer et al.
4,708,716 A * 11/1987  Sibalis ...................... 604/20
5,588,556 A  12/1996   Sancoff et al.
5,779,676 A   7/1998   Kriesel et al.
5,814,020 A   9/1998   Gross

FOREIGN PATENT DOCUMENTS

| WO | WO 95/13838   | 5/1995 |
|----|---------------|--------|
| WO | WO 97/10012   | 3/1997 |
| WO | WO 99/62576 A1 | 12/1999 |

* cited by examiner

Primary Examiner—Manuel Mendez
Assistant Examiner—Mark Han
(74) Attorney, Agent, or Firm—Caesar, Rivise, Bernstein, Cohen & Pokotilow, Ltd.

(57) ABSTRACT

A drug delivery device having a housing having an internal reservoir in communication with a drug delivery outlet via a fluid path. An expandable chamber disposed adjacent to the reservoir forces drug from the reservoir to the outlet when supplied with a gas. A flow regulating chamber, in communication with the fluid path, is capable of volumetric changes in response to temperature and/or pressure changes. An increase in the volume of the flow regulating chamber increases flow resistance to the outlet and thereby counteracts the corresponding increase in delivery rate resulting from the expansion of the expandable chamber due to the same volumetric changes in response to temperature and/or pressure. In a preferred embodiment, an electrical circuit has a current stabilizing element in electrical communication with an electrolytic cell which supplies the gas. A throttling device maintains a higher pressure in the device to reduce possible clogging of the fluid path. In a preferred embodiment, the drug delivery device is packaged to insulate the device from atmospheric pressure and humidity.

11 Claims, 48 Drawing Sheets

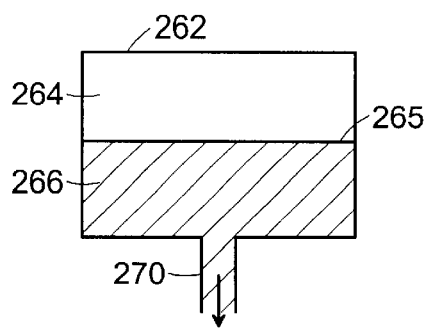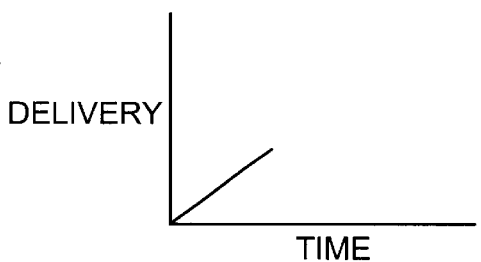
FIG. 33A     FIG. 33B
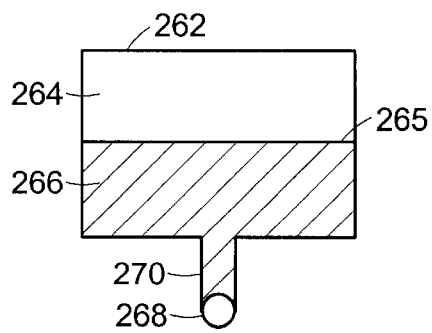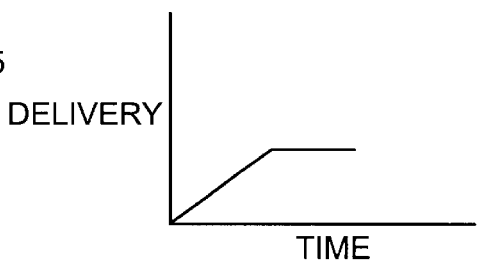
FIG. 33C     FIG. 33D
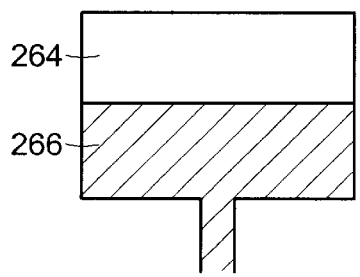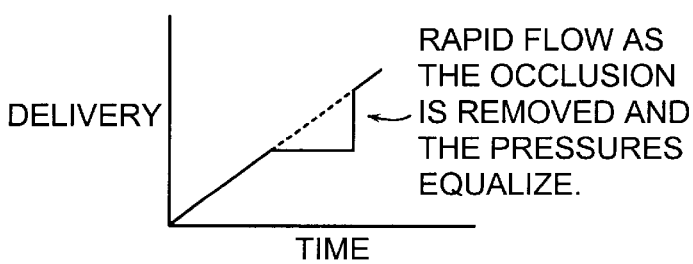
FIG. 33E     FIG. 33F

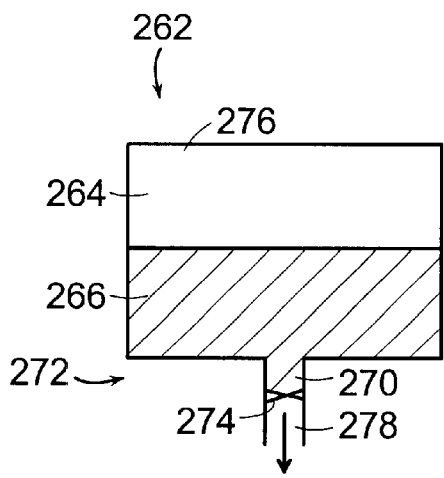 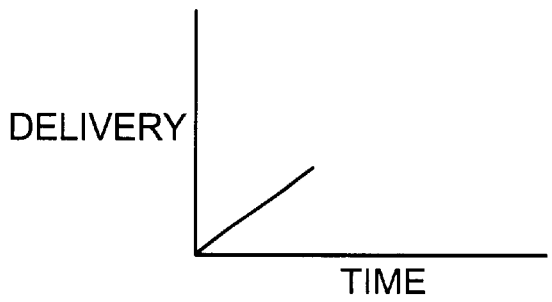
FIG. 34A  FIG. 34B
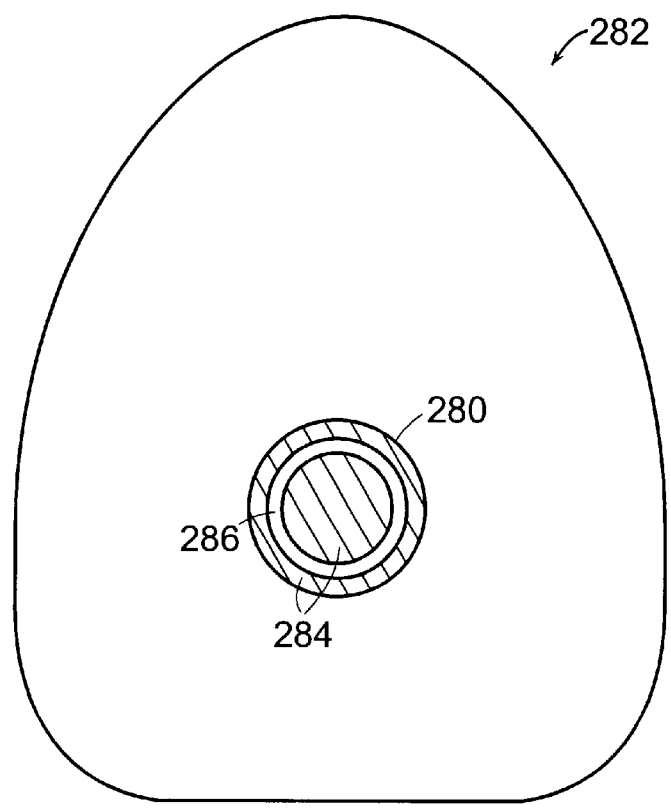
FIG. 35

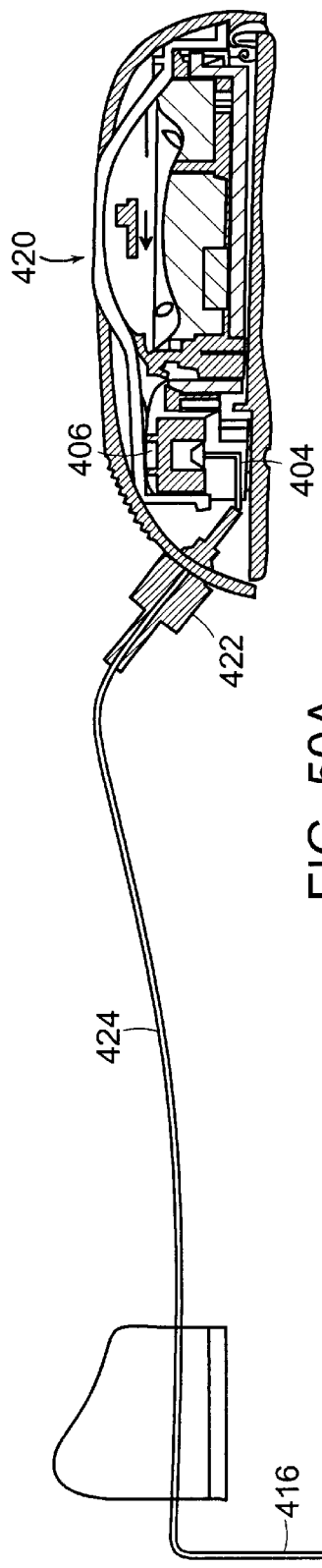
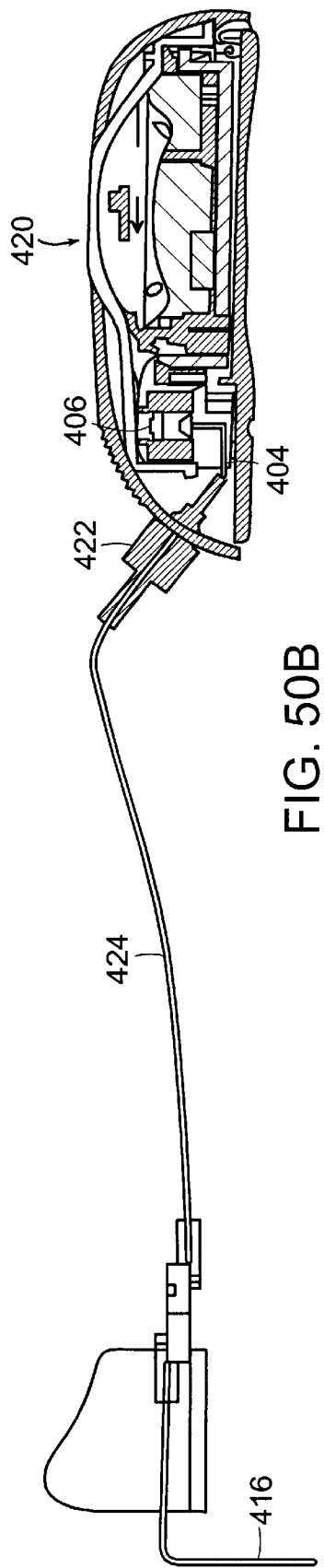
FIG. 50A
FIG. 50B

DRUG DELIVERY DEVICE

RELATED APPLICATION(S)

This application is a continuation-in-part of U.S. Ser. No. 09/072,875 filed on May 5, 1998 which claims priority to U.S. Provisional Application No. 60/045,745 filed May 6, 1997, the entire teachings of both of which are incorporated herein by reference.

BACKGROUND OF THE INVENTION

A wide range of subcutaneous drug delivery devices are known in which a drug is stored in an expandable-contractible reservoir. In such devices, the drug is delivered from the reservoir by forcing the reservoir to contract. (The term "subcutaneous" as used herein includes subcutaneous, intradermal and intravenous.)

Such devices can be filled in the factory or can be filled by the pharmacist, physician or patient immediately prior to use. In the former case it may be difficult to provide the required drug stability in the device since the drug will be stored in the reservoir for a shelf life of from several months to a number of years. In the latter case, it is difficult to ensure that the drug has completely filled the reservoir, i.e. that the reservoir and fluid path do not contain any air bubbles. In general, this requires priming the device by filling it in a certain orientation which ensures that the air bubbles are pushed ahead of the drug, such as with the filling inlet at the bottom and the delivery outlet at the top (to allow the bubbles of air to rise during filling).

A further problem associated with subcutaneous drug delivery devices is that in many cases gas generation is used to compress the reservoir. While it may be possible to ensure a constant or a controllably varying rate of gas generation (for example by passing a constant current through an electrolytic cell), this does not ensure a constant rate of drug delivery.

The amount of compression of the reservoir (and thus the rate of delivery of drug) depends on the amount by which the volume of the gas generation chamber expands. The behavior of an ideal gas is governed by the equation $PV=nRT$, in which the volume of gas, V, is proportional to the number of moles of gas, n, and the temperature, T, and inversely proportional to the pressure, P.

An electrolytic cell working at constant current will generate a constant number of moles of gas per unit time. However, changes in the temperature of the gas and in the atmospheric pressure exerted on the gas will cause the volume to vary. Even if the temperature of the device remains constant, the fact that atmospheric pressure drops by approximately 3% for every increase in altitude of 300 m means that the delivery rate will vary substantially between a location at sea level and a higher altitude location (for example, Denver, Colo. is approximately 1 mile or 1.6 kilometers above sea level, so atmospheric pressure will be approximately 17% lower on average than at sea level). Similarly, normal changes in atmospheric pressure due to the weather cause the delivery rate of this type of device to vary.

For devices which employ a needle to penetrate the skin there is a danger that after use the device may accidentally infect the patient or others if not properly disposed of. WO 95/13838 discloses an intradermal device of this type having a displaceable cover which is moved between a first position in which the needle is retracted before use and a second position in which the needle is exposed during use. Removal of the device from the skin causes the cover to return to the first position in which the needle is again retracted before disposal. However, this device does not include a locking mechanism in the assembly for locking the device prior to use to minimize accidental contact with the needle and/or accidental actuation of the device that may occur during shipping and/or storage.

When filling a drug delivery device, the conventional method is to use a syringe, which carries the risk of accidental injury. The present invention has as a further aim the improvement of safety when syringes are used. The present invention also aims to decrease the possibilities that the needle could become exposed by accident before or after use, for example, by a child playing with the device if not properly disposed of. Clearly given the risks associated with infectious diseases, particularly those carried by blood, any possibility of accidental infection must be minimized to the utmost and preferably eliminated entirely.

Our International Application No. PCT/IE 96/00059 discloses a medicament delivery device having a filling mechanism integral within the housing which receives a cylindrical cartridge (or "vial") sealed by a sliding stopper. When the cartridge is pushed into the filling mechanism, a hollow needle in the filling mechanism penetrates the stopper and establishes communication between the interior of the cartridge and the device's internal reservoir. Continued movement of the cartridge into the filling mechanism causes the stopper to slide into the cartridge and act as a piston to pump the medicament from the cartridge into the reservoir. While this mechanism overcomes some of the disadvantages of using a syringe, it also makes the device bulkier.

Thus, there is a need to provide a subcutaneous drug delivery device having an improved filling mechanism which facilitates filling the device in an orientation-independent manner.

There is a further need to provide a filling system that is less bulky.

There is still a further need to provide a filling system that maintains the needles within the system in a recessed fashion so as to minimize the risk of injury associated with needles.

There is yet a further need to provide a device which operates at a substantially constant delivery rate independently of the ambient atmospheric pressure.

There is a further need to provide a drug delivery device in which the needle is retracted from the housing surface before and after use so as to minimize injury due to accidental contact with the needle.

There is yet a further need to provide a device having improved adhesion to the skin, i.e. for which there is less likelihood that the device will become detached during use.

SUMMARY OF THE INVENTION

The present invention overcomes these and other disadvantages associated with prior art drug delivery devices and filling systems. Stated generally, the present invention provides for a drug delivery device having a housing that has an internal reservoir and an expandable chamber disposed relative to the reservoir. The device also has a drug delivery needle extending from the housing for penetration of the skin of a subject. The needle has an outlet for drug delivery. The drug delivery device of the present invention further includes a fluid path defined between the delivery needle outlet and the reservoir and means for providing a gas at a controllable rate into the expandable chamber. The device also includes a flow regulating chamber, in communication with the fluid path, which is capable of volumetric changes in response to temperature and/or pressure changes.

By calibrating the degree of increase or decrease in flow resistance, it is possible to compensate for differences occurring in the rate of delivery which arise because of pressure- or temperature-induced differences in the volume of a given mass of gas in the expandable chamber. Thus, if the ambient atmospheric pressure drops, the gas in the expandable chamber will tend to expand and thereby force more drug from the reservoir. This will however be counteracted by the flow regulating chamber which will increase flow resistance along the fluid path and thereby counteract the increased flow rate arising from the effect of the tendency for the expandable chamber to expand.

Preferably, the expandable chamber causes contraction of the reservoir in use. Further, preferably, the flow regulating chamber alters the drug delivery rate by varying the flow resistance between the reservoir and the outlet. Preferably, the flow regulating chamber is associated with a blocking member which upon expansion of the flow regulating chamber moves within the fluid path so as to restrict the flow of drug.

Further, preferably, the blocking member comprises a formation provided on a displaceable member which at least partially bounds the flow regulating chamber, the formation being disposed adjacent to an inlet of a conduit forming part of the fluid path, such that restriction of the fluid path occurs when the blocking member is moved into the inlet of the conduit. By having a suitably shaped and sized formation relative to the inlet, it is possible to precisely vary the flow resistance of the conduit, and thereby precisely control the delivery rate notwithstanding changes in ambient temperature and/or pressure.

Suitably, the shape of the blocking member is adapted to cut off the fluid path completely with a predetermined degree of expansion of the flow regulating chamber. Alternatively, the formation can be shaped such that the fluid path is never entirely cut off.

In preferred embodiments of the invention, a displaceable cover is connected to the housing such that displacement of the housing relative to the cover when the cover has been applied to the skin of a subject causes the delivery needle to penetrate the skin of the subject. Such a displaceable cover is suitable for concealing the needle before and after application to the skin of a subject, which prevents injury and reduces the possibility of contamination of the needle.

In another aspect of the invention the expandable chamber is provided with a release valve operatively connected to the displaceable cover such that the movement of the housing relative to the cover controls the closing of the valve and thereby the sealing of the expandable chamber. This feature is not dependent on the existence of the flow regulating chamber.

The valve enables the device to be supplied with the displaceable member positioned such that the volume of the (empty) reservoir is minimized and that of the expandable chamber maximized. Thus, the reservoir can be of substantially zero volume initially, with no entrapped air volume. The device can then be primed or loaded by filling the reservoir, for example using a syringe- or cartridge-based filling mechanism. As the reservoir is filled, the displaceable member moves to expand the reservoir and thereby contract the expandable chamber. The valve allows the air or other gas in the expandable chamber to be exhausted into the atmosphere.

The device can then be applied to the skin of the user. When the device is applied the housing moves relative to the cover which is applied to the skin, not only does the needle penetrate the skin, but also (because the valve is operatively connected to the cover) the valve is closed to seal the expandable chamber. If the valve remained open then gas supplied into the expandable chamber would be free to escape and delivery would not be effected. While it would be possible for the user to close the valve manually, this would clearly leave open the possibility of error. Instead, by connecting the valve operatively to the cover, it is possible to ensure that the valve is always closed when the device is applied to the skin.

Preferably the valve comprises two components one of which is connected to the cover and the other of which is connected to the expandable chamber, such that relative movement of the housing towards the cover causes the valve to close.

The invention includes a displaceable cover that is displaceable relative to the housing between a first position in which the needle is concealed from the exterior of the device, and a second position in which the delivery needle protrudes from the device for penetration of the skin. A further aspect of the present invention comprises means for locking the device in the first position after a single reciprocation of the device from the first position to the second position and back to the first position.

The displaceable cover is an advantageous feature since it solves a problem unaddressed by prior art devices. Our prior art device has a locking mechanism to lock the housing in place after use and keep the needle concealed. However, there is no mechanism to prevent premature activation prior to intended use that may cause the needle to protrude accidentally thereby giving rise to injury. According to the present invention, however, the locking means engages automatically when the cover and housing are reciprocated relative to one another, i.e. the housing and cover are moved relative to one another to cause the needle to protrude when the device is applied to the skin. This relative movement is reversed when the device is removed thereby concealing the needle but also engaging the locking means to prevent the needle from being exposed again by accident.

In a preferred embodiment, the locking means comprises a mechanical latch which is brought into operation by the reciprocation. Further, it is preferred that the latch comprises a pair of elements mounted on the cover and the housing respectively. It is preferred that the elements be shaped such that they can have two relative configurations when the cover is in the first position relative to the housing. It is preferred the elements have a first movable configuration in which the elements are mutually movable, and a second locked configuration in which the elements are prevented from mutual movement. It is also preferred that the reciprocation of the cover and the housing causes the elements to pass from the first movable configuration, through an intermediate configuration when the cover is in the second position relative to the housing, and then to the second locked configuration, thereby preventing any further movement of the cover relative to the housing.

In preferred embodiments illustrated further below, one of the elements is provided with a recess which is adapted to receive a projection on the other of the elements, the recess and the projection being spaced apart from one another in the movable configuration, and being in engagement with one another in the locked configuration.

These embodiments are preferred because while they are mechanically simple and easy to make, their very simplicity provides fewer opportunities for malfunction.

In a preferred embodiment of the present invention, movement of the cover relative to the housing is initially prevented by a removable locking member. This feature helps to prevent accidental injury occurring because the needle is only exposed when the housing is moved relative to the cover, i.e. only after the user has specifically removed the removable locking member. The presence of the removable locking member also prevents the means for providing a gas from being actuated. This prevents the device from being exhausted by accidental switching on at an incorrect time. In a preferred embodiment of the present invention, the removable locking member comprises a laminar member inserted between the cover and the housing.

In a further aspect of the invention, the surface of the housing from which the needle extends or the surface of the displaceable cover, if present, is of a concave cross-section. When the device has been applied to the skin of a subject, removal of the device is resisted because the cover conforms more closely to the skin. In prior art devices, it has been found that retention on the skin of the user is problematic because of adhesive failure, for example. Using a concave surface causes the device to be retained more effectively by adhesive means.

With prior art devices the lower surface tends to be peeled away from the skin more easily as the edges of the device can be detached relatively easily. Where a concave lower surface is used the edges tend to remain in contact with the skin and removing the device is thus more difficult. In effect a shear force is required rather than a simple peeling, and this assists in preventing accidental removal. This feature is not dependent on the existence of the other aspects of the invention.

In a modified device according to the invention, the needle extends from the lower surface of the housing is replaced by a tube extending from the housing. The tube is adapted for carrying a drug delivery needle. Such a device is preferred for intravenous delivery of a drug as the needle carried on the end of the tube can be accurately located in a suitable vein. The needle may be integral with the tube or supplied separately.

In a further preferred feature of the present invention, the drug reservoir is separated from the expandable chamber by a diaphragm. The diaphragm exhibits bistable behavior such that in one stable state the reservoir is full and in the other stable state the reservoir is empty. The diaphragm is shaped to minimize the energy required in the transition between the stable states. In a preferred embodiment of the present invention, the diaphragm is in the form of a body having a peripheral lip connected to a substantially flat central section by a flexible annular section. The flexible annular section assumes a substantially frusta-conical cross-section in one of the states and assuming an arcuate curved cross-section in the other state.

Preferably, the means for providing a gas comprises an electrical circuit in which any transistors are bipolar transistors having a gain of not less than 500, such that the circuit can be irradiated by ionizing radiation without destroying the circuit.

This type of transistor has been found to be advantageous as it enables the device to be sterilized using gamma radiation with the electronic components intact. While a certain loss of performance results from the irradiation, the high gain transistor still has an adequate gain after irradiation to operate reliably. It is preferred that the current gain of the or each transistor is not less than 750. For example, a transistor having a rated current gain of 800 has been found to give an excellent performance after irradiation, despite the fact that irradiation lowers the current gain characteristics of the transistor by a factor of ten or more. The initial high gain compensates for the subsequent reduction arising from irradiation. The fact that the effects of irradiation can be predicted means that the performance after irradiation is reliable.

It is also preferred that the circuit further include a reference component across which a fixed potential drop is measurable. The reference component is essentially unchanged by the ionizing radiation. If a reference voltage is used which is not affected by the irradiation process, then the operation of the other components in the circuit may be determined by this reference voltage. For example, while the current gain of a group of transistors may vary individually when a batch is irradiated, each such transistor can be used to make an identically functioning amplifier if the output current of the amplifier is matched against a given reference component.

Light emitting diodes (LEDs) have been found to be affected less than other standard components when irradiated by gamma radiation. Thus, the reference component of the preferred embodiment comprises a light-emitting diode. Gallium arsenide (GaAs) LEDs are virtually unaffected by gamma rays. Thus, it is preferred that the light emitting diode employs gallium arsenide as a semiconductor.

In a further aspect, the present invention provides for a subcutaneous drug delivery kit including a drug delivery device as described above. The device is provided with a filling mechanism associated with the reservoir. The filling mechanism includes means for receiving a filling adapter. The filling adapter includes a body which is adapted to accommodate a drug cartridge. The body has means for engaging the adapter-receiving means of the drug delivery device at one end thereof, means for receiving a cartridge at the other end thereof, and transfer means for transferring a liquid from a cartridge to the filling mechanism of the device as the cartridge is emptied. The adapter-receiving means and the corresponding engaging means provided on the adapter together constitute a releasable locking mechanism which holds the adapter in place on the device once engaged. The locking mechanism is disengaged by the cartridge when the cartridge is emptied within the adapter.

The kit according to the invention is advantageous because it eliminates the need for a bulky filling mechanism which accommodates the cartridge within the device, and instead employs an adapter which is releasable from the device so as to enable the filled device to be less bulky than prior art cartridge-based devices.

Furthermore, the locking mechanism employed is only disengaged when the cartridge has been completely emptied, i.e., the rubber stopper within the cartridge is pushed to the bottom. If the cartridge used is of a type which will empty when the stopper is pushed to the bottom, this feature ensures accurate loading of the reservoir, i.e. it is not possible to easily remove the device before the reservoir is filled with the correct dose of medicament.

Suitably, the transfer means comprises a hollow double-ended needle, one end of which is associated with the engaging means such that it communicates with the filling mechanism when the adapter is engaged with the device, and the other end of which is associated with the cartridge receiving means such that it communicates with the interior of a cartridge having a penetrable stopper when such a cartridge is received by the adapter.

Such a hollow double ended needle can be replaced by a pair of needles which are connected by a conduit, such as a moulded conduit running through the body of the adapter and having a needle mounted at either end such that it is functionally equivalent to a double ended needle. Preferably, both ends of the needle are disposed within the body of the adapter such that they are recessed from the exterior of the body when the adapter is disengaged from the device. This arrangement is preferable for safety reasons, as it allows the adapter to be disposed of without fear of accidental injury occurring from casual handling of the adapter.

In a preferred embodiment, the releasable locking mechanism comprises a pair of locking members provided on the adapter receiving means and the corresponding engaging means, respectively. One of the locking members is movable between a locking position and a disengaging position. The movable locking member is disposed relative to the body such that, in use, when a cartridge is emptied within the body, the movable locking member is moved from the locking position to the disengaging position under the action of the cartridge.

Where a substantially cylindrical cartridge is employed, the body can receive the cartridge within a passage having a diameter sufficient to completely accommodate the cartridge. However, the end of the passage is of slightly narrower diameter on account of a projection provided on the movable locking member. Thus, when the cartridge completely emptied by pushing the stopper to the bottom, it contacts the movable locking member and pushes it out of the way, thereby disengaging the locking mechanism.

Suitably, the movable locking member is resiliently biased towards the locking position. Preferably, the movable locking member is a latch which automatically locks the adapter and device to one another when engaged together. It is preferred that the cartridge is emptied by moving the penetrable stopper against the adapter The present invention further provides a subcutaneous drug delivery kit including a device according to any preceding claim further comprising a filling mechanism associated with the reservoir, the filling mechanism comprising means for receiving a filling adapter as defined herein and a filling adapter. The filling adapter has a body adapted to receive a syringe. The body has means for engagement with the adapter-receiving means of the device at one end thereof, syringe-receiving means at the other end thereof and transfer means for transferring a liquid from the syringe to the filling mechanism of the device as the syringe is emptied. The transfer means includes a conduit associated with the syringe receiving means, the conduit leads to a needle which is associated with the engagement means and is disposed within the body of the filling adapter.

It is preferred that the needle disposed within the body of the filling adapter is recessed from the exterior of the body when the adapter is disengaged from the device. It is also preferred that the adapter receive the syringe without a needle. Since the needle on the adapter is recessed from the exterior of the adapter body and the syringe has no needle when filling, a conventional syringe (minus needle) can be used to fill the device without any risk of accidental injury.

A further aspect of the present invention provides a method of filling a drug delivery device. The method includes providing a drug delivery device having a drug reservoir. The reservoir is associated with a filling mechanism having filling adapter receiving means. The method further includes providing a filling adapter having a first end for engagement with the adapter receiving means, and a second end for receiving a syringe and causing the filling adapter receiving means to receive the filling adapter. The method further includes causing the second end of the filling adapter to receive a syringe having liquid stored therein and a needle, and providing a conduit for communication between the liquid stored within the syringe and the first end of the filling adapter. The method of filling further includes emptying the syringe and concurrently transferring the liquid from the syringe to the device via the conduit. In yet further aspects, the invention provides a filling adapter as defined above and a diaphragm as defined above.

In a preferred embodiment of the present invention, the electrical circuit used to provide gas to the expandable chamber includes a high voltage supply, such as, for example, between one and three batteries and current stabilizing elements, such as, for example, two resistors connected in series. The electrical circuit of this preferred embodiment simplifies the electrical circuit and stabilizes the current supplied to the electrolytic cell without using components such as transistors which are sensitive to gamma radiation used for sterilization.

Another aspect of a preferred embodiment of the drug delivery system of the present invention includes an occlusion prevention mechanism. Further, it is not desirable that the delivery rate of the drug delivery device be altitude dependent. An element, such as, for example, a valve in the drug delivery device, creates a constant high, back pressure within the gas chamber, minimizing or preferably preventing the formation of boli of drugs.

In a preferred embodiment of the present invention, an optical window, such as, for example, a ring like structure, provides a more accurate assessment of the quantity of drug delivered or alternatively, the quantity of drug remaining in the drug reservoir. The embodiment makes use of the principle of light reflected from the elastomeric membrane or diaphragm containing the drug. When the drug reservoir is approximately full, the optical window appears black as the elastomeric membrane is extended away from the housing as the drug fills it. However, when the drug reservoir is approximately empty, the optical window appears blue in color, for example, as the elastomeric membrane is proximate to the housing as drug delivery is close to completion.

Further, in a preferred embodiment, the subcutaneous drug delivery device includes a pressure sensitive mechanism for preventing a rapid injection of a drug to a user. For example, the pressure sensitive mechanism can include a switch that forms a part of the electrical circuit which controls the power supply to a gas generating portion of the drug delivery device. The switch can include different preferred components to complete the circuit, such as one including a conductive membrane and a conductive lever, or alternatively, electrodes and a droplet of mercury. The electrical circuit is completed as long as the pressure in the gas generating portion is less than the pressure within a chamber.

In another preferred embodiment, the drug delivery system in accordance with the present invention includes a visual indicator to indicate proper application and operation to a user. The indicator can be, for example, a color marking system. The color marking system can be used to indicate to a user components of the system which should be removed from the system prior to use.

Another preferred embodiment of the drug delivery system of the present invention includes an insert, for example, a foam insert that receives the internal components of the device and accommodates design tolerances. The insert maintains an accurate internal volume so that upon assembly, the volume of the internal housing, and thus the drug reservoir, is within an accurate range.

In a preferred embodiment, the drug delivery system of the present invention includes an activation mechanism, such as, for example, an activation lever to initiate gas generation in the expandable chamber which in turn controls the delivery of the drug from the device. The activation mechanism also includes a puncturing device and an electrical contact. In operation, upon depression, the puncturing device punctures the foil cover of the electrolytic cell, thereby allowing the chemical ingredients to release gas for expanding the expandable chamber. As a result, the proximate drug reservoir is compressed and drug delivery is initiated.

Another preferred embodiment of the drug delivery system relates to controlling the rate of delivery which is controlled by several parameters. The parameters include, but are not limited to, circuit current, residual air volume, material permeability, material properties of plastic material in device, and membrane seal. For example, the permeability of the drug delivery system components, such as the permeability of the materials used in the base affects the delivery rate of the drugs delivered. thus, materials such as, for example, PET that minimizes or preferably prevents the permeation of the gases generated in the device, for example, hydrogen is used. By minimizing the permeability of the gases of the expandable chamber, a constant delivery rate can be maintained. As the diffusion rate of the gases controls the delivery rate of the drug, material changes can control the delivery rate of drugs.

Another aspect of the present invention includes packaging of the drug delivery system to insulate the system from storage and use in different altitudes. In particular, the electrolyte in the electrolytic cell used to generate gas in the expandable chamber is affected by environmental conditions. Further, the performance of the barometric pressure valve can be affected by the environmental conditions as it relies on a reference pressure of a fixed amount of the air. At high altitudes, air from the reference cell can diffuse out of the device due to expansion of the air. In a preferred embodiment, by hermetically packaging the device, the barometric pressure valve has only one position, that is, it is a stationary valve as the pressure inside the device is constant.

Thus, it is an object of the present invention to provide a subcutaneous drug delivery device having an improved filling mechanism which facilitates filling the device in an orientation-independent manner.

It is a further object of the present invention to provide a filling system that is less bulky.

It is still a further object of the present invention to provide a filling system that maintains the needles within the system in a recessed fashion so as to minimize the risk of injury associated with needles.

It is yet a further object of the present invention to provide a device which operates at a substantially constant delivery rate independently of the ambient atmospheric pressure.

It is even yet a further object of the present invention to provide a drug delivery device in which the needle is retracted from the housing surface before and after use so as to minimize injury due to accidental contact with the needle.

It is yet a further object of the present invention to provide a device having improved adhesion to the skin, i.e. for which there is less likelihood that the device will become detached during use.

Other objects, features and advantages of the present invention will be apparent upon reading the following specification taken in conjunction with the drawings and appended claims.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 33A–33F illustrate both schematically and graphically, an embodiment of a drug delivery device which can be compromised by an occlusion;

FIGS. 34A and 34B schematically and graphically illustrate a preferred embodiment of a drug delivery device having an occlusion prevention mechanism in accordance with the present invention;

FIG. 35 schematically illustrates a preferred embodiment of the drug delivery device in accordance with the present invention;

FIG. 50A is a sectional side view of the alternative embodiment of the drug delivery device of FIG. 48 with the luer connection on to be an epidural needle; and FIG. 50B is a sectional side view of the alternative embodiment of the drug delivery device of FIG. 48 with the luer connection to an epidural needle with a hydrophobic membrane and a hydrofoil membrane.

DETAILED DESCRIPTION OF THE INVENTION

Figure 1:
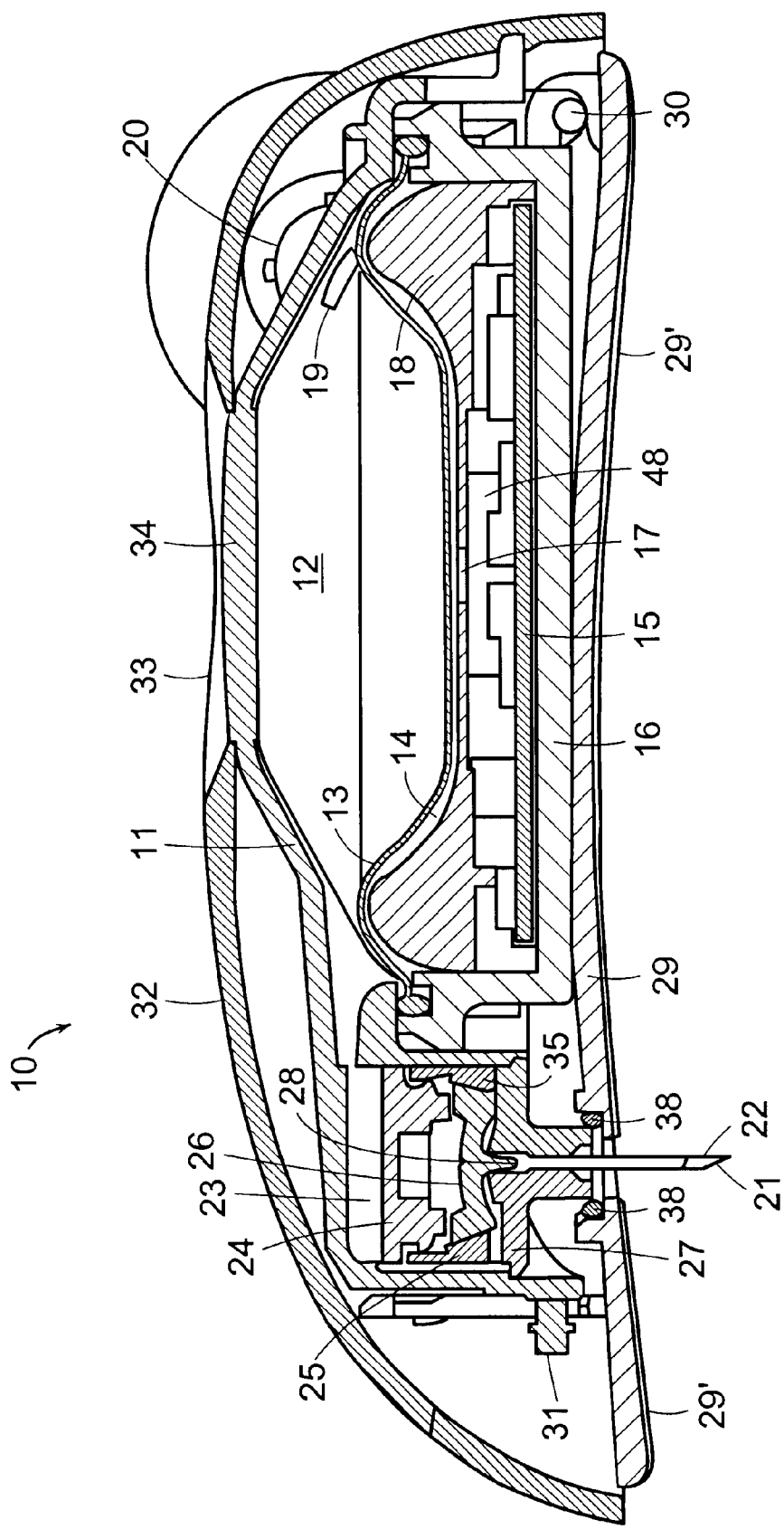
FIG. 1 is a sectional side view of a first embodiment of drug delivery device according to the present invention.

Referring now in more detail to the drawings, in which like numerals refer to like parts throughout the several view, FIG. 1 indicates a subcutaneous drug delivery device 10 according to the invention.

A housing 11 defines a reservoir 12 which is partially bounded by an elastomeric diaphragm 13 which allows the reservoir to expand and contract. The diaphragm 13 also bounds an expandable chamber 14 such that expansion of the expandable chamber causes the reservoir 12 to contract and vice versa. In FIG. 1, the reservoir 12 is at full volume and contains a drug, while the expandable chamber 14 is at minimum volume.

A circuit board 15 having an electrolytic cell 48 mounted thereon (explained in greater detail below) is mounted in the lower part 16 of the housing 11. In use, the electrolytic cell 48 feeds a gas into the expandable chamber 14 via an aperture 17 in a supporting member 18.

The reservoir 12 is provided with an inlet 19 which is in communication with a filling mechanism 20 (explained in greater detail below). A delivery needle 21 provided with an outlet 22 is in communication with the reservoir 12 via a fluid path 23 which is indicated by arrows. The fluid path 23 passes around an air-filled flow-regulating chamber 35 which comprises a top member 24, annular member 25 and flow diaphragm 26. The fluid path 23 also passes via a needle holder 27 to the needle 21. The inlet 19 to the needle 21 is partially restricted by a projection 28 on the flow diaphragm 26, such that any upward movement of the projection 28 reduces resistance to flow and any downward movement of the projection increases flow resistance.

Figure 2:
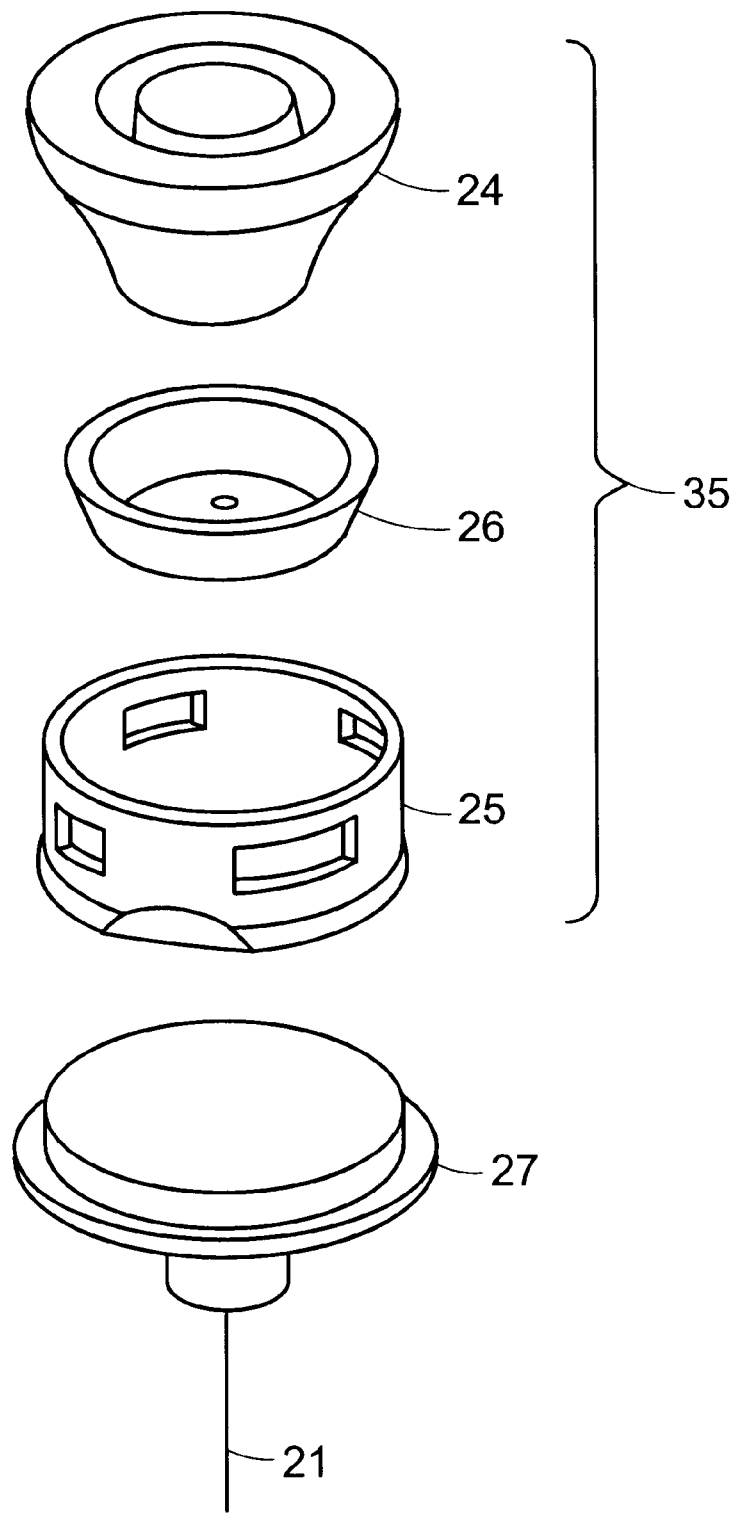
FIG. 2 is an exploded perspective view of the flow regulating chamber and needle assembly of the first embodiment of the device of FIG. 1.

Referring additionally to FIG. 2, the flow regulating chamber 35 can be seen in exploded view. Annular member 25 receives the flow diaphragm 26, and top member 24 and the three components fit together to form an airtight chamber 36 which is positioned above the needle holder 27. The inlet 19 in the needle holder 27 leading to the needle 21 can be clearly seen on the top surface of the needle holder. Projection 28 extends into the inlet 19.

Figure 4:
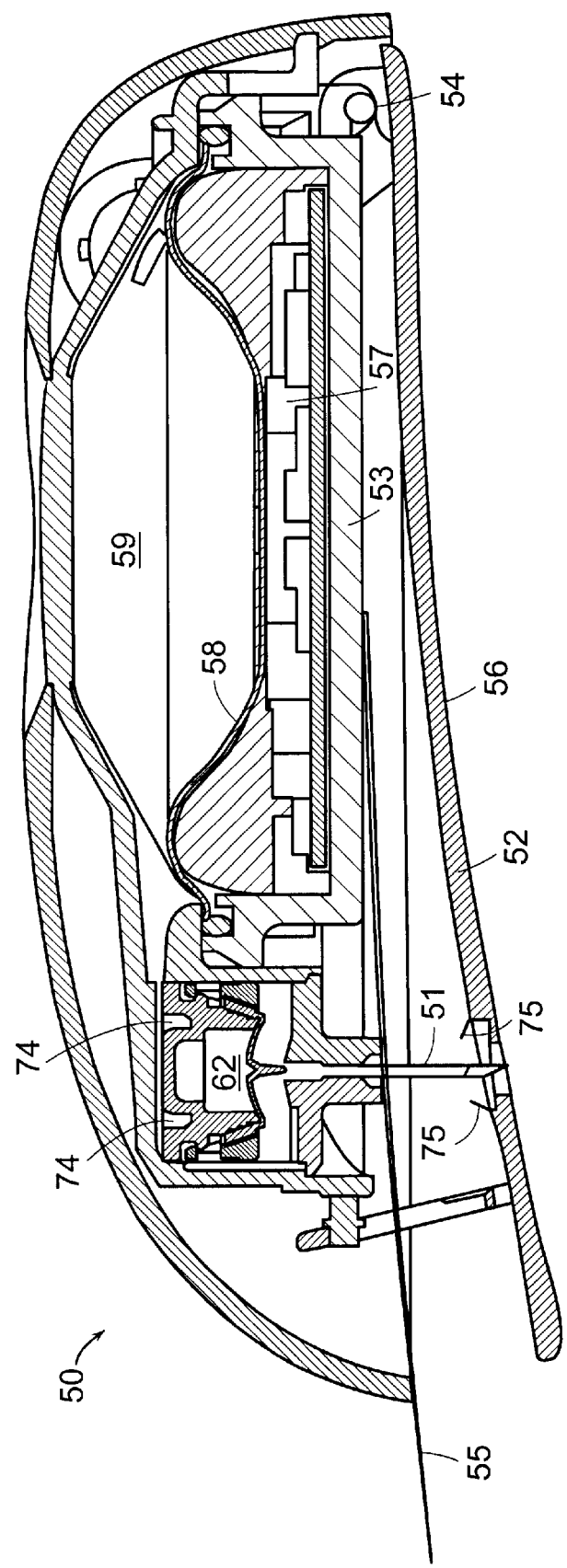
FIGS. 4–6 are sectional side views of a second embodiment of drug delivery device according to the invention, shown before, during and after use, respectively.

Further features of device 10 which can be seen in FIG. 1 are a displaceable cover 29 attached to the housing 11 by a hinge 30. The movement of the displaceable cover 29 between the position shown in FIG. 1 (wherein the needle 21 protrudes through the displaceable cover) and a position in which the needle 21 is substantially concealed by the displaceable cover 29 (as shown in FIG. 4), is controlled by a locking mechanism indicated generally at 31 and explained in greater detail below.

In use, the displaceable cover 29 is affixed to the skin using an adhesive coating 29' provided on the surface thereof distal from the housing ("the underside"). The displaceable cover 29 has a concave shape when viewed from the underside. This shape is advantageous because if a flat or convex surface is provided, the edges of the cover 29 will be more easily peeled away from the skin by accident, i.e. the use of a convex surface is less likely to have protruding edges, and the force required to peel the device away is a shear force rather than a simple peeling force.

The housing 11 is covered by a protective top cover 32 which can provide a more aesthetically pleasing appearance to the device, as well as one which is ergonomically more advantageous for the user. An aperture in protective top cover 32, indicated at 33, allows a transparent portion 34 of the housing 11 to be seen, thereby allowing the user to visually check the reservoir to see whether drug is present. The protective top cover 32 also protects the housing 11 and its component parts if the device 10 is mishandled or dropped.

Figure 3:
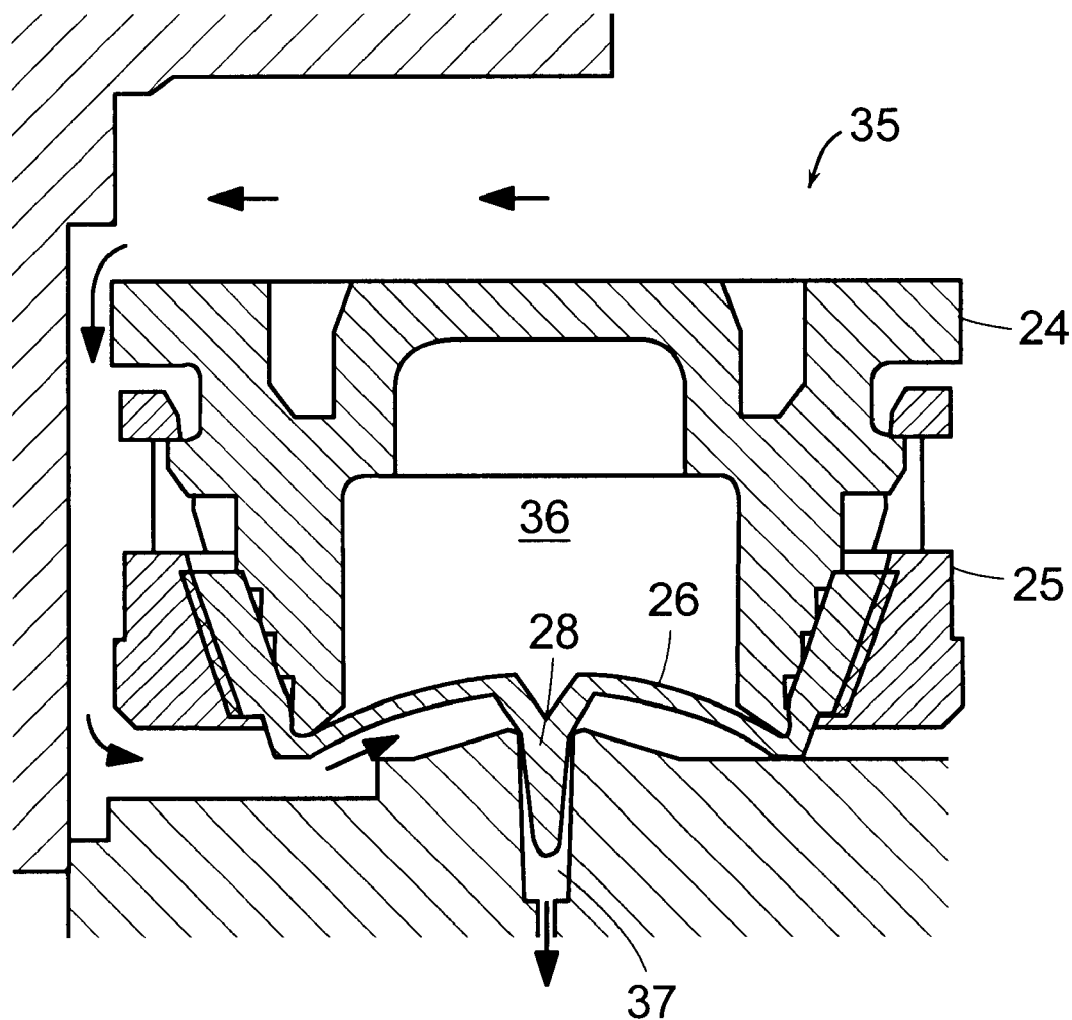
FIG. 3 is an enlarged sectional side view of the flow regulating chamber and needle assembly of the first embodiment of the device of FIG. 1.

The flow regulating chamber 35 is shown in greater detail in FIG. 3 and comprises the top member 24, the annular member 25, and the flow diaphragm 26, as explained above. The construction ensures that the airtight space 36 exists in the interior of the chamber 35. A fluid path between the reservoir and the needle (FIG. 1) is shown with heavy arrows. As can be seen, projection 28 on the flow diaphragm 26 extends into the inlet 37 in the needle holder 27 leading to the needle 21. The fluid has to push up on the flow diaphragm 26 in order to reach the needle 21. Little force is required to do this, as the air in the chamber 36 is compressible.

However, if the ambient atmospheric pressure drops, for example due to an increase in altitude, the fixed mass of air in the chamber 36 tends to expand (since for ideal gases at fixed temperature the product of pressure and volume is a constant). This makes it more difficult for fluid to flow past the flow diaphragm 26 into needle holder 27 and would thus tend to cause a decrease in the rate of delivery of drug.

The fact that the drug is being driven by a gas-filled expandable chamber 14, however, means that the expandable chamber tends also to increase in volume due to this increase in altitude, and the effect of an increase in expandable chamber volume is to speed up the rate of delivery.

Therefore, by calibrating the flow regulating chamber 35 correctly, barometric changes which would otherwise tend to increase or decrease the rate of delivery of drug are counteracted by the corresponding increase or decrease in the amount of flow resistance exerted by the flow regulating chamber, thereby allowing a constant delivery rate to be maintained. It will be appreciated that changes in temperature which would cause the gas in the expandable chamber to expand or contract are also counteracted in the same way.

A further feature of the device of FIGS. 1–3 is an o-ring 38 located on displaceable cover 29 (see FIG. 1). The o-ring 38 forms a seal with needle holder 27 and thereby assists in protecting the puncture point of the needle 21 into the skin of the user from contact with soap, water, perspiration or other contaminates. If water or other liquid contacts the needle 21, the needle 21 may act as a switch and allow water to be drawn into the puncture. However, adhesive 29' on the displaceable cover 29 prevents water from reaching the needle 21 via the underside of the cover, and the o-ring 38 prevents water from reaching the needle via the upper side of displaceable cover. Top member 24, annular member 25, flow diaphragm 26 and needle holder 27 and all other parts in the fluid pathway are preferably made of a polycarbon material. Polycarbon materials are essentially inert and will not react with the liquid drug. Moreover, the polycarbon material withstands gamma radiation without degradation of any properties.

Figure 5:
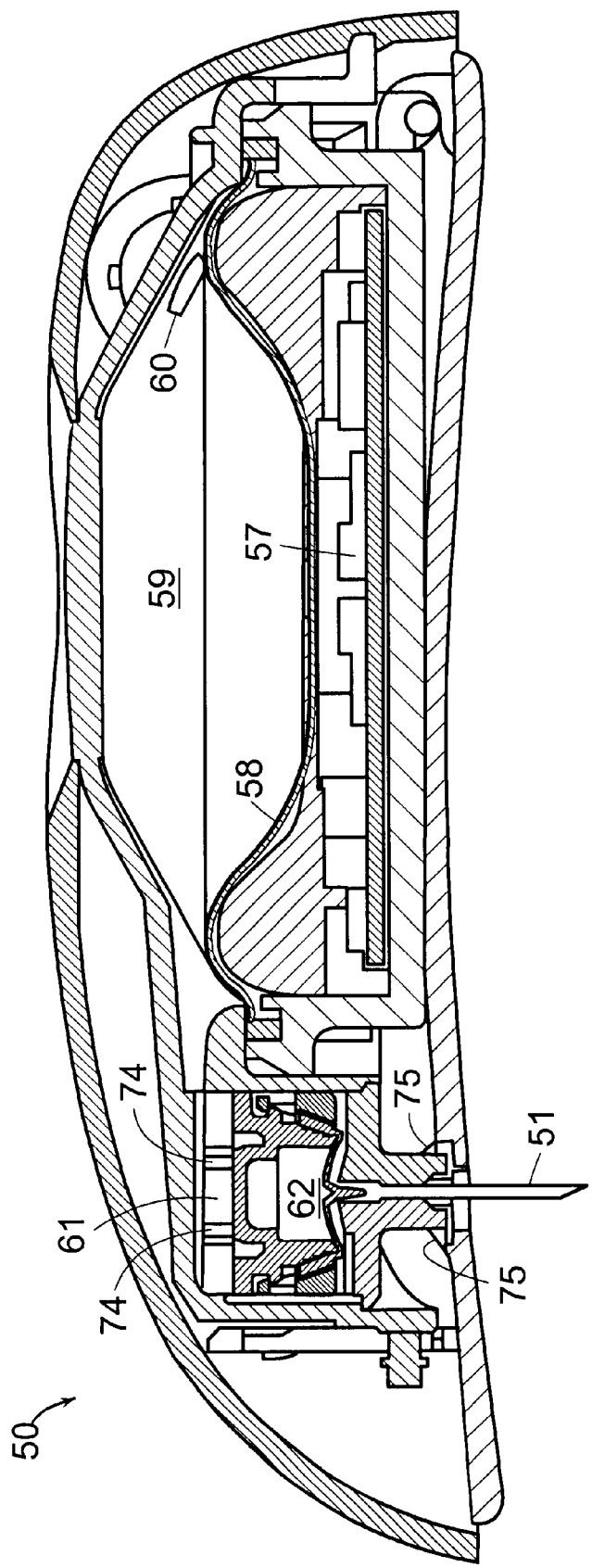
Figure 6:
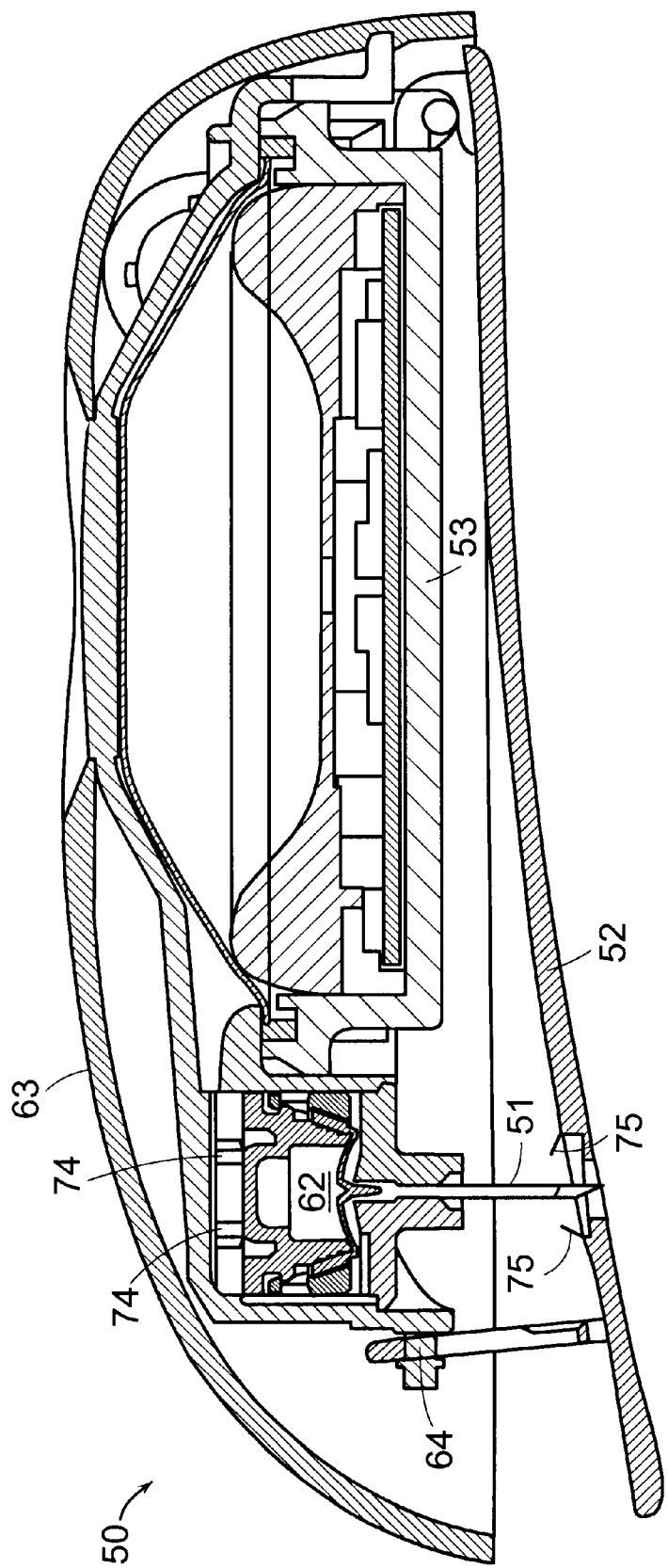

FIGS. 4, 5, and 6 show a device similar to that of FIG. 1 before, during and after use, respectively. The device, indicated generally at 50, differs slightly from the FIG. 1 device and accordingly different reference numerals are used in relative to FIG. 1. The device 50 is shown in FIG. 4 with the needle 51 concealed by the displaceable cover 52 because the displaceable cover 52 is displaced relative to the housing 53 about the hinge 54. A removable tab 55 prevents the displaceable cover 52 from being moved; towards housing 53, as will be described further below. The underside 56 of the displaceable cover 52 is coated with a contact adhesive 56, and during storage, the adhesive is protected by a release liner.

When the release liner is removed, the adhesive-coated underside 56 is pressed against the skin to ensure good adhesion (the concave surface assists in obtaining good adhesion) and the tab 55 is removed. The housing 53 is then pushed towards the skin and the needle 51 penetrates the skin as the displaceable cover 52 and housing 53 move together about hinge 54, leading to the configuration shown in FIG. 5.

A start button is pressed to activate a gas generating electrolytic cell 57. As gas is generated, a diaphragm 58 is pushed upwards to drive a liquid drug from the reservoir 59 (which was filled before use via inlet 60) and thereby force the drug through a fluid path 61 around the flow regulating chamber 62 (as explained above in relation to FIGS. 1–3) and to the patient via the delivery needle 51. When delivery has been completed, the diaphragm 58 will have moved up such that the space occupied by the reservoir 59 at the beginning of delivery (see FIGS. 4 and 5) is now occupied by the expandable chamber 60 (see FIG. 6), since the expansion of the expandable chamber causes contraction of the reservoir.

Figure 7:
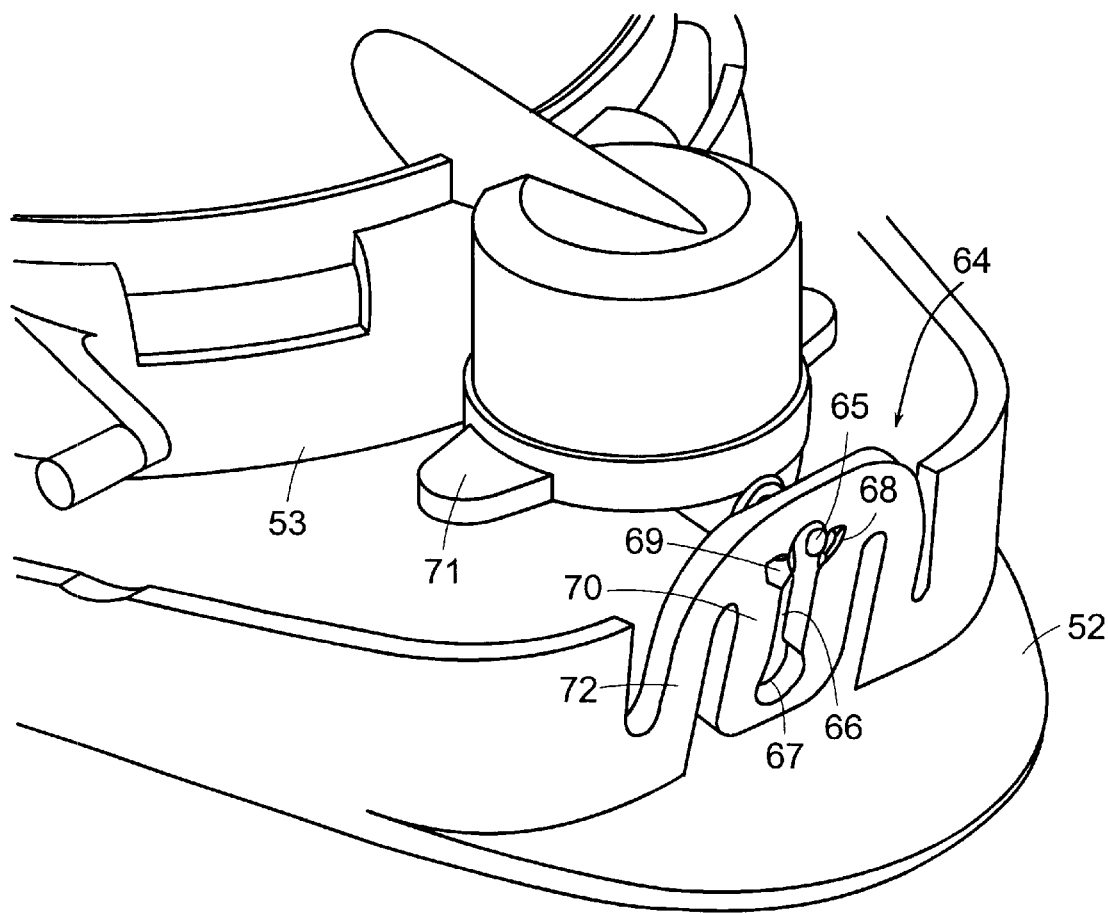
FIGS. 7–9 are enlarged perspective views of the locking mechanism of the device of FIGS. 4–6, shown before, during and after use, respectively.

The device 50 is removed from the skin by pulling upwards on the upper protective cover 63 (FIG. 6). This causes the needle 51 to be retracted behind the displaceable cover 52 once again because the adhesive force holding the displaceable cover 52 against the skin is greater than the force exerted by the locking mechanism 64 (explained in greater detail below). Once the needle 51 is retracted in this way, the locking mechanism 64 holds the displaceable cover 52 permanently in the position shown in FIG. 6, i.e. away from the housing 53 with the needle 51 concealed. FIG. 7 shows locking mechanism 64 in greater detail, with the protective top cover 63 removed for illustrative purposes. The locking mechanism 64 is illustrated before use, i.e. when the displaceable cover is positioned as shown in FIG. 4. In other words, there is a gap between the housing 53 and the displaceable cover 52, and the needle 51 (FIG. 4) is recessed in this gap and thereby concealed by the displaceable cover 52. A projection 65 mounted on the front of housing 53 is positioned at the upper end of a slot 66. The slot 66 has an enlarged portion 67 at the lower end and is provided with wedge projections 68, 69 at the exterior surface of the upper portion thereof. The slot 66 is formed in a member 70 which is attached to displaceable cover 52 by connecting arms 72 which allow a slight degree of flexibility. A widened rib is provided on the projection 65, and the width of this rib is greater than that of the upper portion of the slot 66. The member 70 is biased slightly against this rib.

Figure 8:
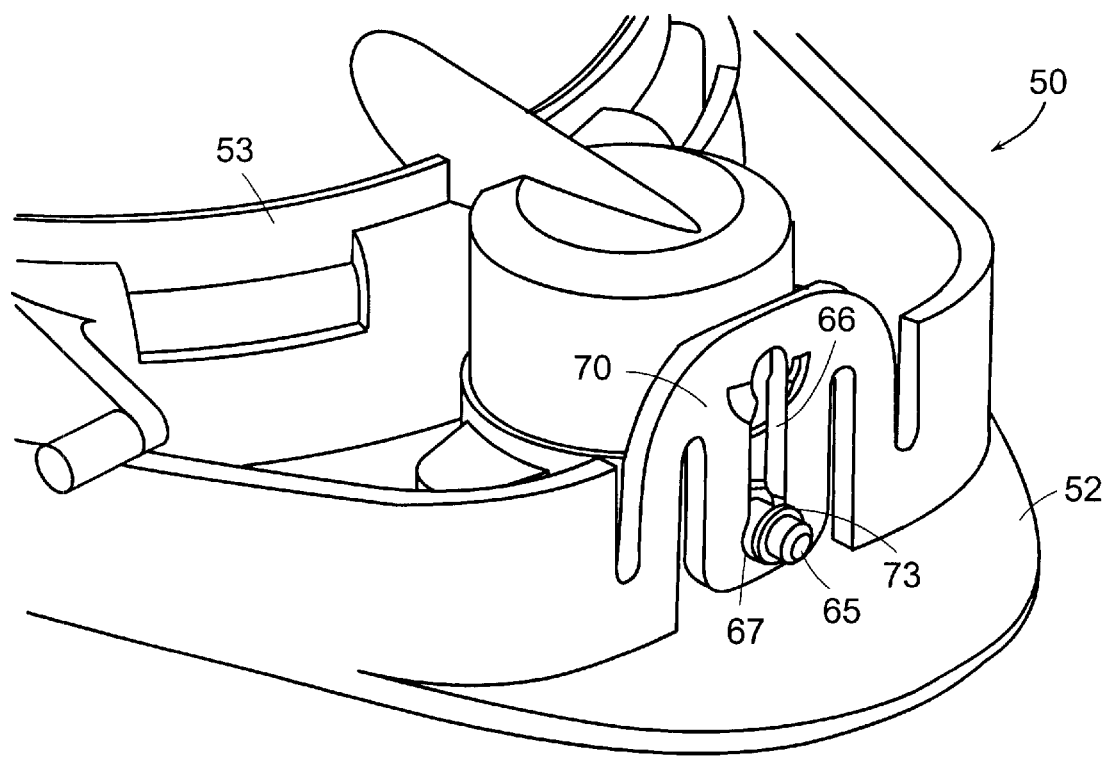

The removable tab 55 (see FIG. 4) is positioned so as to engage wings 71 and prevent them from moving towards the cover 52. This effectively prevents the entire housing 53 from being moved towards the cover 52 and prevents the device from being activated prematurely. When the tab 55 is removed, as shown in FIG. 7, the displaceable cover 52 can be snapped towards the housing 53 by pressing down on the housing. This results in the locking mechanism adopting the configuration shown in FIG. 8, wherein the projection 65 has moved to the lower end of the slot 66, allowing a lipped member 73 to pass through the enlarged portion 67 at the lower end of slot 66. This allows a member 70, which was biased in the direction of projection 65, to relax. The sides of the lipped member 73 rest against the member 70.

Figure 9:
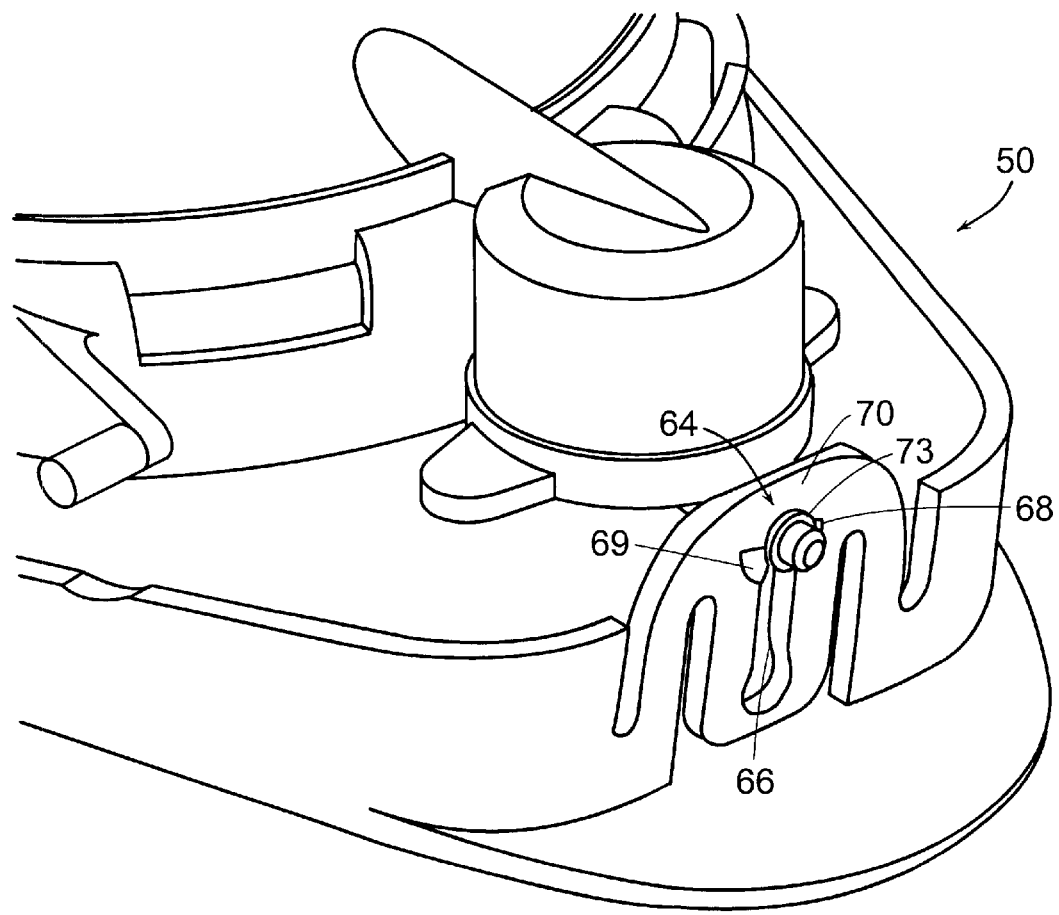

When delivery is complete and the housing 53 is lifted away from the displaceable cover 52, this disengages the lips of the lipped member 73 from resting against member 70 and again moves the projection 65 to the upper end of the slot 66. However, the lipped member 73 passes over the wedge projections 68, and 69, as shown in FIG. 9. When this happens, the wedge projections 68, and 69 catch the lipped member 73 and prevent it from moving back down. This effectively locks the locking mechanism 64 permanently in the configuration shown in FIG. 9, thereby concealing the needle 51 permanently from view and making the device 50 safe for disposal.

An additional feature of the device of FIGS. 4–8 relative to that of FIG. 1 can be seen with reference to FIGS. 4–6. A pair of projections 74 grip the flow regulating chamber 62 before use to block the path between the reservoir 59 and the needle 51 before use (FIG. 4). When gas generation begins, the pressure of liquid in the reservoir 59 forces the flow regulating chamber 62 downwards relative to the projections 74. The projections 74 are resilient and move together when the flow regulating chamber 62 moves downwards. In this position the projections 74 hold flow regulating chamber 62 in a fixed position both during delivery (FIG. 5), and when the device is removed from the skin (FIG. 6). Thus, after delivery, accidental leakage of medicament from the needle 51 (e.g. due to gravity) is prevented by the fixed position of the flow regulating chamber 62 and no gas being generated to create a higher pressure than within the flow regulating chamber 62 to lift the projection which seals the inlet to the needle.

A further feature of the embodiment of FIGS. 4–6 is an annular elastomeric inwardly extending lip 75 which seals the skin at the point of entry of the needle 51 in the same manner as the o-ring 38 in the FIG. 1 embodiment. This feature reduces the danger of infection due to wicking by the needle of unwanted substances into the skin.

Four alternative embodiments of different locking mechanisms according to the invention are shown in FIGS. 10A–10D, 11A–11D, 12A–12D, and 13A–13E. In each case the mechanism is shown schematically in "pre-use" (A), "in-use" (B) and "post-use" (C) configurations as well as in one or two perspective views (D/E). The mechanism can in each case be moved from position A to position B and from position B to position C with little difficulty (although generally some resistance is present to prevent spontaneous or accidental movement), but once in position C, the mechanism is effectively locked permanently and is no longer capable of operation.

Figure 10A:
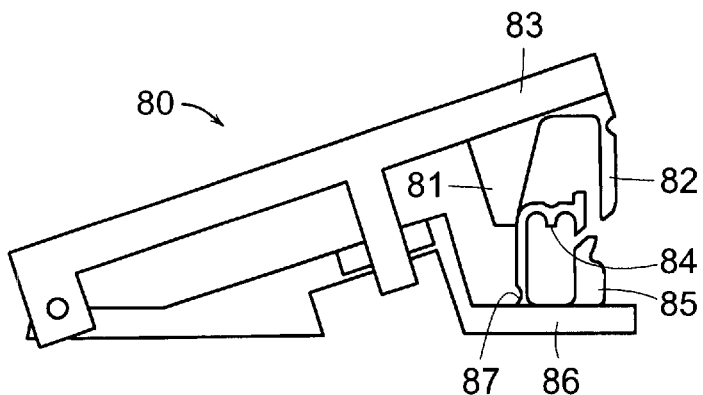
FIG. 10A, 10B and 10C are schematic elevations of a first alternative embodiment of a locking mechanism, shown before, during and after use, respectively.

The first alternative embodiment of a locking mechanism comprises a resilient arm and related assembly and is shown in FIGS. 10A–10D. In FIG. 10A the locking mechanism is indicated generally at 80 and comprises a biasing member 81 and a resilient strut 82 mounted on a housing 83, and the resilient arm 84 and a post 85 mounted on a displaceable cover 86.

The resilient arm 84 is flexibly hinged at the base thereof 87. When the housing 83 is pushed towards the displaceable cover 86, the biasing member 81 pushes the resilient arm 84 against the post 85. The resilient arm 84 and post 85 are mutually shaped to allow the arm 84 to pass over the top of the post 85, where it latches (see FIG. 10B) and is prevented from returning to the position shown in FIG. 10A.

Figure 10B:
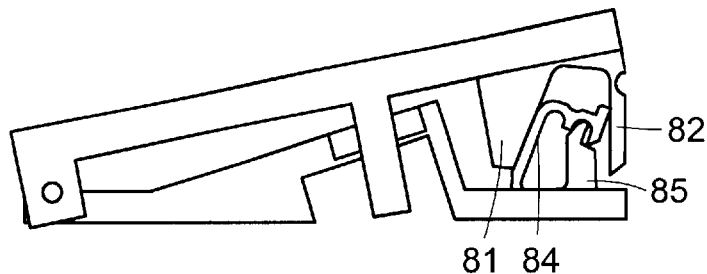

In passing over the top of the post 85, the arm 84 acts against the resilient strut 82, momentarily bending the strut 82 away from the biasing member 81. Although when the arm 84 has passed fully over the top of the post 85 the strut 82 has returned to its relaxed (straight) position (FIG. 10B).

When (after use) the housing 83 is pulled away from the displaceable cover 86, this causes the strut 82 to again be bent away from biasing member 81 (because arm 84 which is now locked in place by post 85 impedes the path of strut 82). However, when the end 88 of strut 82 has cleared the arm 84, it springs back into position, past a projection 89 on arm 84 (see FIG. 10C). In fact, strut 82 latches behind projection 89, preventing the strut from moving back to the position shown in FIG. 10B, and thereby permanently locking the mechanism 80 in the FIG. 10C configuration.

Figure 10C:
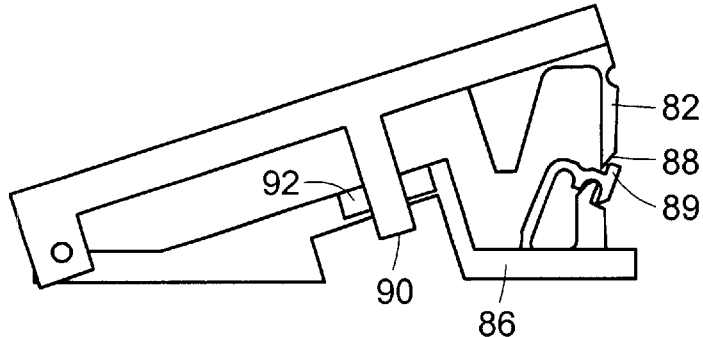
Figure 10D:
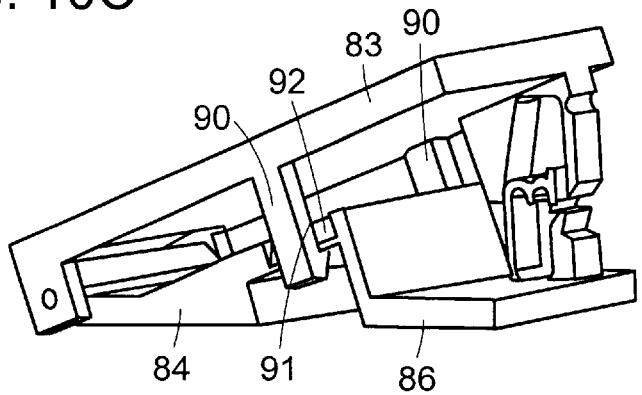
FIG. 10D is a perspective view of the locking mechanism as shown in FIG. 10A.

The perspective view in FIG. 10D shows the mechanism in the position illustrated in FIG. 10A. An additional feature visible in FIG. 10D is a snap mechanism comprising an arm 90 depending from either side of the housing 83. A raised protuberance 91 on the inner surface of each arm 90 acts against a sloped surface 92 on the displaceable cover 86 to provide resistance to movement. The effect of the snap mechanism is to add further resistance to any unintended relative movement between the housing 83 and the displaceable cover 86. A further effect is that the movement of the housing 83 relative to the cover 86 between the configurations of FIGS. 10A and 10B, and the configurations of FIGS. 10B and 10C, is extremely rapid, causing the penetration of the needle into the skin and the removal of the needle from the skin to be quick and painless.

Figure 11A:
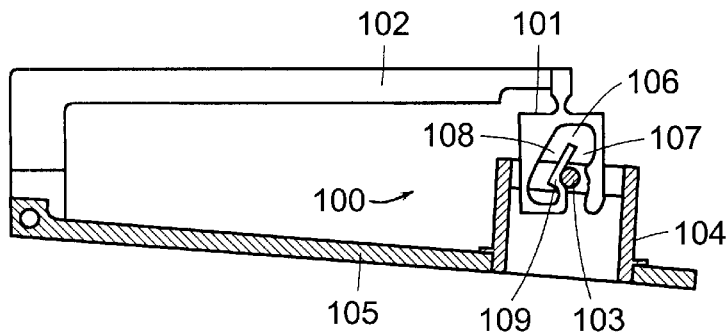
FIGS. 11A, 11B and 11C are schematic elevations of a second alternative embodiment of a locking mechanism, shown before, during and after use, respectively.

The second alternative embodiment of a locking mechanism of the present invention comprises an inverted V-shaped assembly and is shown in FIGS. 11A–11D. In FIG. 11A the locking mechanism is indicated generally at 100 and comprises a member 101 resiliently mounted on a housing 102, and a pin 103 supported in a frame 104 mounted on a displaceable cover 105. The member 101 has an inverted V-shape slot 106 therein. The slot 106 has an outer slot portion 107 connected at the upper end thereof to an inner slot portion 108, and a dividing member 109 between the outer and inner slot portions 107, 108 below the upper ends.

In moving from the "pre-use" position to the "in-use" position, the (fixed) pin 103 moves up the outer slot 107, acting against the dividing member 109 until it springs past the dividing member 109 at the top of the outer slot. In the position shown in FIG. 11B, the pin 103 is located above the top of the inner slot 108.

Figure 11B:
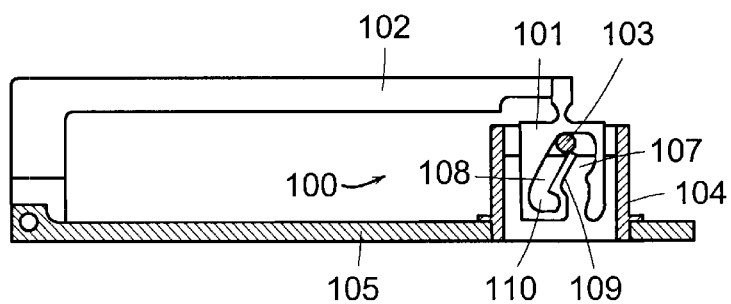
Figure 11C:
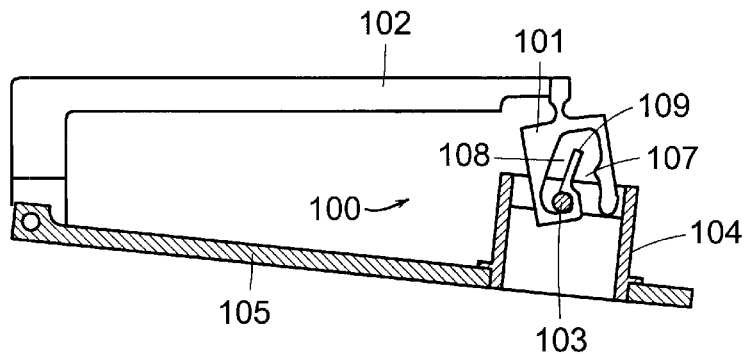
Figure 11D:
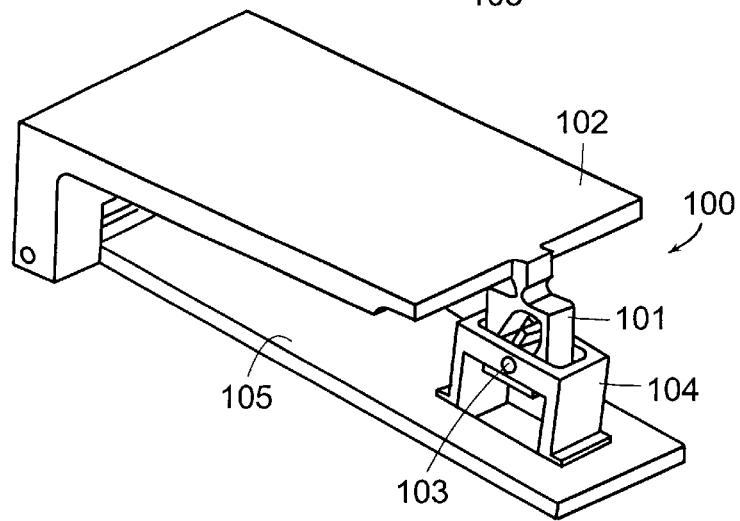
FIG. 11D is a perspective view of the locking mechanism as shown in FIG. 11A.

When the housing 102 is subsequently pulled away from the displaceable cover 105 (moving from FIG. 11B to FIG. 11C, the pin moves down inner slot 108, acting against the dividing member 109 to push the member 101 sideways. When the position shown in FIG. 11C is reached, the pin 103 locates a recess 110 (see FIG. 11B) in the lower end of inner slot 108, which allows the member 101 to relax slightly but still keeping a certain degree of stress on the member 101 by holding it away from the equilibrium position relative to the housing 102. In this way, the pin 103 latches into the recess 110 and locks the mechanism 100 permanently in the "post-use" configuration. In FIG. 11D, the mechanism 100 can be seen in the "pre-use" configuration, with the member 101, housing 102, pin 103, frame 104, and displaceable cover 105 visible.

Figure 12A:
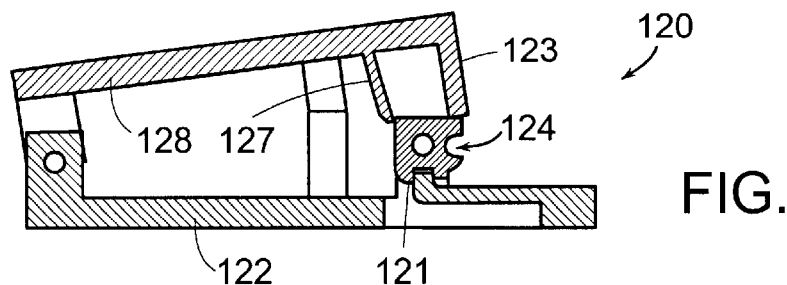
FIGS. 12A, 12B and 12C are schematic elevations of a third alternative embodiment of a locking mechanism, shown before, during and after use, respectively.
Figure 12B:
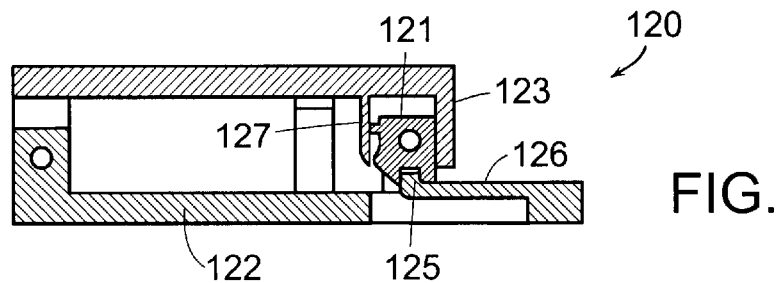
Figure 12C:
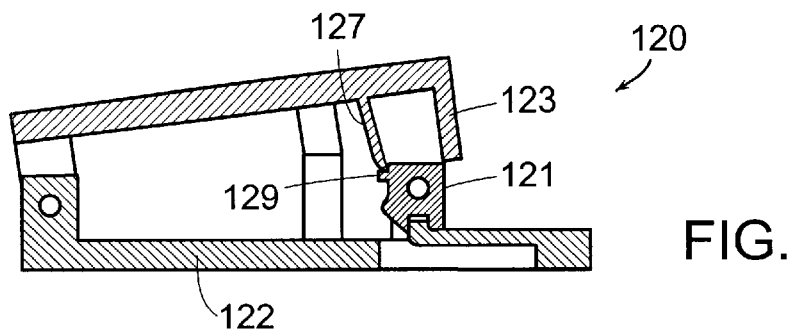
Figure 12D:
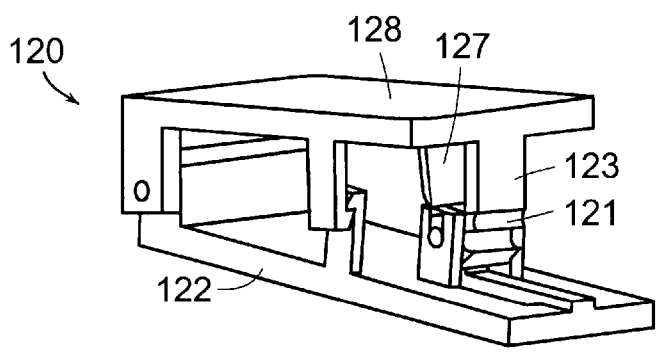
FIG. 12D is a perspective view of the locking mechanism as shown in FIG. 12A.

The third alternative embodiment of a locking mechanism of the present invention comprises generally a rotatable pawl assembly and is shown in FIGS. 12A–12D. The mechanism, indicated generally at 120, comprises a rotatable pawl 121 mounted on the displaceable cover 122 and which is rotated by an arm 123 in moving from the "pre-use" to "in-use" positions (FIGS. 12A and 12B, respectively). When the rotatable pawl 121 reaches the "in-use" position, a recess 124 (FIG. 12A) receives a projection 125 located on a resilient portion 126 of the displaceable cover 122, providing a degree of resistance to further movement.

In moving from the FIG. 12A to 12B positions, the rotatable pawl 121 acts against a flexible strut 127 depending from the housing 128. When the rotatable pawl 121 is in the FIG. 12B position, further clockwise rotation of the pawl is prevented by the arm 123.

When the housing 128 is lifted (moving from FIG. 12B to 12C), the strut 127 acts against a projection 129 urging the rotatable member 121 in a clockwise direction, but the arm 123 prevents such rotation. As the housing reaches the FIG. 12C position, the strut 127 springs past the projection 129 to sit in a recess above the projection 129, and the arm 123 clears the upper corner of the rotatable pawl 121. When in this configuration, the arm 123 prevents any counter-clockwise rotation of the rotatable pawl 121, while the strut 127 prevents any clockwise rotation thereby locking the rotatable pawl 121 in position and preventing any further downward movement of the housing 128 towards displaceable cover 122.

Figure 13A:
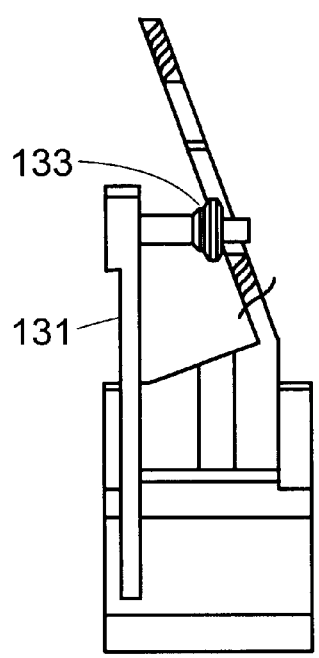
FIGS. 13A, 13B and 13C are schematic elevations of a fourth alternative embodiment of a locking mechanism, shown before, during and after use, respectively.
Figure 13B:
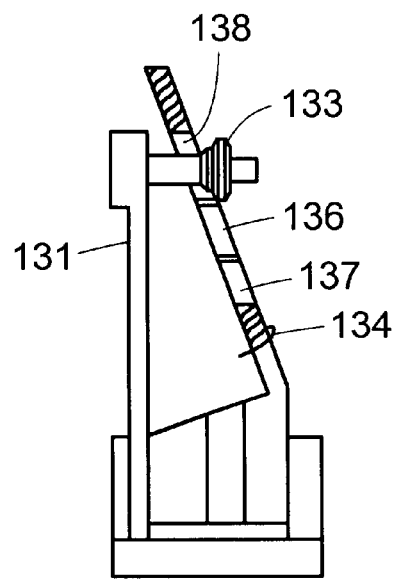

The fourth alternative embodiment of a locking mechanism of the present invention comprises generally a flexible post assembly as shown in FIGS. 13A–13E. In FIG. 13A the locking mechanism is indicated generally at 130 and comprises a vertical flexible post 131 (see FIGS. 13D and 13E) mounted on the displaceable cover 132 and having a projection 133 extending therefrom towards a sloped surface 134 on the housing 135.

A slot 136 in surface 134 connects two apertures, namely a lower aperture 137 (see FIG. 13B) which is of smaller diameter than the widest part of projection 133, and an upper aperture 138 which is of larger diameter than the widest part of projection 133.

Figure 13C:
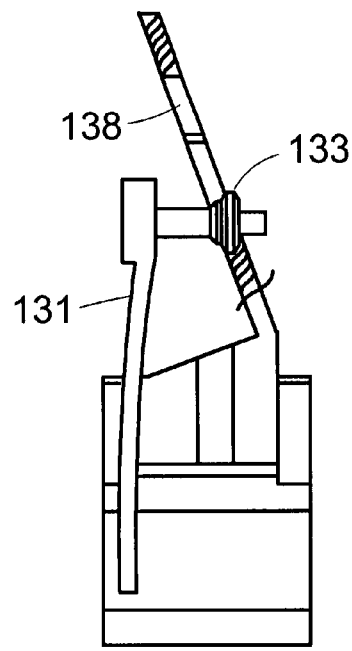
Figure 13D:
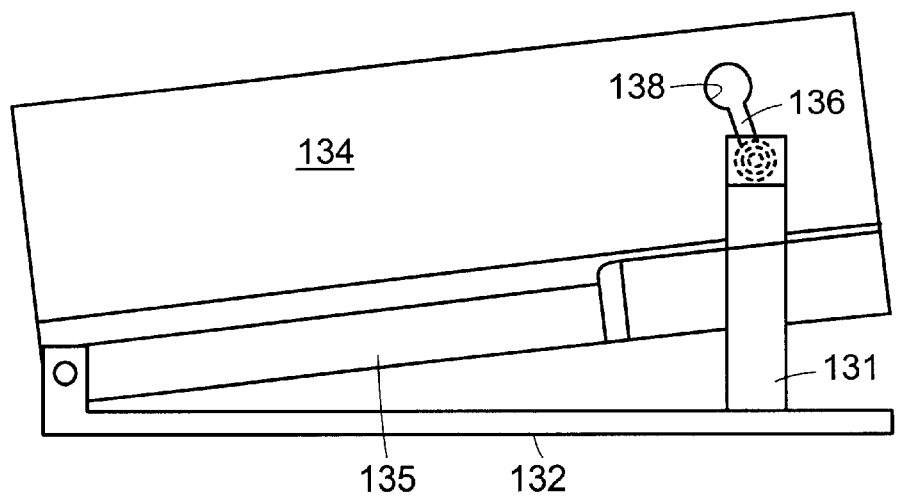
FIG. 13D is a side elevation of the locking mechanism as shown in FIG. 13A.
Figure 13E:
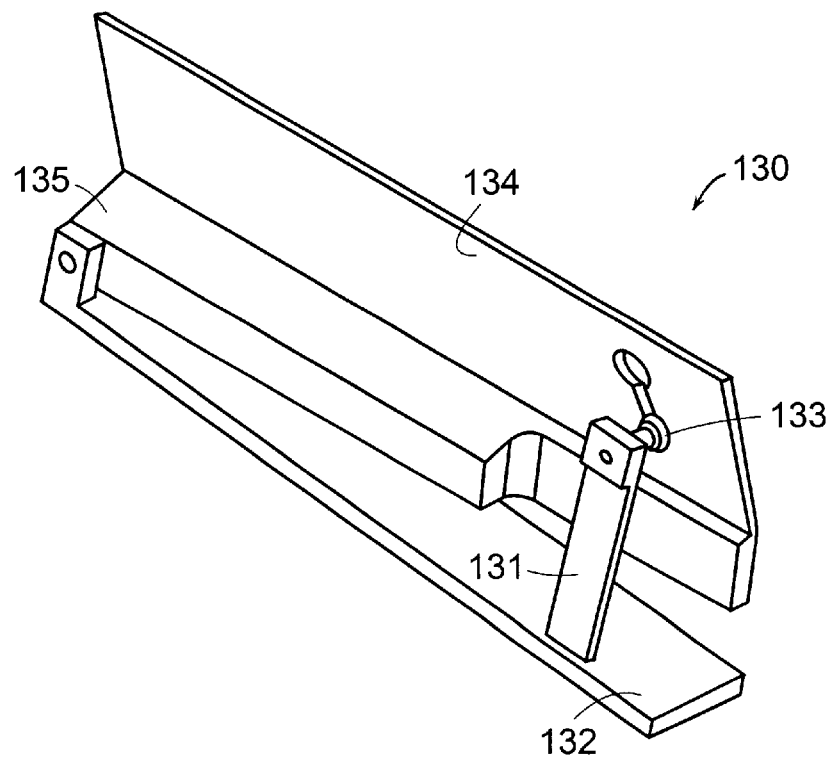
FIG. 13E is a perspective view of the locking mechanism as shown in FIG. 13A.

In the "pre-use" position, projection 133 is positioned at the lower aperture. As the housing moves towards the "in-use" position (FIG. 13B) the flexible arm 131 is bent back until the projection 133 reaches the upper aperture 138 whereupon it springs back into position as the projection 133 moves through the upper aperture 138. In moving to the "post-use" position, the projection 133 is constrained by the slot 136 and the arm 131 is bent forward until the projection 133 reaches the lower aperture 137 which provides a recess for the projection 133 to spring back into (but not through). Because the arm 131 remains bent forward slightly, this effectively traps the projection 133 in the lower aperture 137 and thereby holds the mechanism permanently in the "post-use" configuration, as shown in FIG. 13C.

Figure 14:
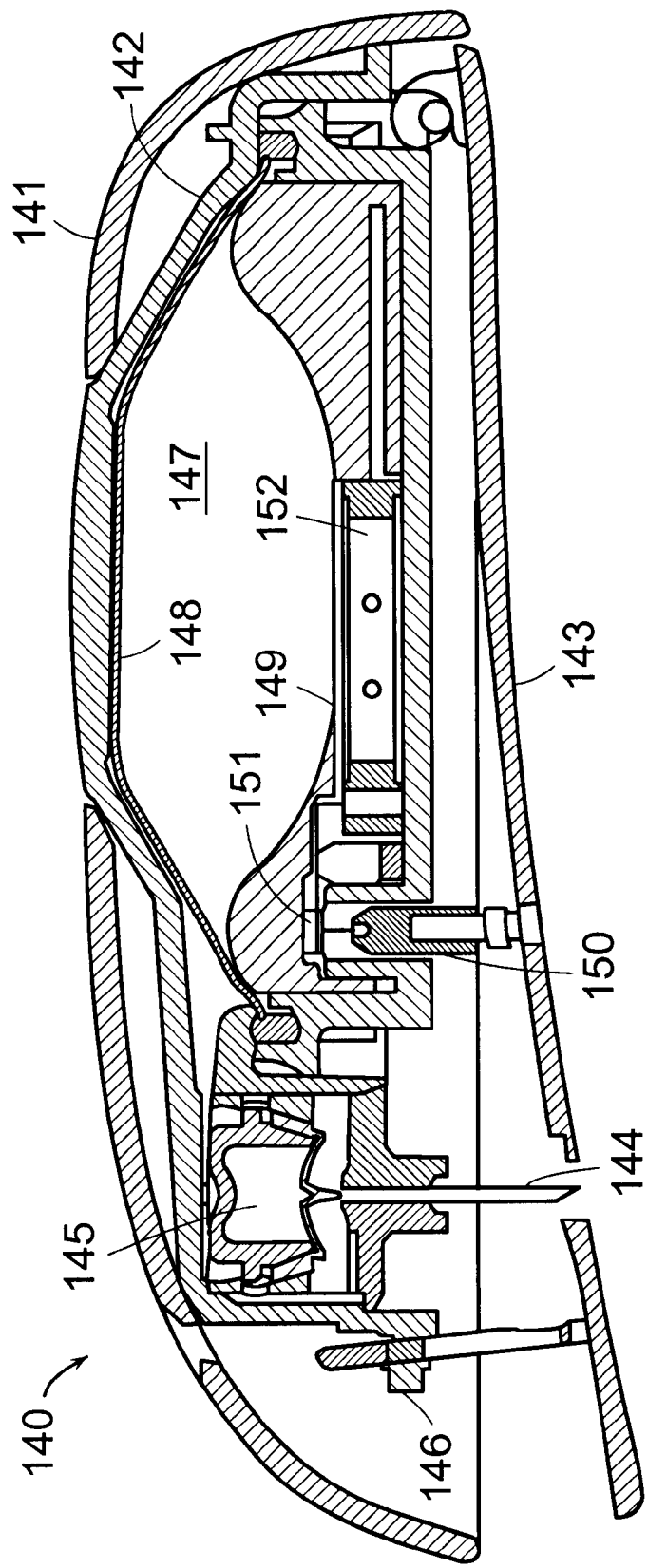
FIGS. 14 and 15 are sectional elevations of a third embodiment of drug delivery device according to the invention, shown before and during use, respectively.

In FIG. 14 there is another drug delivery device 140 according to the invention similar in many respects to the embodiments previously described. The device 140 has a protective upper cover 141, a housing 142, a displaceable cover 143, a delivery needle 144, a flow regulating chamber 145 and a three position locking mechanism 146.

The internal space of the drug delivery device 140 of FIG. 14 defines an expandable chamber 147 when the diaphragm 148 is in the position shown or a reservoir when the diaphragm is in the position shown in dotted outline at 149. The expandable chamber 147 is initially air filled (FIG. 14 shows the device in the pre-use configuration before medicament has been loaded). Thus, the reservoir is substantially of zero volume. The expandable chamber 147 communicates with the atmosphere via an open valve 150.

When liquid drug is loaded into the reservoir via a fill, the diaphragm 148 moves downwards to position 149, with the reservoir filling with air and the expandable chamber 147 being emptied as the volume thereof decreases. Because the expandable chamber 147 is in communication with the atmosphere, the air initially filling the chamber 147 is exhausted into the atmosphere via the valve 150 without any necessity for action on the part of the user.

Furthermore, because the reservoir is initially of substantially zero volume, it does not require filling in any particular orientation. While prior art devices have required careful loading in order to ensure that all air bubbles are vented from the drug supply before delivery begins, the only air in the drug path of the device of FIG. 14 is in the short, narrow portion of the device between the reservoir and the needle 144. Thus, when drug enters the reservoir it immediately pushes the small amount of air ahead of it through the narrow space towards the needle 144, irrespective of the orientation of the device 140. By filling with the drug until a drop of the drug appears on the end of the needle 144 one can be sure that no air remains in the fluid path.

When the device 140 has been filled with drug, the diaphragm 148 is at the position shown at 149, and the valve 150 is open. However, when the displaceable cover 143 is applied to the skin, and the housing is pushed downwards, the valve 150 is closed and the closing of the valve actuates a switch 151 to begin generation of gas by an electrolytic cell 152 (described in more detail below).

Figure 15:
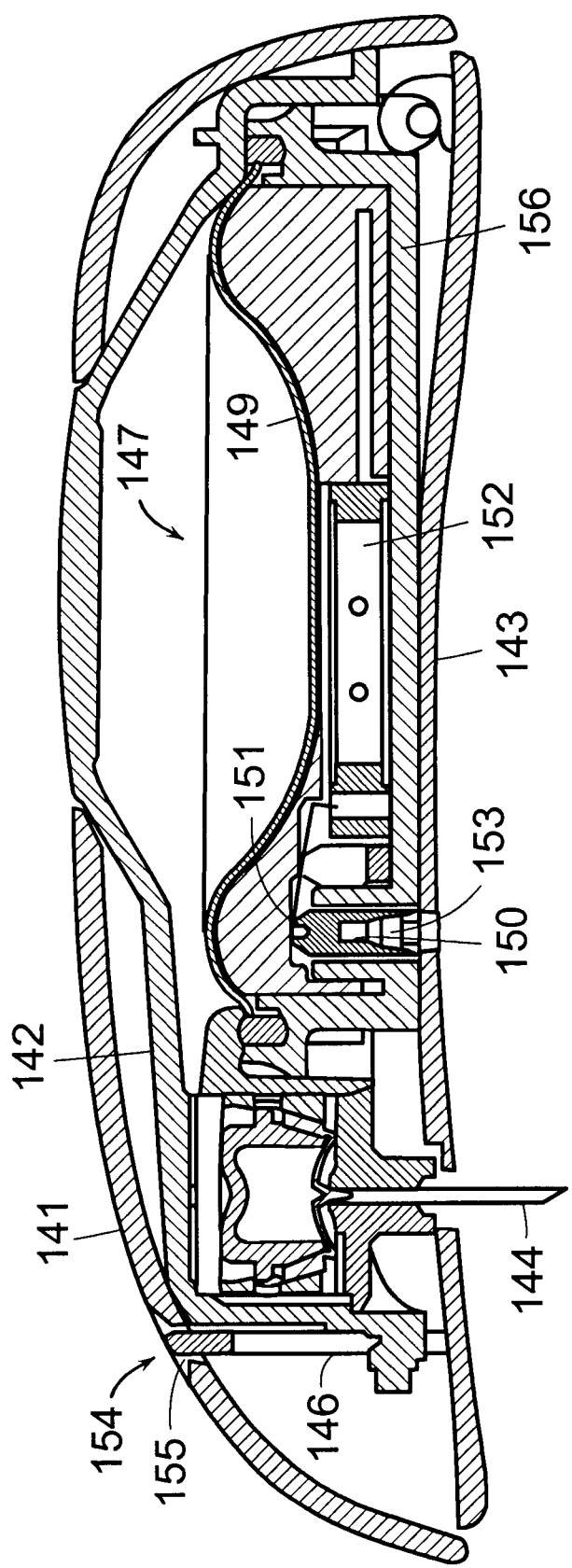

The device 140 is then in the "in-use" position shown in FIG. 15, with reservoir 147 filled with drug, the diaphragm 148 in position 149, valve 150 and switch 151 closed, and electrolytic cell 152 actuated to generate a gas and hence begin delivery of drug from reservoir to the patient through delivery needle 144.

Valve 150 is closed by a connecting member 153 which is connected to displaceable cover 143. When displaceable cover 143 moves towards housing 142, connecting member 153 fits into a valve 150 and pushes it home to seal the expandable chamber 147 (the area below diaphragm 149) from the atmosphere. When a gas is generated by the electrolytic cell 152, it pressurizes the reservoir 147.

A coloured plastic member 154 forming part of locking mechanism 146 protrudes through an aperture 155 in the protective upper cover 141 when the device 140 is in the position as shown in FIG. 15. The coloured member 154 visually indicates that the device 140 has been actuated.

Figure 16:
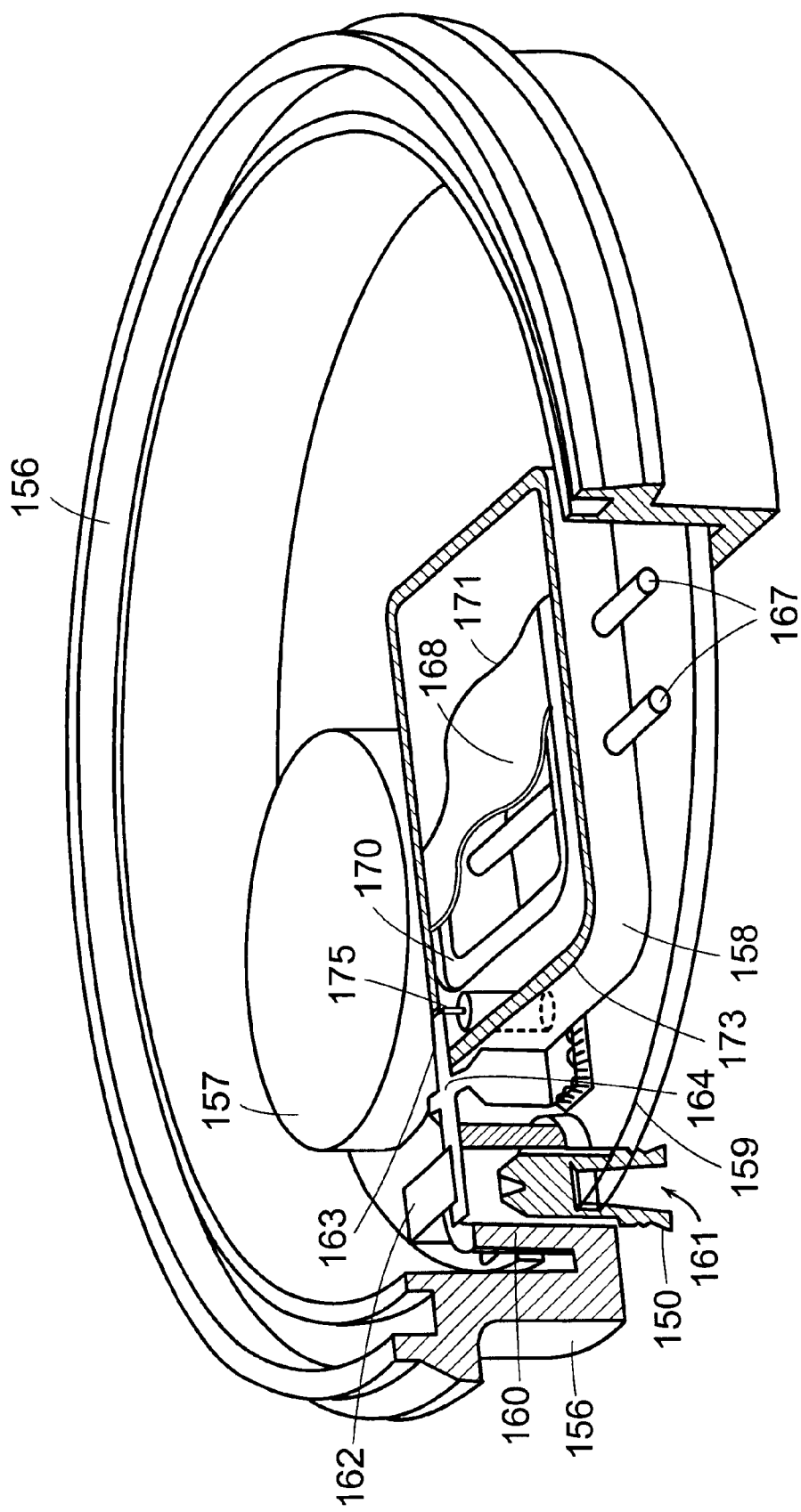
FIG. 16 is a partially cut away perspective view of the lower part of the housing on the device of FIGS. 14 and 15, including various components housed therein.

FIG. 16 is a detail view of the lower section 156 of the housing 142 (see FIG. 15). The lower section 156 houses a battery 157 and an electrolytic cell 158, both mounted on a printed circuit,board (PCB) 159. The PCB 159 can be provided with controlling circuitry as required in order, for example, to vary the rate of delivery, stop delivery if the rate of gas generation is too high, or control the operation of the device 140 in any other way required. In the embodiment shown, the device 140 is a disposable single-rate device which does not require advanced controlling circuitry, but more sophisticated devices are of course within the scope of the invention.

A cylindrical outlet 160 is formed in section 156, and this provides a valve seat for the valve 150. When the valve 150 is pushed upwards into an outlet 160 it makes an airtight seal, as shown in FIG. 15. A recess 161 in the valve 150 tightly accommodates the connecting member 153 (FIG. 15), and the force used to push the housing 142 down onto displaceable cover 143 as described above is sufficient to jam the connecting member 153 into the valve 150. This design enables the device 140 to be removed from the skin by pulling housing 142 away from displaceable cover 143 to the "post-use" position, causing the connecting member 153 (which is permanently mounted on displaceable cover 143 and at this stage jammed into valve 150 also) to pull the valve 150 down and out of outlet 160 so as to open the valve. Using this design, if the reservoir 147 is not empty when the device 140 is removed, and if gas generation continues, then the gas will escape through outlet 160 rather than driving further drug through the needle 144.

As described above, when the valve 150 is closed, it actuates a switch 151 (see FIG. 15) which comprises a fixed contact 162 and a rocking contact 163. This completes a circuit to connect a battery 157 to an electrolytic cell 158. When the valve 150 is pulled downwards as the device 140 is removed from the skin, the switch 151 should automatically disconnect because of the resilience of rocking contact 163 which pivots about a fulcrum 164. Thus, the opening of the valve 150 is generally a redundant feature and is important as a safety feature if the switch 151 does not automatically disconnect (leading to an unwanted continuation of delivery or, if the reservoir 147 is already empty, to a build up of gas pressure inside the device 140).

Figure 17:
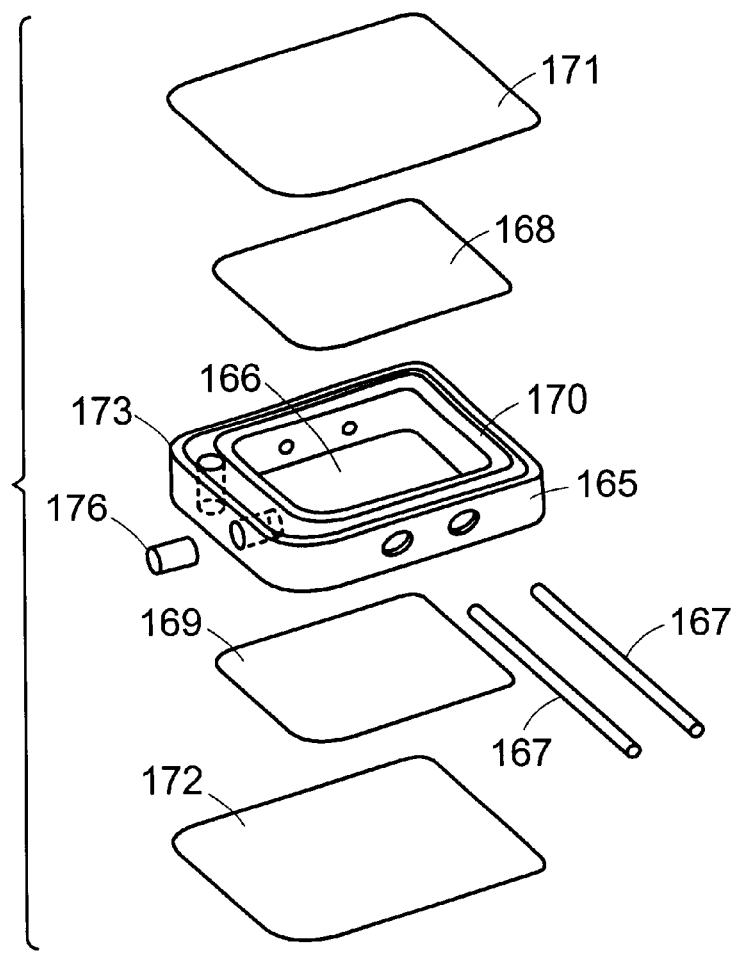
FIG. 17 is an exploded perspective view of the electrolytic cell used in the embodiment of FIGS. 14 and 15.
Figure 18:
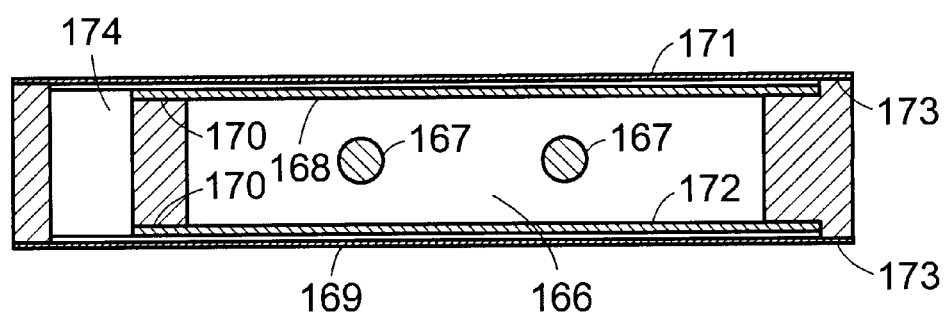
FIG. 18 is a sectional side view of the electrolytic cell used in the embodiment of FIGS. 14 and 15.

The electrolytic cell 158 comprises (see also FIGS. 17 and 18) a body 165 defining an internal space 166 for an electrolyte and through which a pair of electrodes 167 pass, each electrode being connected to a terminal of battery 157 (FIG. 16). The internal space 166 is enclosed above and below by a pair of hydrophobic filters 168 and 169. These filters 168 and 69 retain the electrolyte but allow gas generated in the cell 158 to be released to the expandable chamber 147. The hydrophobic filters 168 and 169 are positioned on the body 165 such that gas will transfer out of the gas generator irrespective of the orientation. The top and bottom of the body 165 is provided with a seating 170. The filters 168 and 169 are placed in the seating 170 above and below the body 165 and are sealed in place. In a preferred embodiment, the body 165 is an injected molded high density poly ethylene (HDPE) to minimize permability.

The cell 158 is then sealed above and below by aluminum foil layers 171 and 172. A connecting cell 174 sealed at both ends by foil layers 171 and 172 enables gas passing through the hydrophobic filters 168 and 169 to be released, once the top foil layer 171 has been pierced. A gap adjacent to the seating 170, enables gas escaping through hydrophobic filters 168 and 169 to reach the connecting cell 174. The foil layer 171 is pierced by a spike 175 carried on rocking contact.163 (see FIG. 16). Thus, when the device 140 is actuated, the foil layer 171 is pierced to unseal the cell 158. A hydrophobic filter 176 (see FIG. 17) is also carried in the body 165 to enable the cell 158 to be filled with electrolyte by injection.

Figure 19:
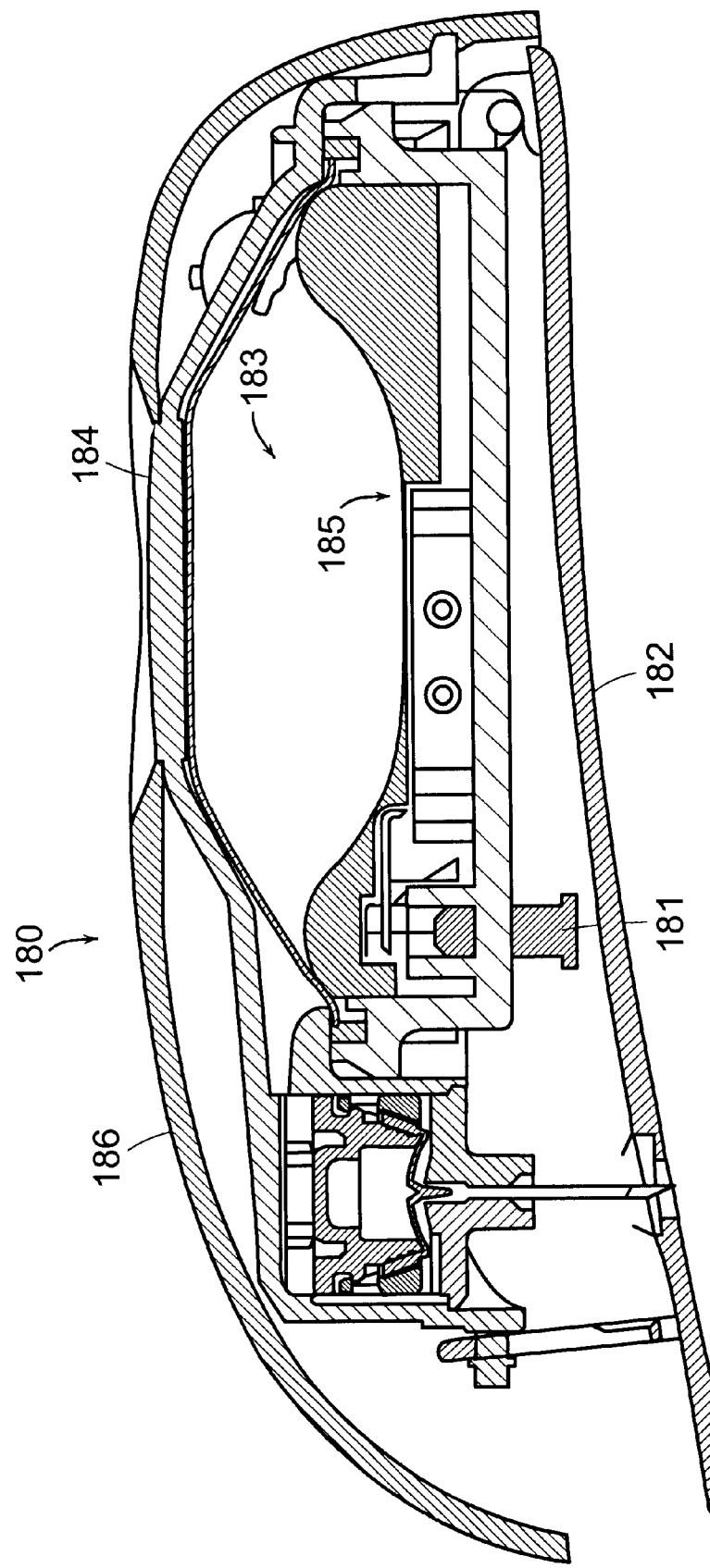
FIGS. 19 and 20 are sectional side views of a fourth embodiment of drug delivery device according to the invention, shown before and during use, respectively.
Figure 20:
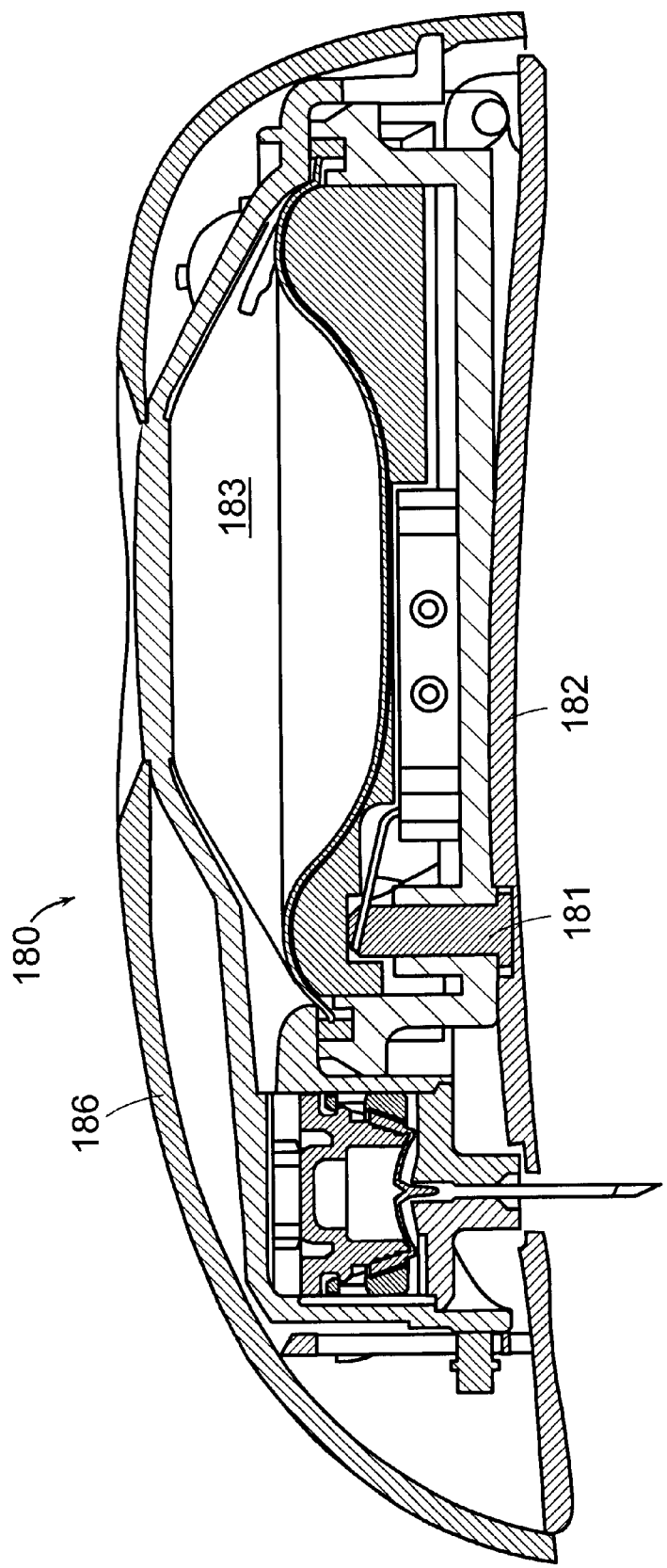

In FIGS. 19 and 20, a further embodiment 180 of the invention is shown. This embodiment differs from the embodiment of FIGS. 14–18 only in that the valve member 181 is not held by the displaceable cover 182 when the device 180 is removed from the skin after use. However, the valve 181 nevertheless achieves the primary purpose of allowing the internal space 183 to be occupied entirely by the expandable chamber when received by the user, with the diaphragm 184 moving to the position shown at 185 when the device 180 is loaded with medicament. This means that no air bubbles can be entrapped in the reservoir during filling, and the reservoir can thus be filled quickly and easily. The valve 181 closes automatically when the housing 186 is pressed towards the displaceable cover 182 (see FIG. 20).

Figure 21:
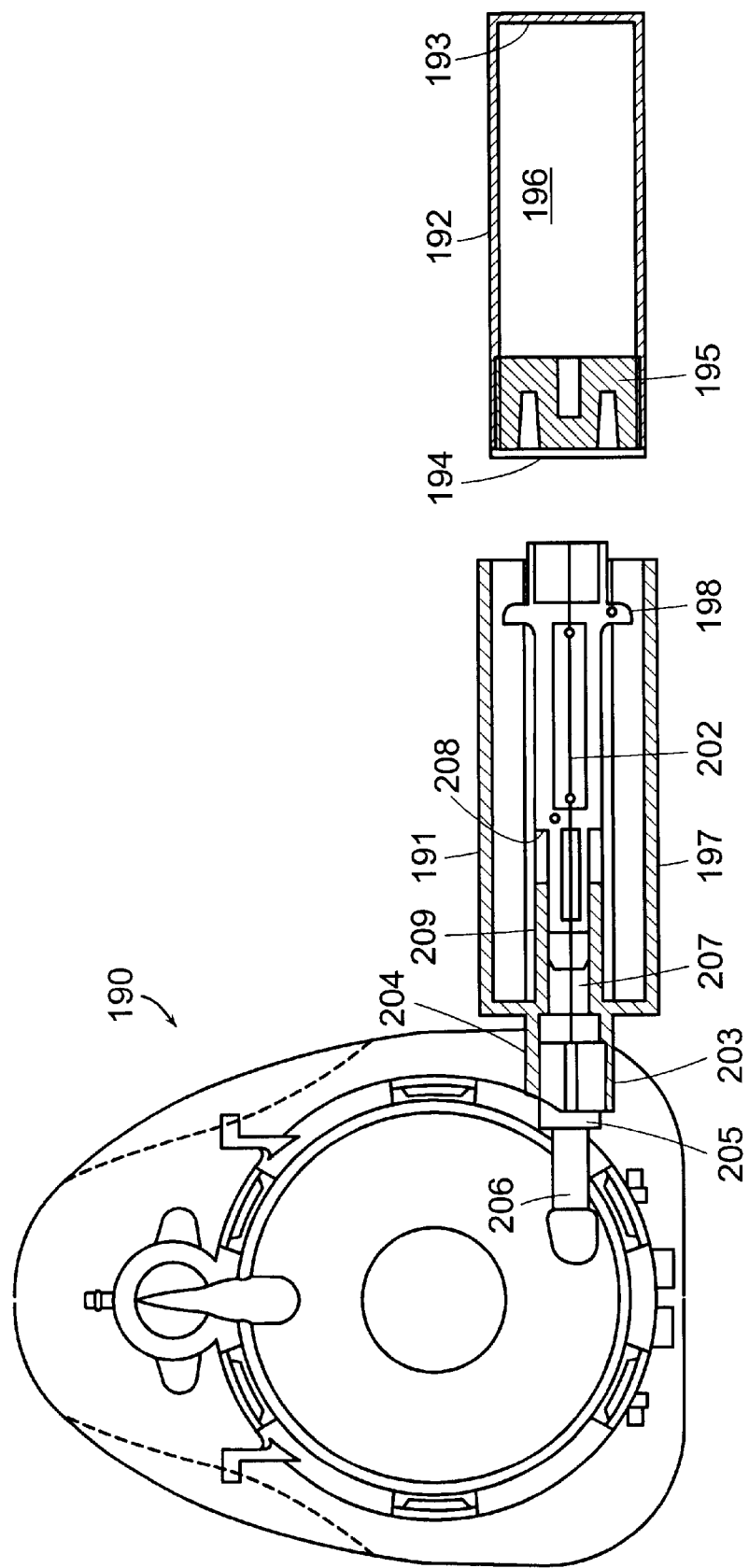
FIG. 21 is a sectional plan view of a drug delivery kit comprising the first embodiment of FIG. 1, a filling adapter and a medicament cartridge.

FIG. 21 shows a device 190 according to the invention which is identical to the device of FIG. 1, together with a filling adapter 191 and a drug-containing cartridge 192. Cartridge 192 is cylindrical in shape, closed at one end 193 thereof and sealed at the other end 194 by an elastomeric stopper 195 which is fittably mounted in the cartridge 192. Because the cartridge's liquid-filled internal space 196 is sealed, the stopper 195 is prevented by the incompressible nature of the liquid from moving in either direction.

Figure 22:
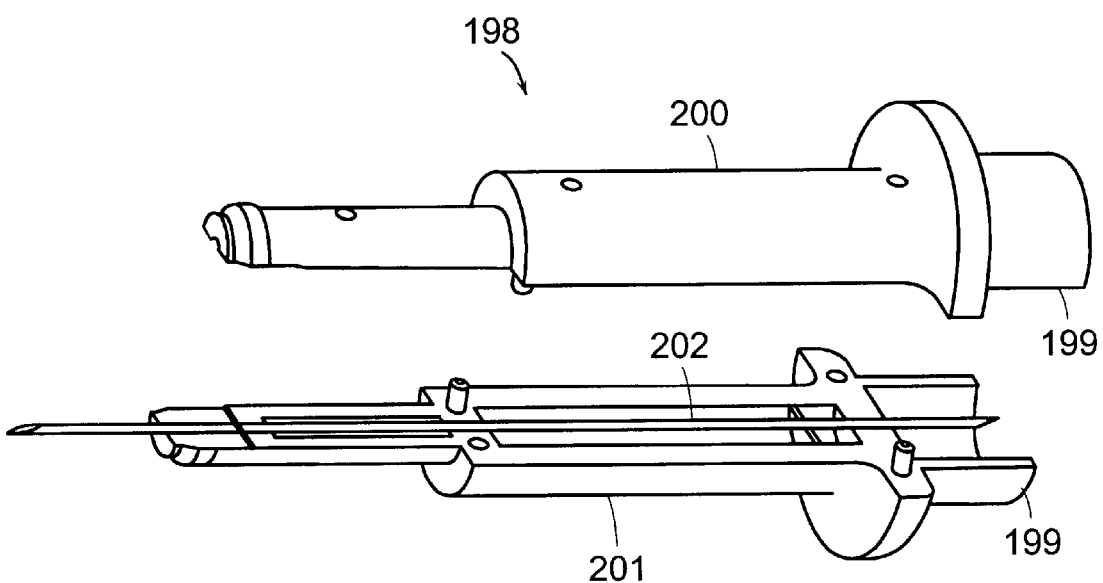
FIG. 22 is a perspective view of a subassembly used in the adapter shown in FIG. 21.

The adapter 191 has a housing 197 in which a cannula subassembly 198 is mounted. The subassembly 198 (see FIG. 22) includes a plastic body 199 moulded in two halves 200,201, which when assembled together clamp a double-ended hollow needle or cannula 202 in place.

A device 190 is provided with a socket 203 for receiving the adapter 191. A cylindrical projection 204 on the end of the adapter 191 is designed to fit into the socket 203, and also to conceal the cannula 202 to prevent injury before and after the adapter 191 is mounted on the device 190. A self-sealing penetrable plug 205 mounted in the socket 203 leads to a conduit 206 and an inlet for the reservoir (see inlet 19 in FIG. 1). A subassembly 198 is mounted in a channel 207 of the adapter 191 such that it can be pushed inward until a shoulder 208 meets the end of the structure 209 defining the channel 207. At this point, the cannula 202 will penetrate the plug 205 enabling communication between the cannula 202 and the reservoir of device 190. In use, a cartridge 192 is pushed into the adapter 191, whereby a stopper 195 causes the subassembly 198 to be pushed inwards and the cannula 202 to penetrate the plug 205. Since the subassembly 198 can move no further inward, further pushing of the cartridge 192 into the adapter 191 causes cannula 202 to penetrate stopper 195, thus putting drugfilled space 196 in indirect communication with the reservoir of device 190.

The stopper 195 is then held by subassembly 198, further pushing of the cartridge 192 inwards causes the stopper 195 (which remains stationary) to move relative to the cartridge 192 (which is progressively accommodated in the interior of adapter 191), with a consequent emptying of the contents of the cartridge 192 through the cannula 202 into the reservoir of device 190.

Figure 23:
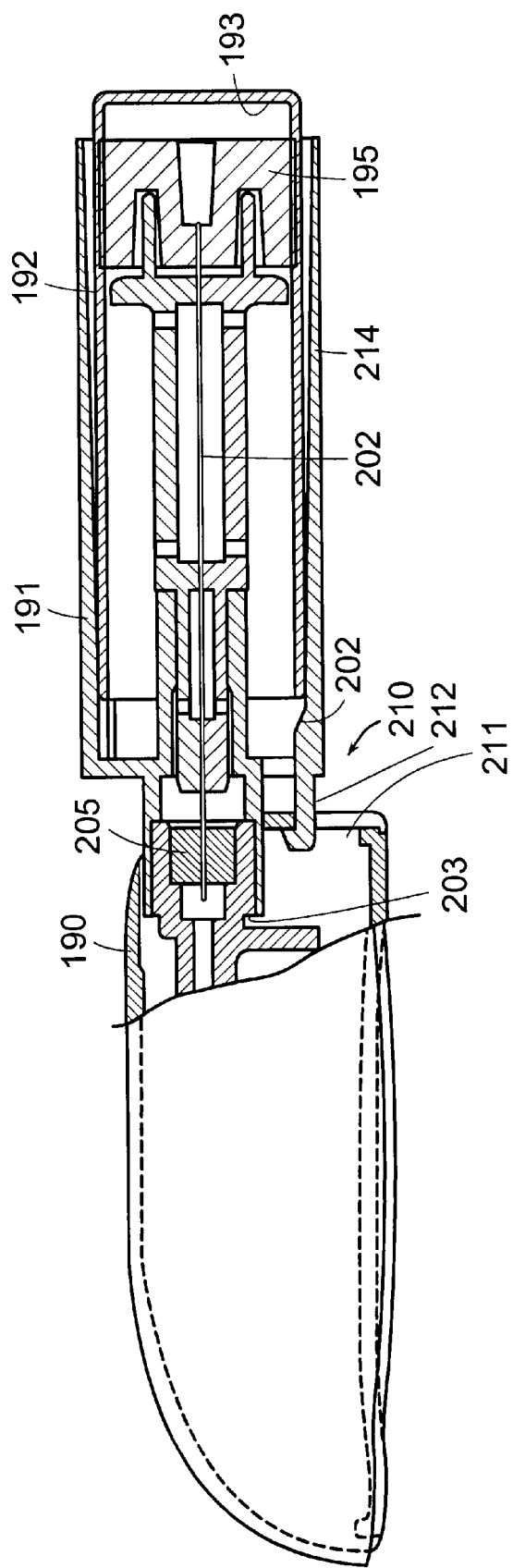
FIGS. 23 and 24 are sectional side views of the drug delivery kit of FIG. 21, shown during and after filling of the device, respectively.

This is illustrated best in FIG. 23, which shows a sectional view of the components shown in sectional plan view in FIG. 21, after the cartridge 192 has been pushed most of the way home into adapter 191. It can be seen that at this point, the stopper 195 (penetrated by cannula 202 which also penetrates plug 205) has almost reached the end 203 of cartridge 192.

The adapter 191 is not only held by the fit of the projection 204 into the socket 203, but also by a releasable locking mechanism 210. The releasable locking mechanism comprises 210 an aperture 211 on the device 190 and a resilient catch 212 on the adapter 191 which is biased into the position shown in FIG. 23 so as to hold the adapter firmly in place on device. Preferably the adapter 191 and the device 190 are sold together in kit form, optionally with the adapter already mounted on the device.

When the cartridge 192 is pushed fully home it acts on a sloped section 213 of wall 214 of adapter 191 so as to push resilient catch 212, which is an extension of wall 214, downwards. This disengages the locking mechanism 210, allowing the adapter 191 to be removed from the device 190.

Figure 24:
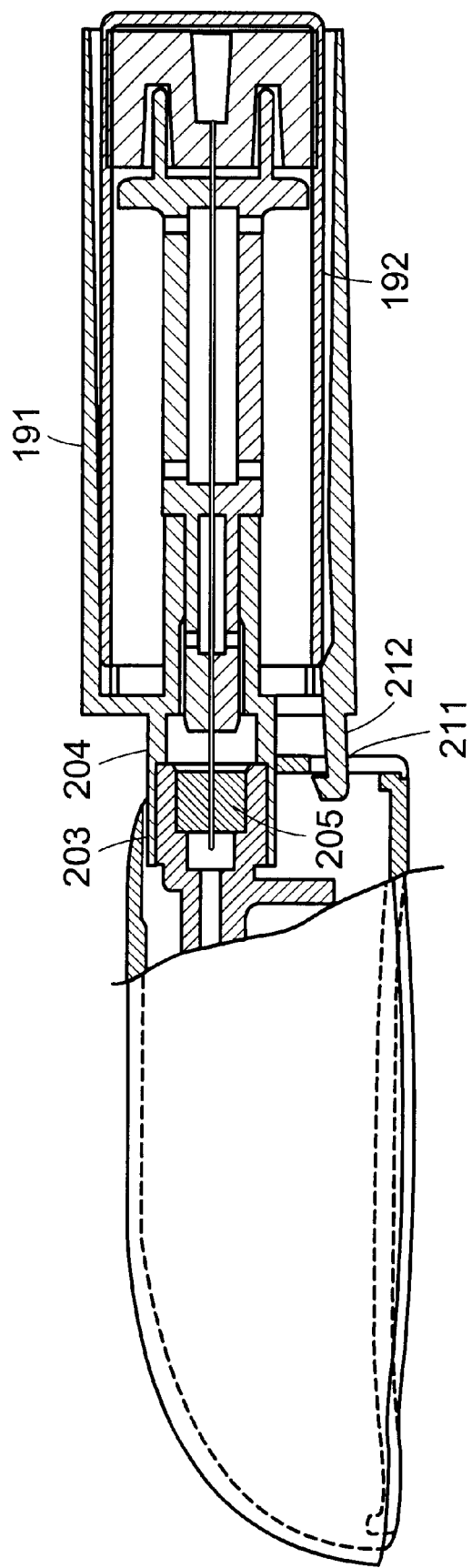

FIG. 24 shows the kit after the cartridge 192 has disengaged the catch 212 allowing it to be withdrawn from the aperture 211. This permits the adapter 191 to be removed from the device 190 by pulling the projection 204 from the socket 203 whereupon the plug 205 seals itself and thereby isolates the reservoir of the device.

Because the catch 212 is only disengaged when the cartridge 192 is fully emptied (i.e. when the stopper is pushed to the closed end 193 of the cartridge 192), one can ensure that the reservoir is loaded with exactly the correct amount of drug every time, thereby eliminating human error and making the kit more suitable for home administration.

Furthermore, because both ends of the cannula 202 at all times are concealed, the adapter 191 can be safely disposed of without risk of injury. The adapter 191 allows the drug to be transferred to the reservoir with sterility ensured, since the user does not at any time handle any of the components in the fluid path.

Figure 25:
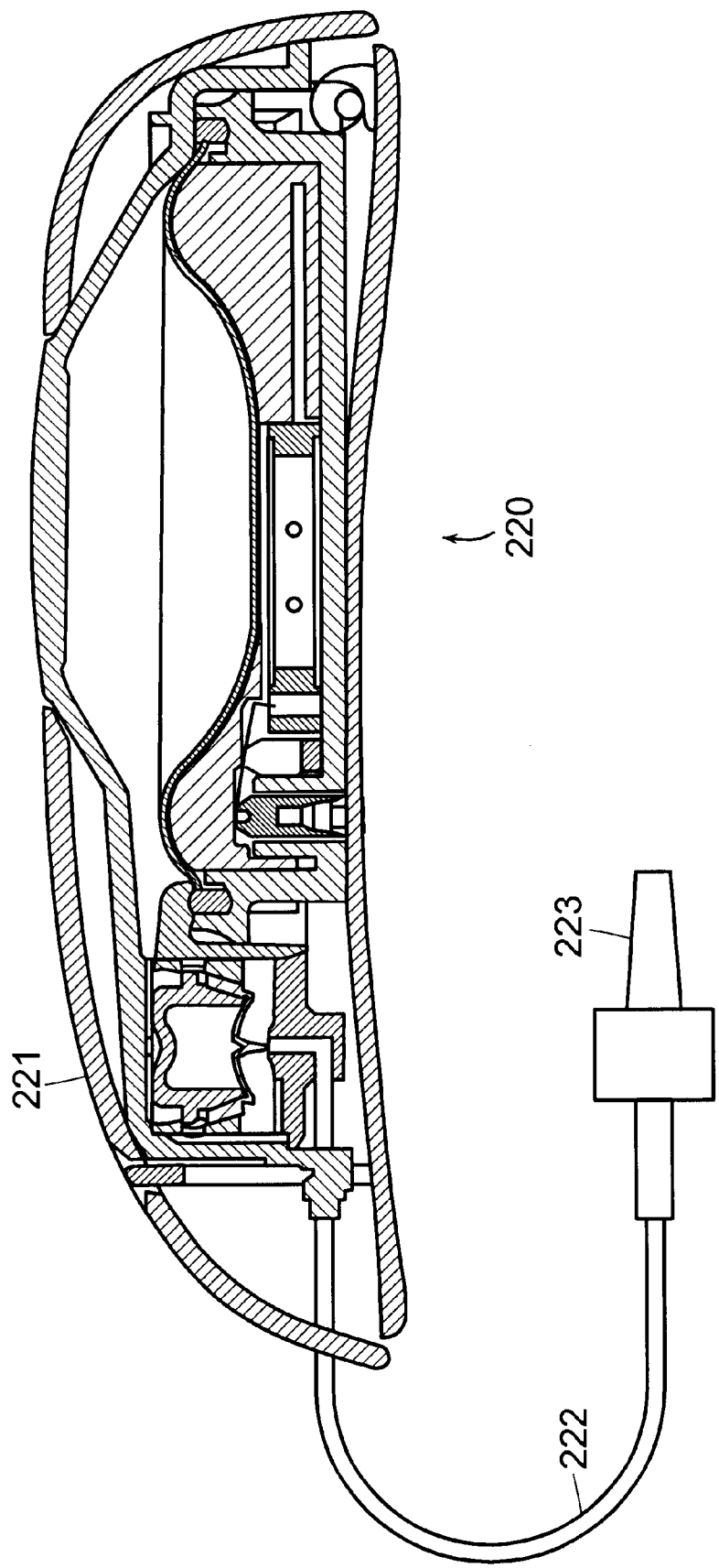
FIGS. 25 and 26 are sectional side views of fifth and sixth embodiments, respectively, of drug delivery device according to the invention.

FIG. 25 shows another alternative embodiment of the device according to the invention, indicated generally at 220. This embodiment differs from previous ones in that instead of a needle extending directly from the housing 221, a tube 222 extends from the housing 221 and carries a connector 223 thereon to which a needle may be affixed before use. This device 220 is particularly suitable for intravenous drug delivery because the tube 222 allows the needle to be accurately positioned in a vein.

Figure 26:
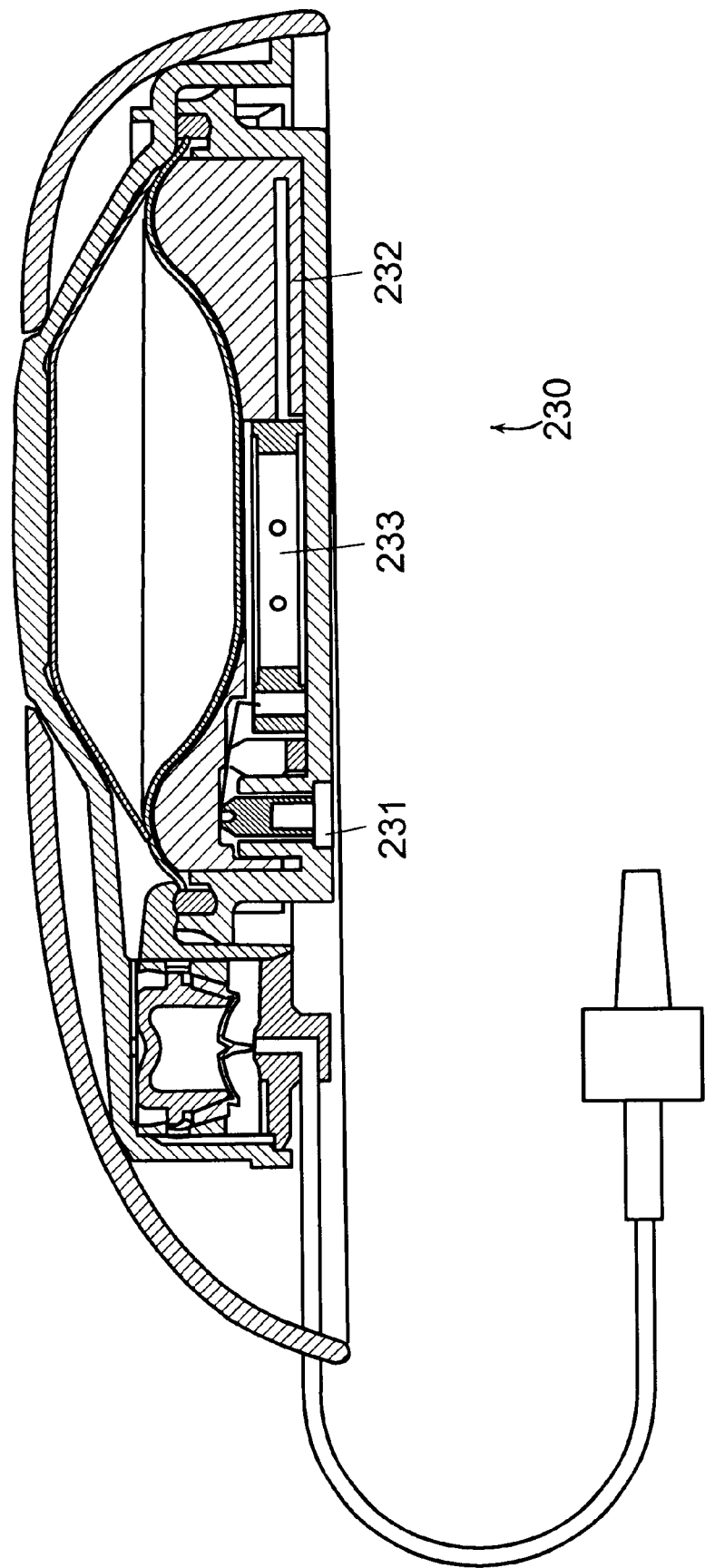

FIG. 26 shows an alternative intravenous embodiment, indicated generally at 230. In this embodiment the displaceable lower cover has been omitted and the device is actuated by a contact switch 231 positioned on the underside of the housing 232. When the device is applied to the skin, the switch 231 is pressed inwards (to the position shown in FIG. 26), thereby closing an electrical circuit and actuating a gas generating electrolytic cell 233 in the manner previously described. As the snap action provided by previously described devices is not required to cause a needle to penetrate the skin, the cover can be omitted without interfering with other functions of the device.

Figure 27:
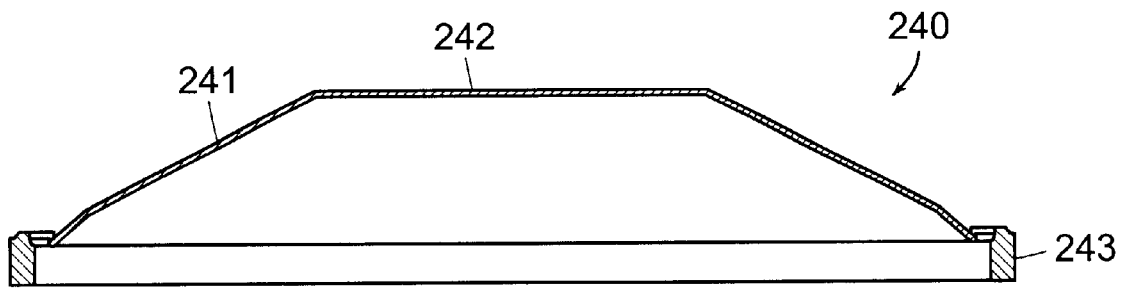
FIGS. 27 and 28 are sectional side views of a diaphragm suitable for use in a device according to the invention.

FIG. 27 shows the elastomeric diaphragm 240 utilized in the above-described devices according to the invention. The diaphragm 240 can also be used in other drug delivery devices according to the invention. The diaphragm 240 is shown in FIG. 27 in its relaxed position, as it would be when the reservoir is empty (see FIG. 6, for example). In this configuration the diaphragm 240 substantially has the form of a truncated cone having a sloped portion 241 surrounding a flat portion 242, with a lip 243 surrounding sloped portion 241 (lip 243 is used to attach diaphragm 240 to the housing of a drug delivery device).

Figure 28:
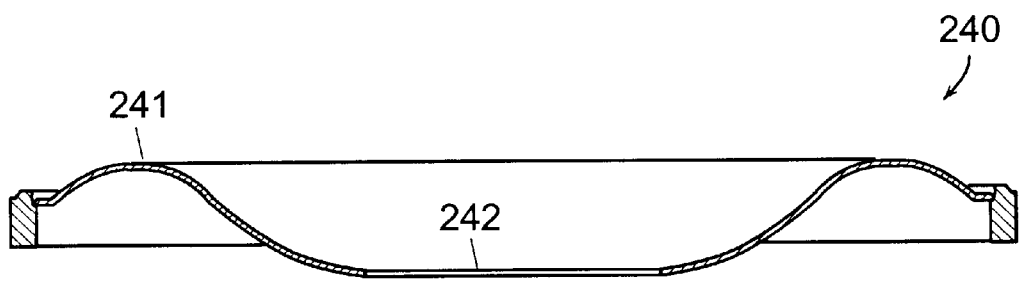

FIG. 28 shows the diaphragm 240 in the configuration in which the reservoir is full (see FIG. 1, for example). In this configuration, the central portion 242 is still flat, and the surrounding portion 241 has an arcuate curved cross-section, in the form of a substantially inverted U shape.

The diaphragm 240 is bistable, such that it is stable in either the FIG. 27 or the FIG. 28 configuration. However, a particular advantage has been found to result from the fact that in moving from the reservoir full (FIG. 28) configuration to the reservoir empty (FIG. 27) configuration, very little energy is needed.

Unlike many bistable arrangements, only minimal force is required to move between the stable configurations. In many bistable arrangements a substantial amount of energy is required to move from one configuration to a midpoint, at which the amount of stored energy is relatively high, following which the stored energy is released to complete the transition. The diaphragm 240, rather than flipping between configurations, makes a smooth transition. However, in contrast to a completely pliable body, which cannot be depended on to exert force uniformly, the diaphragm 240 will behave dependably since it is constrained in its movement between configurations. This means that a predictable manner of movement is combined with a minimal expenditure of energy in actually effecting the transition between bistable configurations.

The elastomeric diaphragm 240 (and others shown in alternative embodiments) and the flow diaphragm 26 of the flow regulating chamber 35 are elastomers. There are two preferred sources for this material. One is a bromobutyl compound made by Vernay Laboratories, Inc. of Yellow Springs, Ohio (material number: VL 911N7). The second is an ethyl propylene diene monomer ("EPDM") material number Bryant 850-55, made by Bryant Rubber.

There are several advantages in using these two materials. First, the material has a low durometer, which enables the material to remain soft. Moreover, it enables the diaphragm to keep air out and deflect from one stable position to the other with little energy. In addition, these elastomers provide a long shelf life. Another advantage is the ability to withstand gamma radiation without degradation of properties. As stated above, gamma radiation is used in some sterilization procedures. The ability of these materials to withstand gamma radiation is very important as these materials will be assembled in the device and sterilized. An additional advantage of using these materials is their lack of toxicity.

Figure 29:
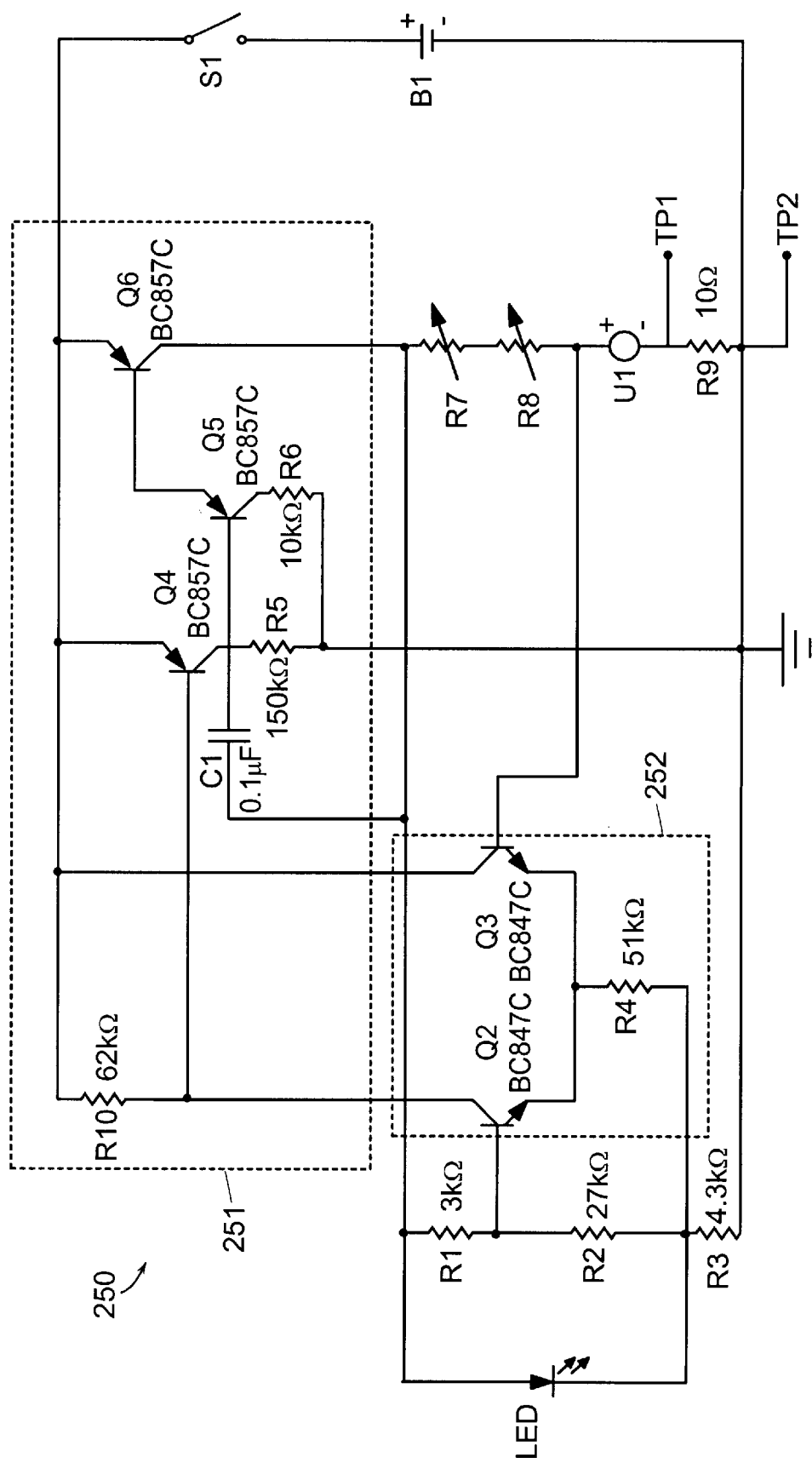
FIG. 29 is a diagram of an electronic controller circuit suitable for use in a device according to the invention.

FIG. 29 shows a circuit diagram of a controlling circuit particularly useful or a drug delivery device according to the invention. In the circuit 250, all symbols have their normal meanings within the art. The components shown are a battery B1, a switch S1 (activated by applying the device to the body), fixed resistors R1–R6 and R9–R10, variable resistors R7 and R8, a capacitor C1, transistors Q2–Q6, measurement terminals TP1 and TP2, a light emitting diode LED, and a load U1 which represents the electrolytic cell or other gas generating means. Reference numeral 251 denotes a section of the circuit 250 which functions as a current driver, and reference numeral 252 denotes a section of the circuit 250 which functions as an error circuit.

The current through the electrolytic cell U1 determines the potential drop across variable the resistance comprising resistors R7 and R8 (which may be adjusted to calibrate the device or set the delivery rate). This potential drop is compared by the error circuit with the potential drop across a reference resistor R1, which itself depends on the voltage drop across the LED. The value of resistor R1 is chosen to provide a potential drop equal to the drop measured across the resistors R7 and R8 when the correct current is flowing through the cell U1.

If the potential drop across the resistors R7 and R8 is lower than the constant potential measured across the resistor R1, indicating that the current through the cell U1 is too low (e.g. because of fading battery power, changes in the internal resistance of electrolytic cell U1 as the reactants are consumed, etc.), the error circuit 252 forces the driver 251 to increase the current flow to the correct value. In practice, the error circuit 252 continually ensures that the current does not deviate from the correct value by constant feedback operation.

Each of the transistors in the circuit 250 is a silicon-based bipolar transistor. The advantage of using bipolar transistors in particular is that they have been discovered to surprisingly withstand gamma radiation to a far greater extent than other types of transistors. The use of silicon as semiconductor is not essential but this material is currently less expensive than many other semiconductors. It has been found that by employing a circuit in which the or each transistor is a bipolar transistor, the circuit and hence the entire device can be subjected to intense gamma irradiation as a means of sterilizing the device after manufacture. Conventional integrated circuits are destroyed by the intense radiation required to sterilize a device quickly.

For example, a dose of 2.5 Mrad (25 kJ/kg) of gamma radiation may be required to sterilize a device. In trying to design a circuit which would withstand such harsh conditions we consulted data regarding the electronic components used in space missions, such as the U.S. Space Shuttle missions. It was found that the same degree of radiation resistance was not required because the absorbed dose measured on the Space Shuttle averages approximately 0.4–0.5 Mrad.

As a rule, all electronic components will undergo a degree of degradation when subjected to irradiation. However, by selecting components which are resistant to irradiation as far as possible and whose performance can be predicted after receiving a given dose of radiation, it is possible to design a circuit which will withstand intense gamma radiation and still function in a predictable manner.

In particular, by using a bipolar transistor with a high current gain (e.g. a current gain of at least 600 but preferably 800 or more) the drop in current gain exhibited after irradiation can be compensated for in advance. This drop in gain can be of the order of a tenfold drop or more, but can be predicted well in advance. Furthermore, by using current values which are sufficiently low, the drop in voltage at the silicon junction of the transistor occurring as a result of the irradiation only slightly affects performance.

A further advantage is gained using a circuit which employs a light emitting diode as a basis for the reference voltage used in the error correction circuit, since the LED reference source is not affected by the gamma radiation. The LED used is a gallium arsenide (GaAs) based LED which has been found to provide particularly good resistance to gamma radiation.

In summary, the components and circuit employed have been found to be suitable for gamma irradiation, following which they give a well predictable performance in use. This enables the manufacture to be completed more efficiently, with the assembled device sterilizable by gamma radiation.

Figure 30:
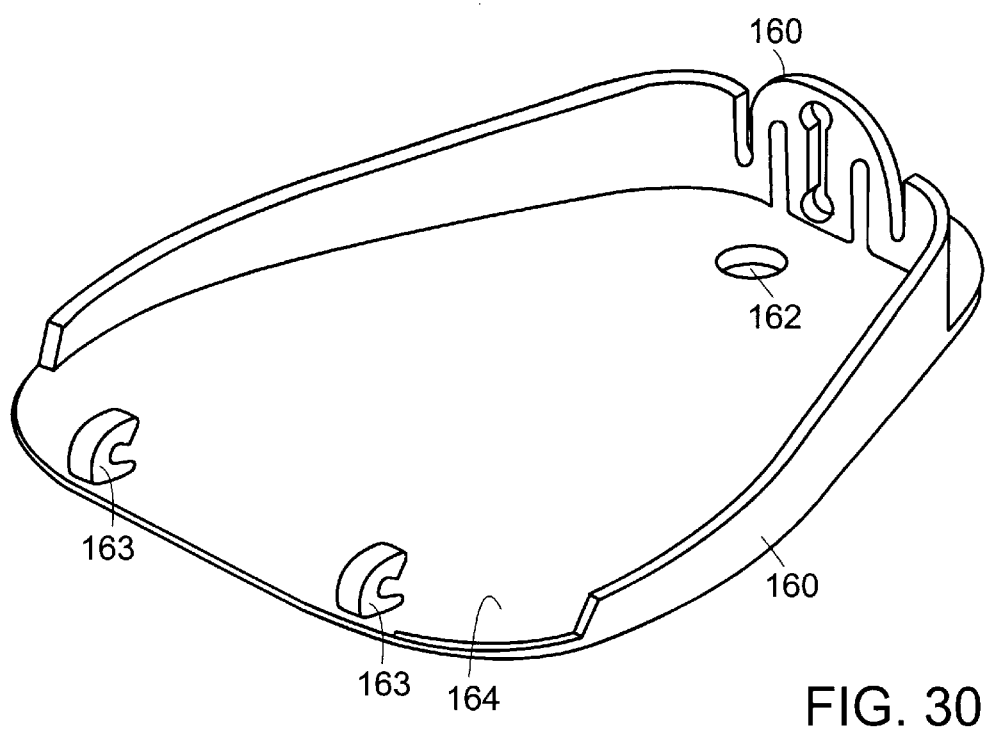
FIGS. 30 and 31 are perspective views of the top side and underside, respectively, of a displaceable cover from a device according to the invention.
Figure 31:
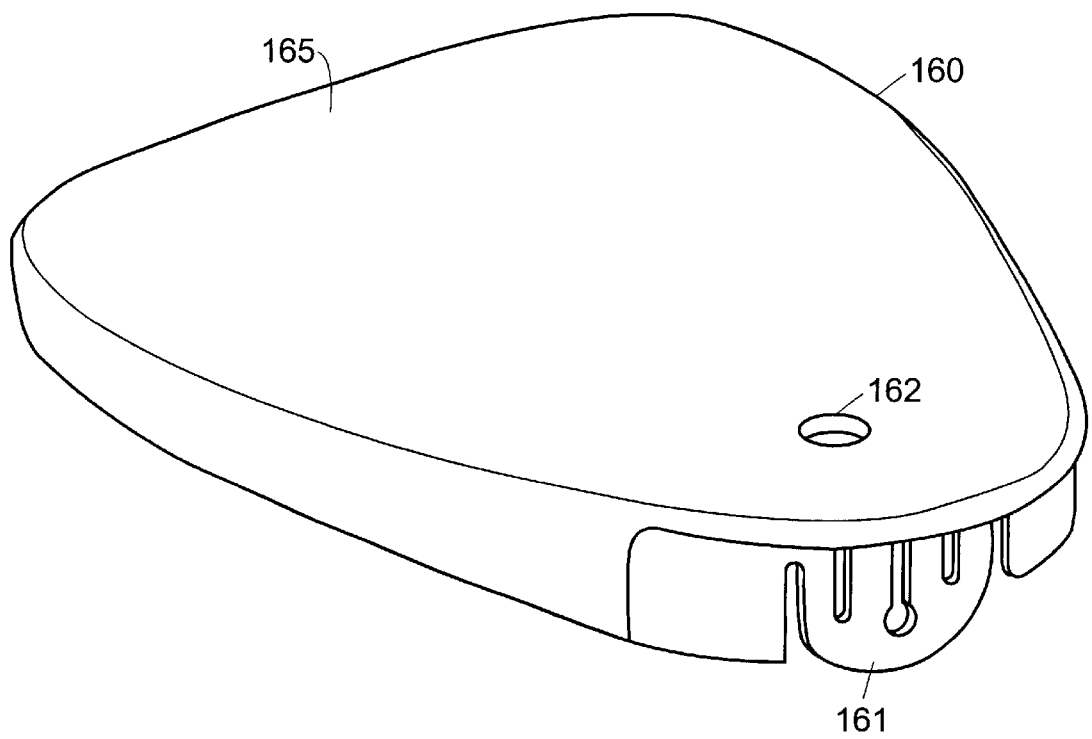

FIG. 30 is a perspective view of the top side of a displaceable cover 160 forming part of a device according to the invention. FIG. 31 is a perspective view of the underside of cover 160. Such a cover is described generally above in relation to the embodiment of FIGS. 4–8, for example.

The cover 160 is provided with formations 161 forming part of a locking mechanism as described above, with an aperture 162 through which a delivery needle protrudes in use. The cover 160 also has hinge formations 163 which enable the cover to be displaced relative to the housing between first and second positions as previously described.

The cover 160 is shaped to improve retention of the device against the skin: thus the top side 164 (FIG. 30) is convex, and the underside 165 (FIG. 31) from which the needle protrudes in use is concave. Accordingly, when the device has been applied to the skin of a subject removal of the device is resisted because the cover 160 conforms more closely to the skin. It is less likely that the device will peel from the skin without a conscious effort by the user since there is a lower likelihood of the periphery of the cover being detached from the skin.

Figure 32A:
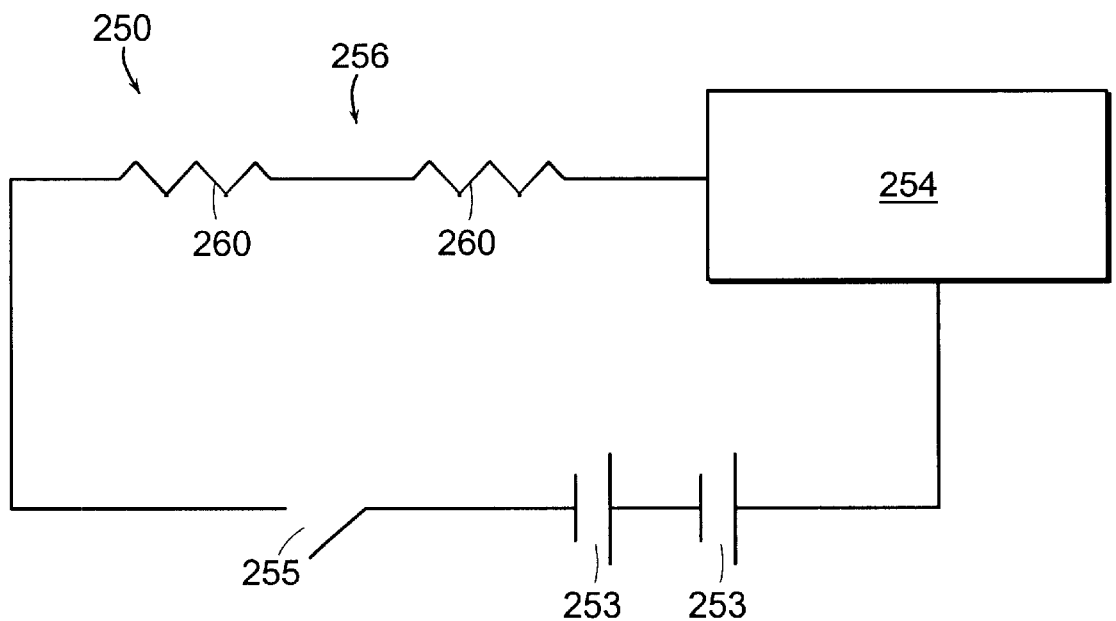
FIG. 32A schematically illustrates a preferred embodiment of an electrical circuit for an electrolytic cell in a drug delivery device in accordance with the present invention.

FIG. 32A schematically illustrates an alternative preferred embodiment of an electrical circuit 250 within a subcutaneous drug delivery device. The circuit 250 replaces the entire circuitry of FIG. 29. In order to provide a constant rate of drug delivery, the delivery system 254 requires a constant current. This electrical circuit stabilizes the current supplied to the electrolytic cell without using components such as transistors which are sensitive to gamma radiation during sterilization. Gamma radiation is a standard method of sterilization of medical devices. A constant current supplied to the electrolytic cell results in a volume of gas which provides a desired constant delivery rate. The circuit uses a higher voltage than the previous embodiments along with current stabilizing resistive elements, such as, for example, resistors in series. FIG. 32A shows an electrical circuit 250 having a pair of batteries 253 coupled to a drug delivery system 254 by a current stabilizer 256. The batteries 253 in the electrical circuit 250 can include, for example, but is not limited to, between one and three batteries, having voltages of, for example, 1.5 or 3V. FIG. 32A illustrates an embodiment having two batteries 253. The current stabilizer 256 can calibrate the electrical circuit 250 to provide an appropriate current for the subcutaneous drug delivery device. The electrical circuit 250 can also include a switch 255.

Figure 32B:
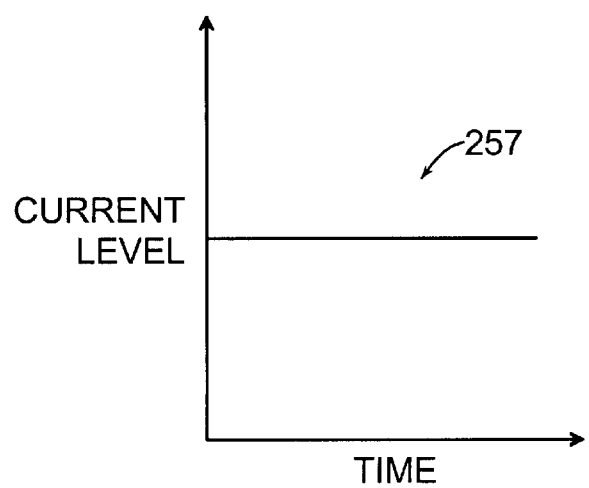
FIG. 32B graphically illustrates the current profile of the electrolytic cell shown in FIG. 32A in accordance with the present invention.

In the alternative embodiment described in the preceding paragraph, the current stabilizer 256 can use a single resistor or alternatively as shown in FIG. 32A, the current stabilizer 256 includes two resistors 260 connected in series. In a preferred embodiment, the two resistors 260 have identical resistance values. The use of multiple resistors 260 can reduce the current charge as a result of accidental short circuiting of a resistor. The maximal delivery rate of the delivery system 254 with a short circuit condition at one resistor can only be twice the nominal rate. A change of battery voltage and a change of resistance of the electrical circuit 250 can change the current profile at the circuit 250. In one embodiment, it is possible to control the current profile by selecting the voltage and number of batteries used in the circuit 250. In a preferred embodiment, the current profile 257 is constant over time, as illustrated in FIG. 32B.

The subcutaneous drug delivery device can also include an occlusion prevention mechanism. FIGS. 33A–33F schematically illustrate a drug delivery system in which an undesired delivery of a bolus of a medicament can occur. FIG. 33A schematically shows a delivery device 262 having a gas chamber 264, a drug chamber 266, a flexible diaphragm 265, and a needle 270. There is a lower risk of bolus delivery if the back pressure in the gas chamber 264 is constant. The gas is produced at a constant rate by the gas generator. As the gas is produced, the drug within the drug chamber can flow constantly to keep equal pressure within the device 262. FIG. 33B shows the linear relationship of drug delivery over time.

FIG. 33C shows an occlusion 268 occurring in needle 270 of the delivery device 262. Once occluded, the pressure in the gas chamber 264 will rise as the gas generator continues to produce gas and the drug within the drug chamber 266 does not flow. FIG. 33D illustrates that an occlusion can result in the reduction or termination of delivery of the drug over time. The pressure in the gas chamber 264 can reach a high enough level to overcome and remove the occlusion. Once the occlusion is removed, the drug within the drug chamber 264 can flow rapidly until back pressure in the gas chamber 264 and the pressure in the drug chamber 266 equalize, therein creating a bolus delivery of the drug.

FIGS. 33E and 33F illustrate the relationship between drug delivery and time, as the occlusion is removed and the pressures equilibrate. The size of the bolus can depend on the time duration of the occlusion and the nominal flow rate without the occlusion (Volume bolus=Time occlusion*Flow rate). The occlusion time duration depends upon the gas generation rate and the volume of the gas within the gas chamber 264. The longer the time the subcutaneous drug delivery device worked before the occlusion, the bigger the volume of the gas in the chamber 264, the longer the time needed to rise to the pressure to remove the occlusion 268, the larger the bolus. FIG. 33F shows a graphical representation of the rapid flow of a drug delivery system as an occlusion is removed from a needle and the pressure equalizes.

FIG. 34A shows a bolus prevention mechanism 272 within a drug delivery device 262 created by forming a constant, relatively high pressure level in the drug reservoir. In a preferred embodiment, the mechanism 272 is a valve 274. The use of a valve 274 can create a constant high pressure 276 within the gas chamber 264, while maintaining a low pressure 278 within the needle 270 of the delivery device 262. The high back pressure 276 and the low pressure 278 within the needle 270 can prevent occlusions from clogging the delivery device 262 for lengthy periods of time, therefore minimizing or preferably preventing the formation and delivery of boli. As long as the high back pressure 276 is higher than the pressure needed to deliver the drugs subcutaneously, the flow of the drug will not be adversely affected. FIG. 34B shows a graphical representation of the steady delivery of drugs over time created by the use of a bolus prevention mechanism within the drug delivery device of the present invention.

Figure 36A:
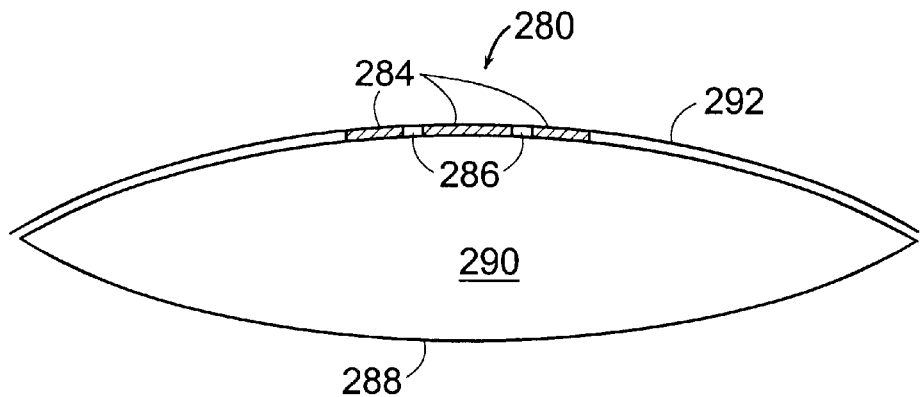
FIGS. 36A–36C schematically illustrate the changes in the drug reservoir of a drug delivery device in accordance with the present invention.
Figure 36B:
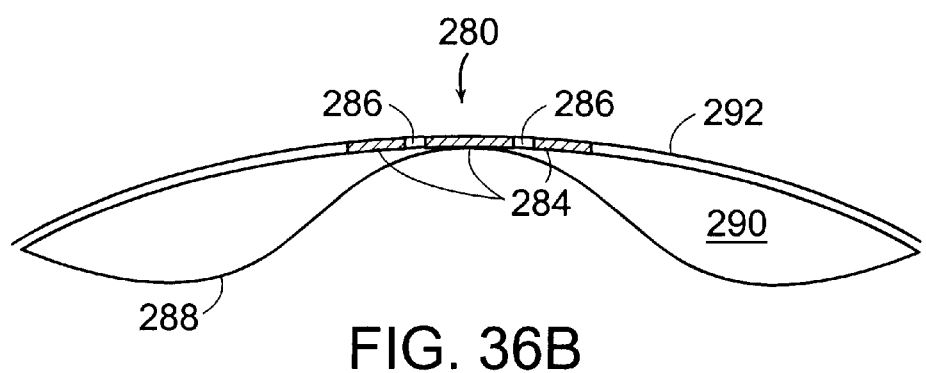
Figure 36C:
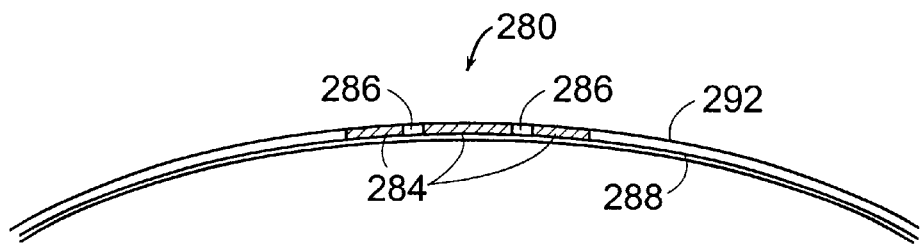

A preferred embodiment of the subcutaneous drug delivery device 282 can also include an optical window 280, shown in FIG. 35, which indicates to a user when delivery of a drug contained within the device 282 is complete. The drug is typically contained between the plastic housing and the elastomeric membrane or diaphragm that moves away from the housing as the drug fills the reservoir. When the drug delivery device does not contain the drug, the elastomeric membrane is proximate to the housing. The optical window 280 is located on the housing. When the membrane is proximate to the housing, the optical effect of the direct reflection of light from the elastomeric membrane results in clearly visible membrane color, for example, blue. However, when the reservoir is full, the light is diffused in the drug chamber results in the appearance of the black color. In a preferred embodiment, the optical window 280 is a circular structure which allows light to enter and includes a pair of opaque sections 284 matching the membrane color and a transparent annular ring section 286 which allows the light to enter. The ring-like structure provides a more accurate assessment of the quantity of drug delivered. FIGS. 36A–36C show changes to the optical path through the window during drug delivery which indicate to a user the amount of fluid in the reservoir of the drug delivery device.

FIG. 36A illustrates a drug reservoir 290 bounded by a diaphragm 288 and a reservoir housing element 292. The reservoir housing element 292 has the drug window 280 which includes both the opaque section 284 and the transparent section 286. In a preferred embodiment, the color of the colored section 284 and the diaphragm 288 are the same, for example, both the colored section 284 and the diaphragm 288 are light blue in color. At the onset of drug delivery, the drug reservoir 290 can be full of a medication to be delivered to a patient. When the reservoir 290 is full, the transparent section 286 of the optical window 280 appears as a different color to that of the colored section 284 and the diaphragm 288. In one embodiment, the transparent section 286 will appear as black.

FIG. 36B illustrates a drug reservoir 290 after drug delivery has been partially completed. At this stage of drug delivery, the diaphragm 288 can partially contact the optical window 280 and can block a portion of the transparent section 286. Such a blockage optically changes the appearance of a portion of the transparent section 286, that is, instead of appearing black, it appears as the same color as the colored section 284. Such a change in color indicates to a user that drug delivery is partially completed.

FIG. 36C illustrates a drug reservoir 290 after drug delivery has been completed. At this stage of drug delivery, the diaphragm 288 can completely contact the optical window 280 and can block the entire transparent section 286. The contact of the diaphragm 288 against the transparent section 286 can optically change the appearance of the color of the transparent section 286, that is, instead of appearing black, the diaphragm becomes visible. A complete change in color of the transparent section 286 can indicate to a user the end of drug delivery.

In another preferred embodiment, the drug delivery system can include an optical indicator to indicate proper application and operation to a user. The indicator can be, for example, a color marking system. The color marking system can be used to indicate to a user components of the drug delivery system which should be removed from the system prior to use. The color marking system can also indicate to the user whether or not the drug delivery system has been applied correctly or is operational. In a preferred embodiment, the color marking is, for example, yellow in color. The color marking can be applied directly to components of the drug delivery system or can be applied in the form of a colored label.

In one embodiment, the filling adaptor or syringe adaptor of the subcutaneous drug delivery device can have yellow labeling attached thereon to indicate to a user that the adaptor should be removed before activating the delivery device. In another embodiment, the base of the delivery device can be produces (for example, dye in the plastic) with a color which contrasts with the color of the cover. During use, the cover of the delivery device can be hingedly moved towards the base and covers all but a small portion at the base. The disappearance of the contrastingly colored base can indicate to a user that the drug delivery device has been correctly applied and activated. Generally, when the drug delivery device is correctly applied and started, none of the parts of the device, which include color marking or color labeling, can be visible to the user.

Figure 37A:
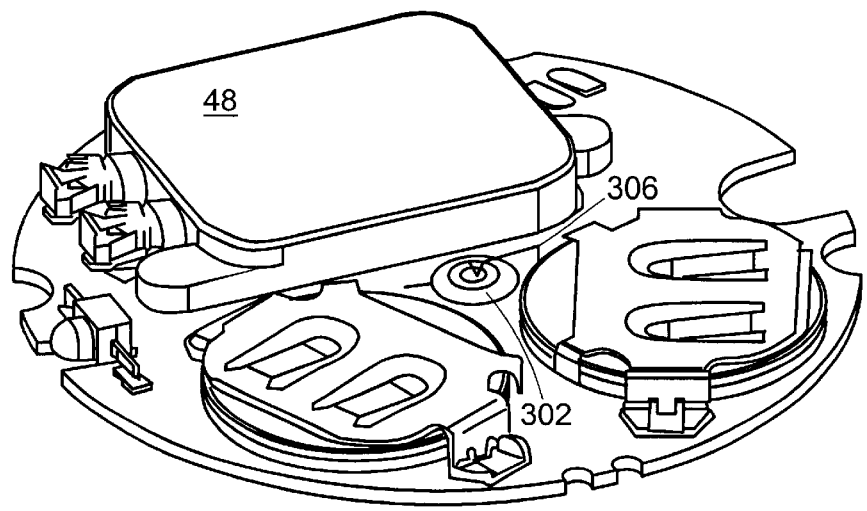
FIG. 37A is a perspective view of a printed circuit board with a pressure sensitive mechanism.

In another preferred embodiment, the subcutaneous drug delivery device can include a pressure sensitive mechanism, such as in FIG. 37A, for preventing bolus delivery or rapid injection of a drug into the user. A switch 300 can prevent a rapid injection of drug to a user as a result of an increase in pressure in the drug delivery device. The switch 300 can help to avoid an increase in pressure within the drug delivery device caused by blockage of the needle. The switch 300 can form part of a circuit 250, as shown in FIG. 32A, which controls the power supply to a gas generating portion of the drug delivery device.

Figure 37D:
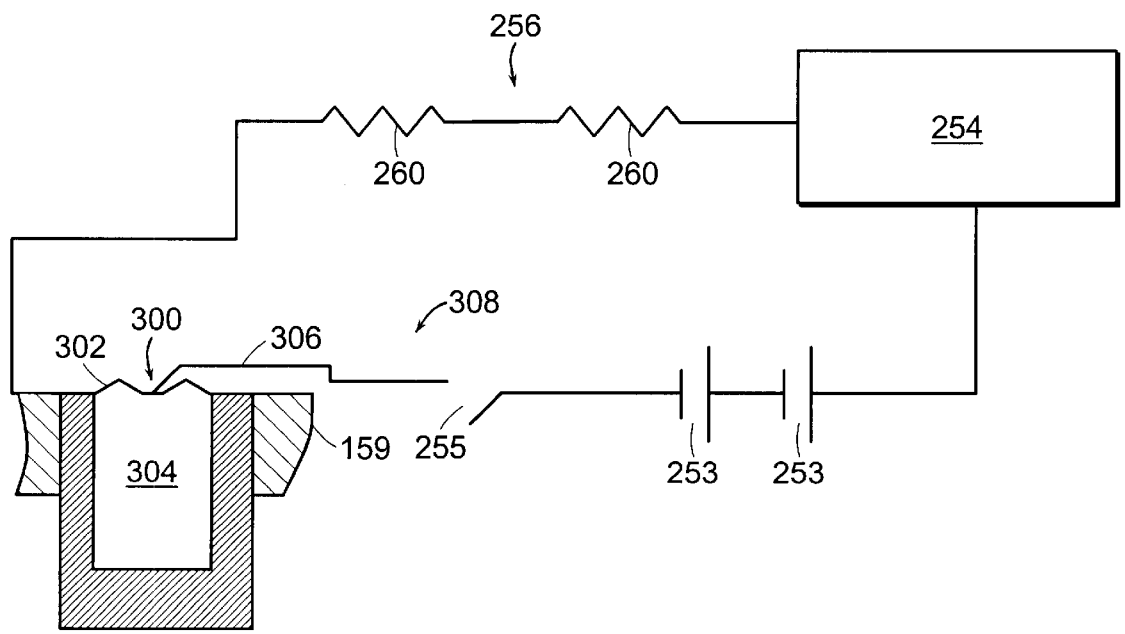
FIG. 37D is a schematic illustration of an electrical circuit for the drug delivery system incorporating elements of FIG. 32A and FIG. 37A.
Figure 37B:
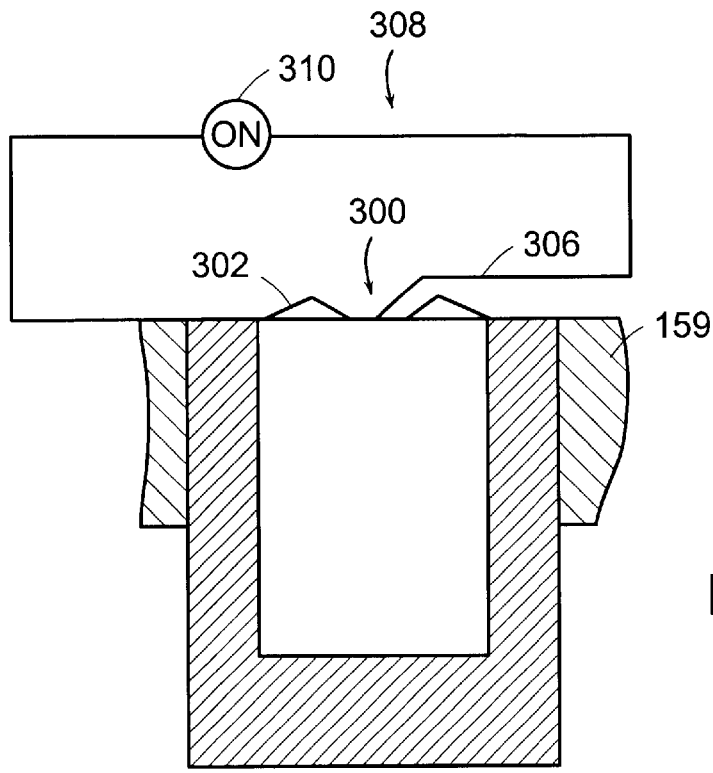
FIGS. 37B and 37C schematically illustrate a preferred embodiment of a pressure sensitive mechanism of FIG. 37A included in a drug delivery device in accordance with the present invention.
Figure 37C:
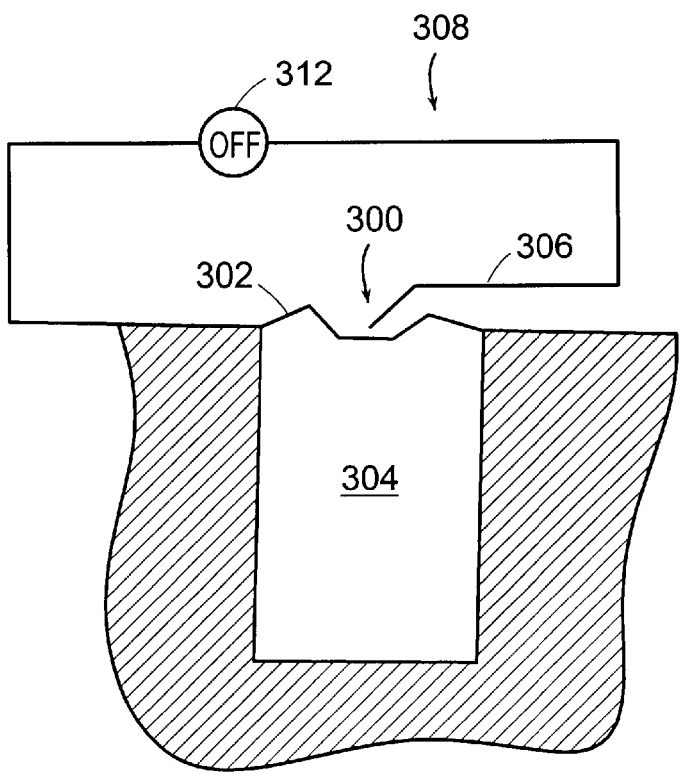

One embodiment of the switch 300 is shown in FIGS. 37A–37C. In this embodiment, the switch 300, which is part of a circuit 308, is made from a conductive membrane 302 and a conductive lever 306 is located on the printed circuit board 159, as seen in FIG. 37A. The switch 300 has a chamber 304 which is sealed by the conductive membrane 302 as seen in FIGS. 37B and 37C. The chamber 304 contains an accurate amount of gas, such as, for example, air, and can be made of a solid material whose volume is not affected by pressure and is non conductive electrically, referred to as a solid isolator. The membrane 302 has a raised annular portion to allow the membrane to flex depending on the pressure differential between the chamber 304 and the expandable chamber 14. The lever 306 is designed to rest upon the membrane 302 during operation. When the conductive lever 306 contacts the conductive membrane 302, the circuit 308 can be closed, thereby allowing the gas generating portion of the device to operate 310. As long as the pressure within the gas generating portion of the delivery system is lower than the pressure within the chamber 304, the lever 306 can contact the membrane 302.

In the event that the pressure within the drug reservoir increases, such as caused by a blockage in the needle, the pressure within the gas generating portion can increase to a higher level than the pressure within the chamber 304. In the event pressure within the drug reservoir and the expandable chamber 14 increases, the pressure within the chamber 304 is lower relative to the expandable chamber 14 and the membrane 302 is pushed away from contact with the lever 306, as shown in FIG. 37B. As a result, the lever 306 is no longer in electrical contact with the membrane 304 and the circuit opens, thus shutting off power to the gas generating portion of the device. This, in turn, stops any pressure build-up and potential for a boli delivery. The conductive membrane or lever can be made from aluminum or copper, for example.

FIG. 37D illustrates circuit 308 as part of circuit 256 which was shown in FIG. 32A. The switch 300 is in series with switch 255. Both switches 255 and 300 must be closed to generate gas. Switch 300 is normally closed and switch 255 is closed to start the gas generation. As indicated above, switch 300 only opens if the pressure increases to a current level, such as due to a blockage.

Figure 38A:
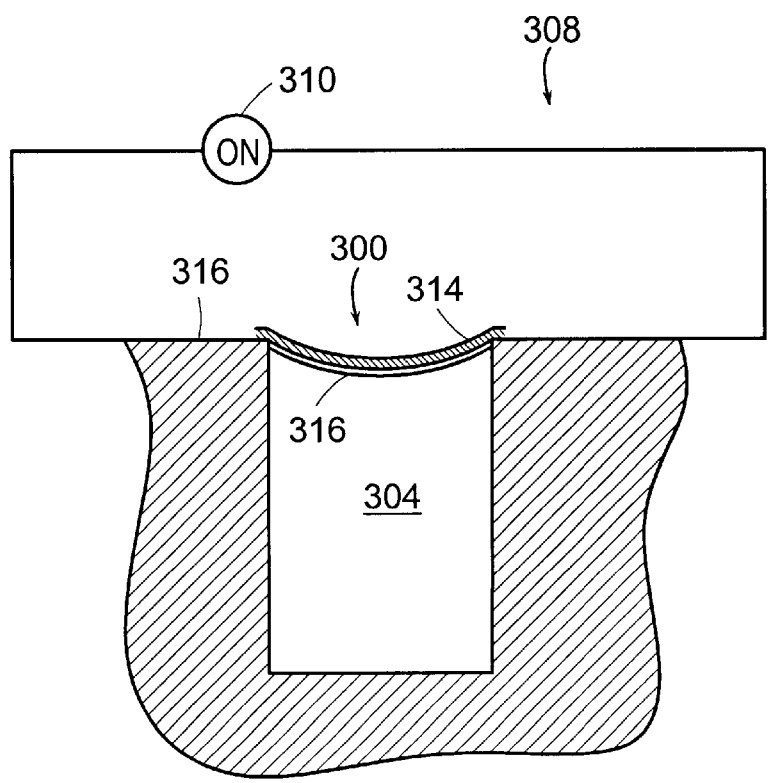
FIGS. 38A and 38B schematically illustrate another preferred embodiment of a pressure sensitive mechanism included in a drug delivery device in accordance with the present invention.
Figure 38B:
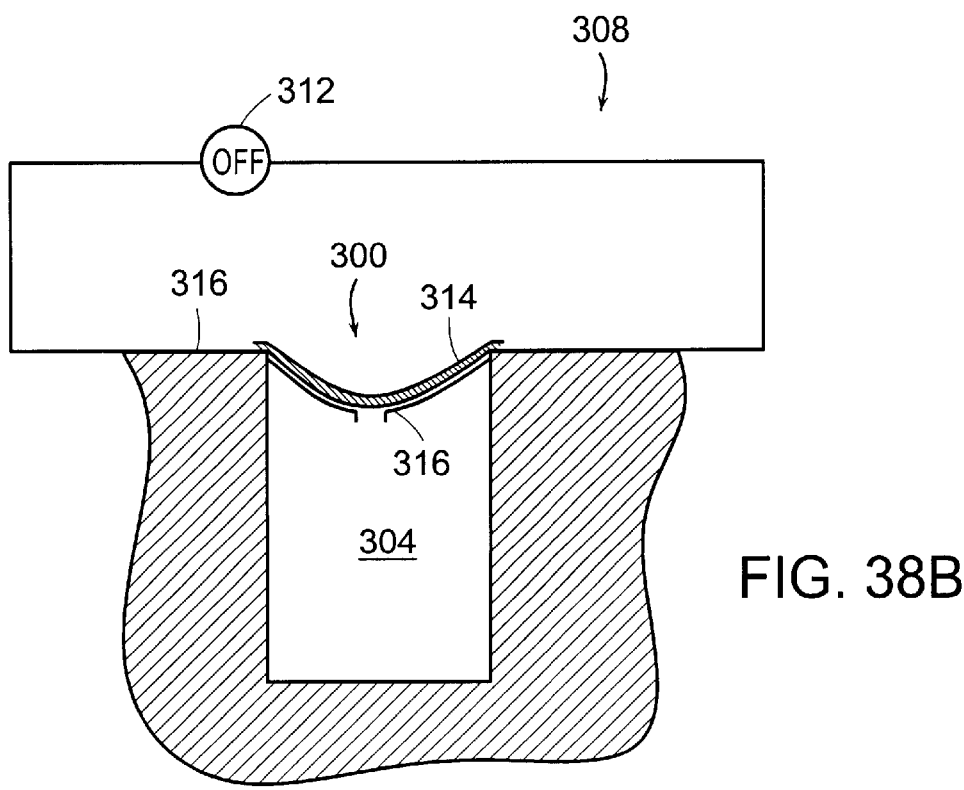

FIGS. 38A and 38B illustrate an alternative embodiment of a pressure sensitive mechanism 300. In this embodiment, the switch 300 includes an isolator membrane 314, mounted above a chamber 304, and a conductive thread 316 combined with the membrane 314. As long as the pressure within the gas generating portion is lower than the pressure within the chamber 304, the thread will remain intact, thereby completing the circuit for the gas generator, which remains in an on position 310. In the event of an increase in pressure in the drug reservoir, as shown in FIG. 38B, the gas generating portion can increase to a higher level than the pressure within the chamber 304. The pressure differential can cause the membrane 314 to sink into the chamber 304, thereby severing the thread 316. Such a break can open the circuit 308, thereby preventing the gas generator from producing gas 312 and preventing an increase in pressure in the drug reservoir. In contrast to the previous embodiment, once the circuit is open the circuit cannot be closed again, i.e. once the membrane is depressed the thread is severed.

Figure 39A:
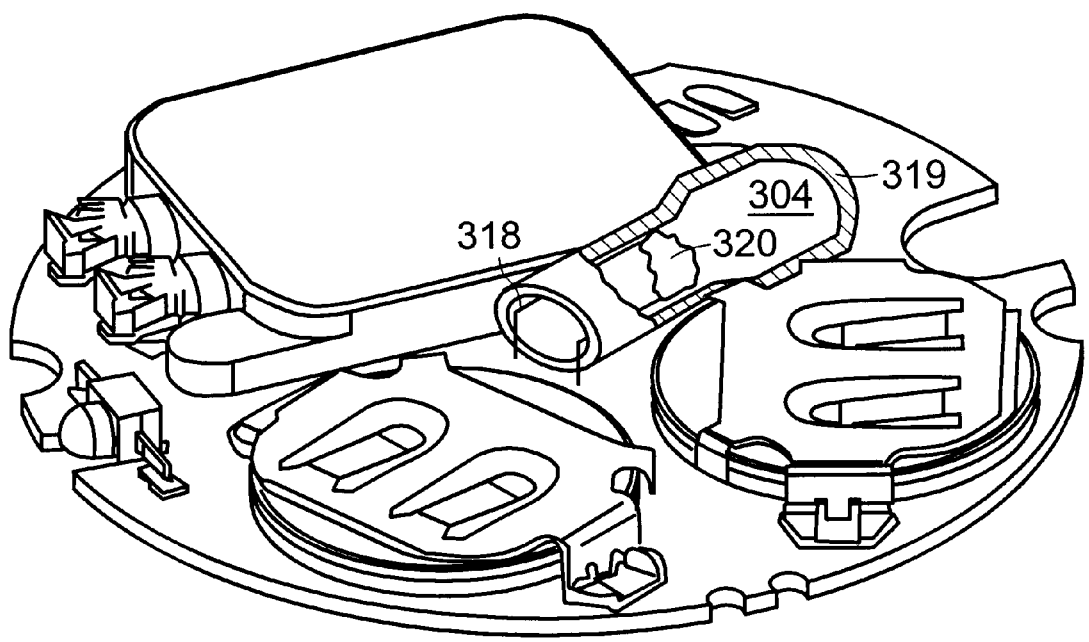
FIG. 39A is a perspective view of a pressure sensitive mechanism, with portions broken away on a printed circuit board.
Figure 39B:
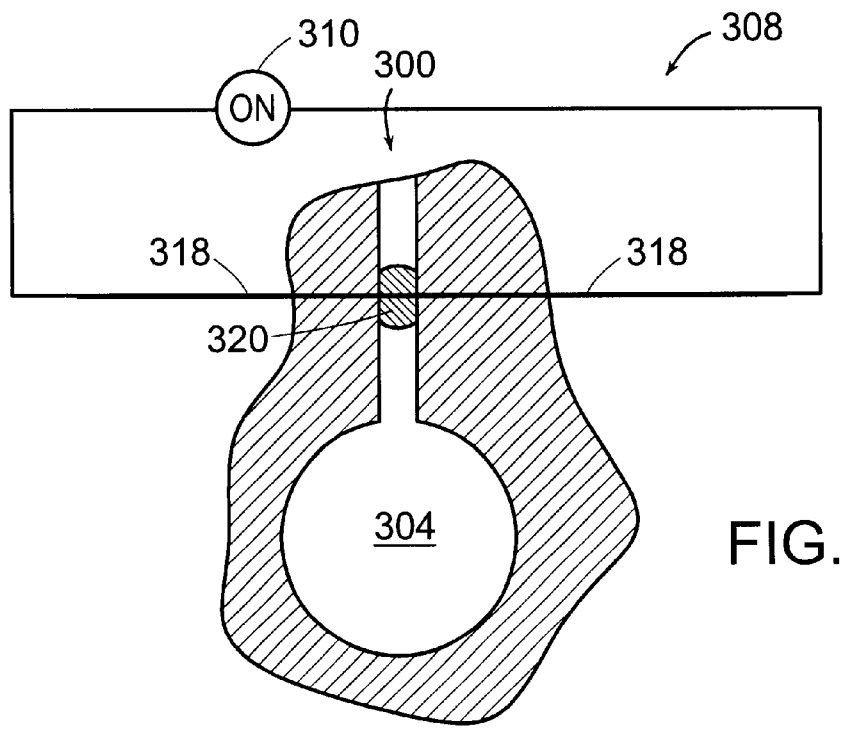
FIGS. 39B and 39C schematically illustrate the preferred embodiment of a pressure sensitive mechanism of FIG. 39A included in a drug delivery device in accordance with the present invention.
Figure 39C:
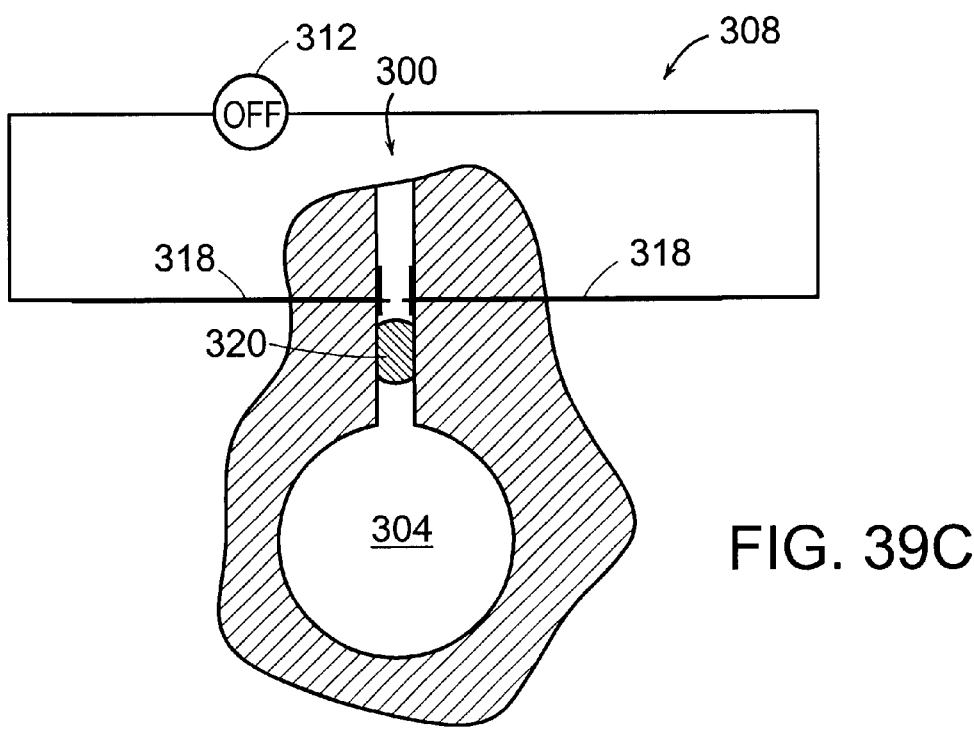

FIGS. 39A–39C illustrate another preferred embodiment of a pressure sensitive switch 300. FIG. 39A is an enlarged perspective view of the switch 300 with portions broken away. FIGS. 39B and 39C are schematics of the switch 300. In this embodiment, the switch 300 is formed from a pair of electrodes 318, extending into a capsule 319. Each electrode 318 connected to the circuit 308 contacts a droplet of mercury 320 located in a channel which opens onto a large chamber 304. The droplet 320 of mercury maintains the current between contacts as long as the pressure in the gas generating portion is less than the pressure within the chamber 304. Such a contact can close the circuit 308, thereby allowing the gas generator to operate 310. Under a high enough pressure in the drug reservoir, as shown in FIG. 39B, the pressure in the chamber 304 can be lower than the pressure within the gas generating portion of the delivery device, thereby causing the mercury droplet 320 to move towards the chamber 304 and away from the electrodes 318. The mercury droplet responds to the relative pressure between the gas generating portion and the chamber 304. Such a movement opens the circuit 308, thereby preventing the gas generator from producing gas and increasing the pressure in the drug reservoir.

While both the first embodiment, FIGS. 37A–37D, and the third embodiment, FIGS. 39A–39C, have the capability to have the switch 300 closed again if the pressure equalizes, it is contemplated that the pressure will not decrease and therefore once the switch is open, it will remain open and the power to the gas generator will not be restored.

Another preferred embodiment of the subcutaneous drug delivery system includes a mechanism which reduces tolerances and thus errors during manufacture of the device. During manufacture, certain components need to have a particular tolerance. When the device is assembled, if the tolerances of each component are significant, the volume of the internal housing may be outside of a specified desired range. Thus, an insert, for example, a foam insert that receives the internal components of the device, maintains an accurate internal volume so that upon assembly, the volume of the internal housing, and thus, the drug reservoir is within an accurate range.

Figure 40:
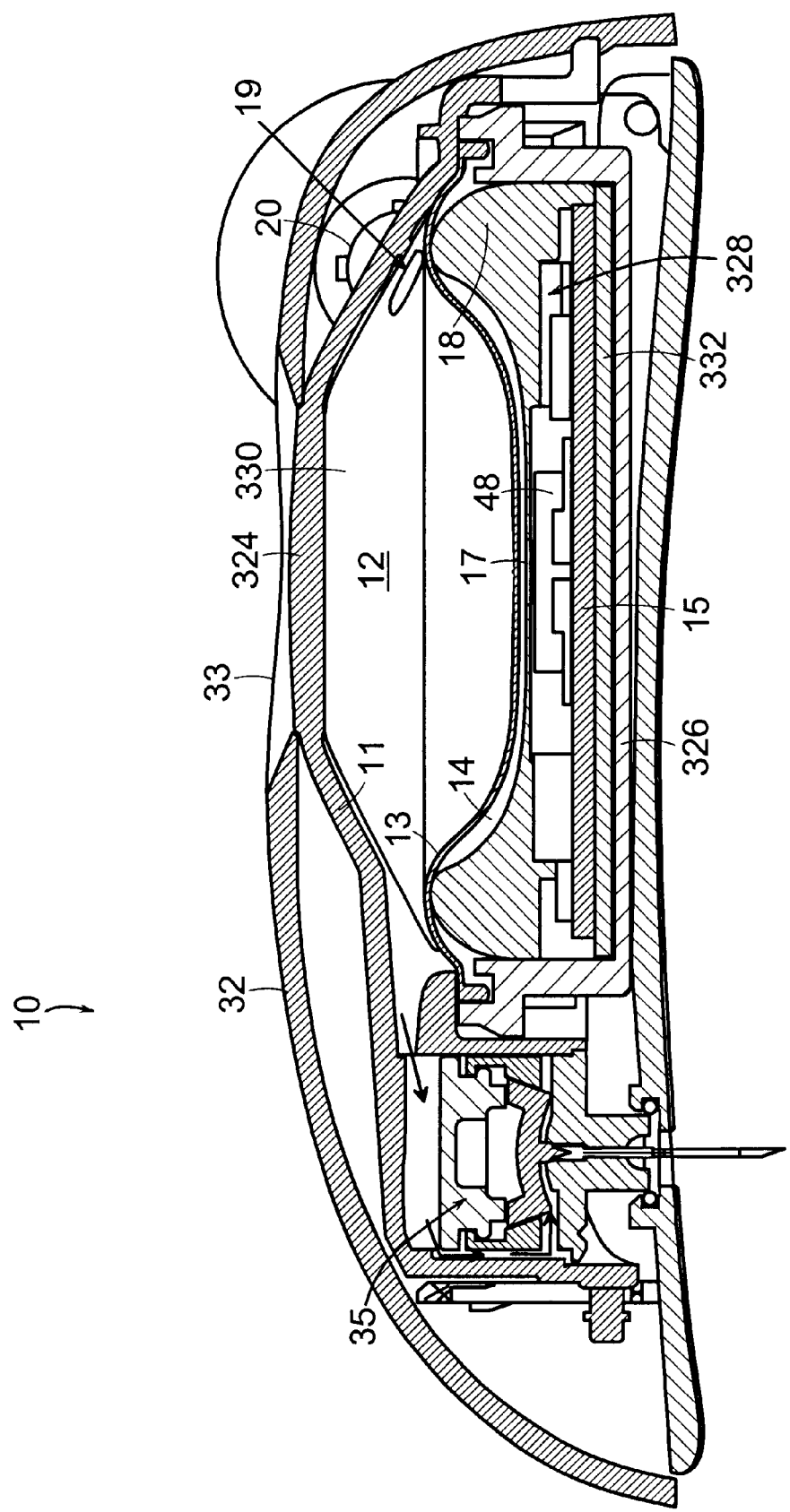
FIG. 40 schematically illustrates a preferred embodiment of a drug delivery device including an insert in accordance with the present invention.

A subcutaneous drug delivery device 322 is shown in FIG. 40. The device 322 can have a cover 324 and a base 326 and can house an inner component 328. The device 322 can also have an internal volume 330 between the cover 324 and the inner component 328. During manufacture of the device, the base 326, cover 324, and inner components 328 need to be manufactured within certain tolerances. Due to the tolerances of the components, the internal volume 330 can be outside of a specific range. To eliminate any variability due to tolerances, an insert 332 can be used to maintain the precise drug reservoir 12 necessary within the device 322. The insert 332 forces the inner component 328 toward the cover 324 of the delivery device 322. This eliminates assembly tolerance errors during manufacturing and can get the internal volume 330 of the device 322 within an accurate and acceptable range. The internal air volume 330 includes the internal chamber which defines the reservoir 12 and the expandable chamber 14, and air volume between components and below the expandable chamber 14, which is referred to as a dead air volume. Dead air can also be defined as residual air below the diaphragm after the primming. In one embodiment, the insert 332 is a flexible material. In a preferred embodiment, the insert 332 is closed foam; the air pockets or bubbles are sealed so not forming a part of the dead air. The internal volume 330 of the device 322 can be used as a drug reservoir.

Figure 41A:
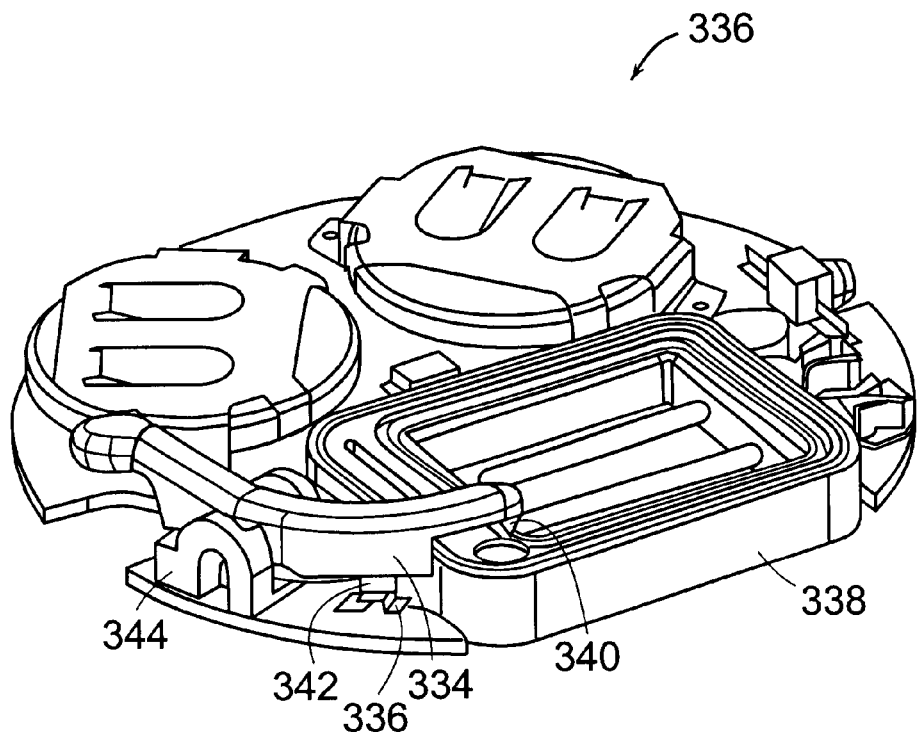
FIGS. 41A and 41B illustrates a preferred embodiment of a drug delivery device including an activation lever in accordance with the present invention.
Figure 41B:
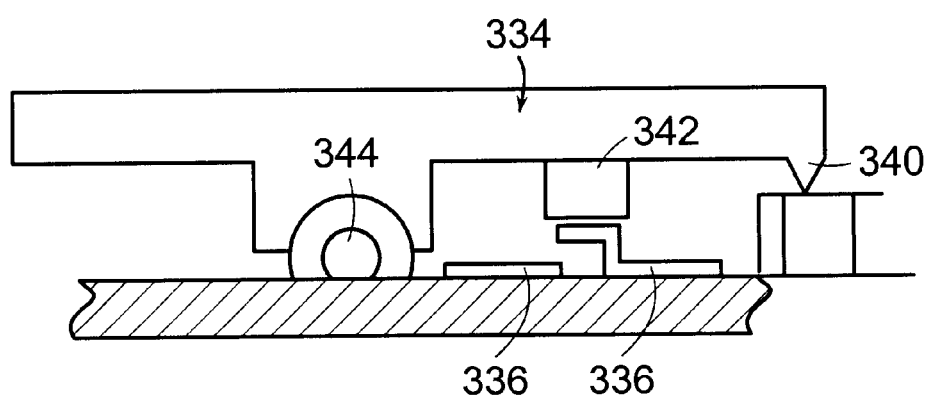

In another embodiment, the drug delivery device 336 can include an activation lever 334, as shown in FIGS. 41A and 41B to initiate gas generation in the expandable chamber which in turn controls the delivery of the drug from the device. The activation lever 334 includes a puncturing device 340 and an electrical contact 342. The drug delivery device 336 includes an electrolytic cell 338 mounted next to the activation lever 334. On the printed circuit board, the electrolytic cell 338 has a foil cover, for example, aluminum foil, to preserve chemical ingredients within the cell 338. Without the foil, the electrolyte water content could evaporate during storage affecting the performance of the device 336. The activation lever 334 can be mounted to the drug delivery device by a pivot 344. Upon depression, the puncturing device 340 of the activation lever 334 can puncture the foil cover of the electrolytic cell 338, thereby allowing the gases generated by the cell operation to escape and to expand the expandable gas chamber and thereby compressing the drug reservoir of the delivery device 336. Also upon depression of the activation lever 334, the electrical contact 342 on the lever 334 engages a contact 346 on the printed circuit board of the device 336 which starts the delivery of the drug. The contact 342 on the lever 334 engages the two contact 346 on the delivery device 336 moving one of the contacts 346 into engagement with the other contact 346 for an indefinite time period.

In a preferred embodiment, the lever 334 can be made from a plastic material. A plastic lever 334 can be economically produced using an injection molding technique, for example. The plastic lever 334 can be secured to the pivot 344 by a snap fit and thereby not require soldering. The plastic lever 334 can be manufactured such that the lever does not bend when forming an electrical contact with the drug delivery device 336 or when puncturing the foil on the electrolytic cell 338.

Another embodiment of the drug delivery system relates to controlling the rate of delivery by parameters such as, for example, residual air volume, base permeability, membrane seal and membrane permeability. In particular, with regards to the residual air volume, an air space can be created within a drug delivery system by providing a cavity for air, for example. Such an air space can be considered as a residual or dead air volume and can have an effect on the drug delivery rate. The larger a residual air volume, the greater the effect on delivery rate. For example, the expansion of the air volume because of a temperature increase can create a bolus effect in the device delivery. Residual air volume can be controlled by design characteristics of the geometry of the inner parts of the device. A high residual air volume within the device can add a delivery period between the activation of the drug delivery system and the actual start of drug delivery.

Figure 42:
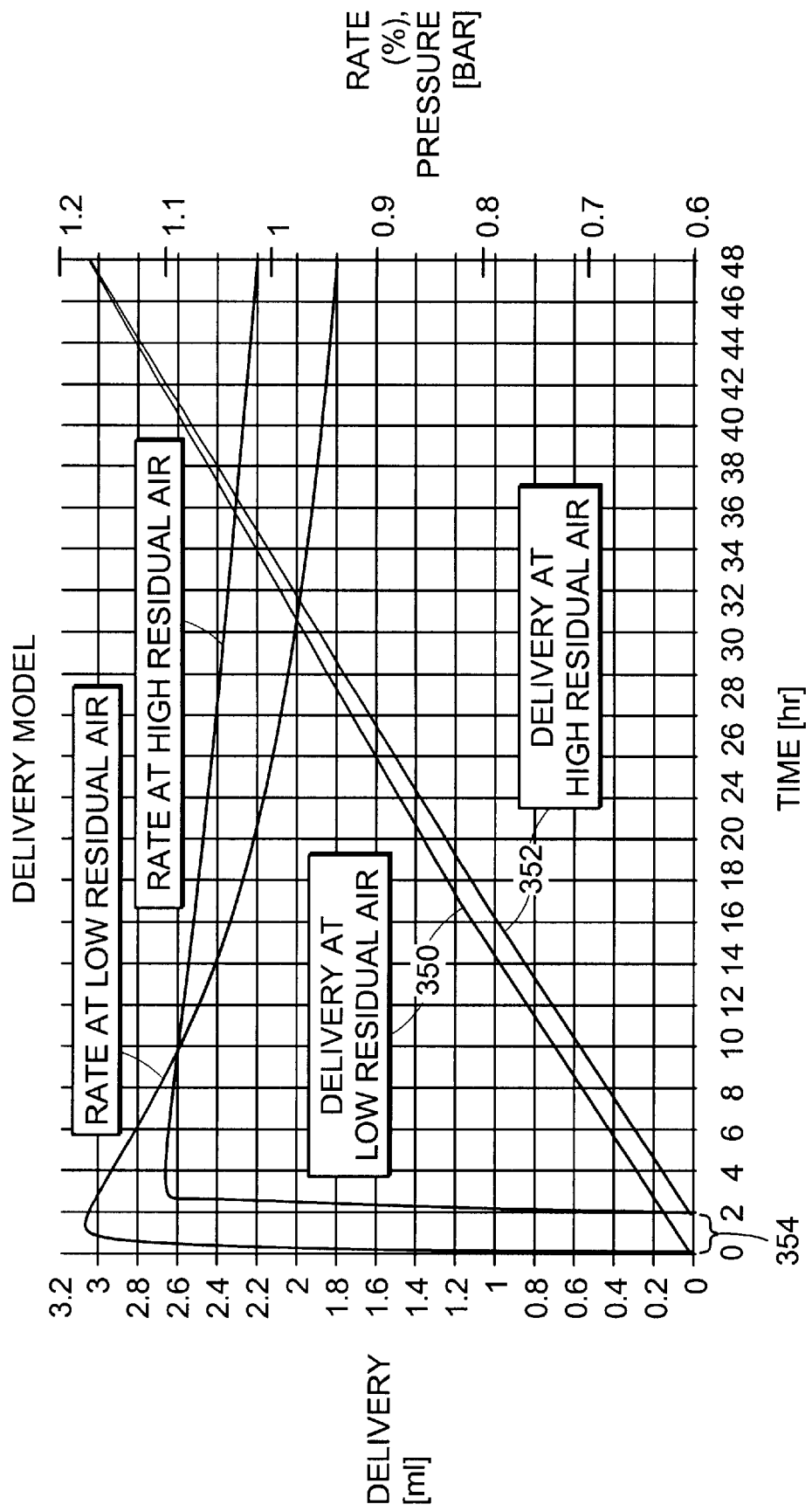
FIG. 42 graphically illustrates the delivery of drugs using a preferred embodiment of the drug delivery device which controls residual air volume in accordance with the present invention.

FIG. 42 illustrates a graph of a delivery 350 of drugs through a drug delivery system under normal or low residual air volume conditions and delivery 352 under high residual air volume conditions. The drugs delivered under high residual air volume conditions are delayed 354 between the activation of the system and the start of drug delivery. By altering the residual air volume within the delivery system by changing the design characteristics, the delay can be reduced or eliminated within the system.

Another embodiment of the drug delivery system relates to controlling the material characteristics of the device components, such as, for example, the permeability of the system which in turn affects the delivery rate of the drug. Permeability can be controlled, for example, by both changing the geometry of the inner components of the delivery system and by changing the materials used to manufacture the system. By lowering the permeability of the delivery system, less gas can diffuse out from the system. With less gas leaving the system, the variance in delivery rate can be lowered or eliminated. By minimizing the permeability to gases of the expandable chamber, a constant delivery rate of the drug can be maintained.

Figure 43:
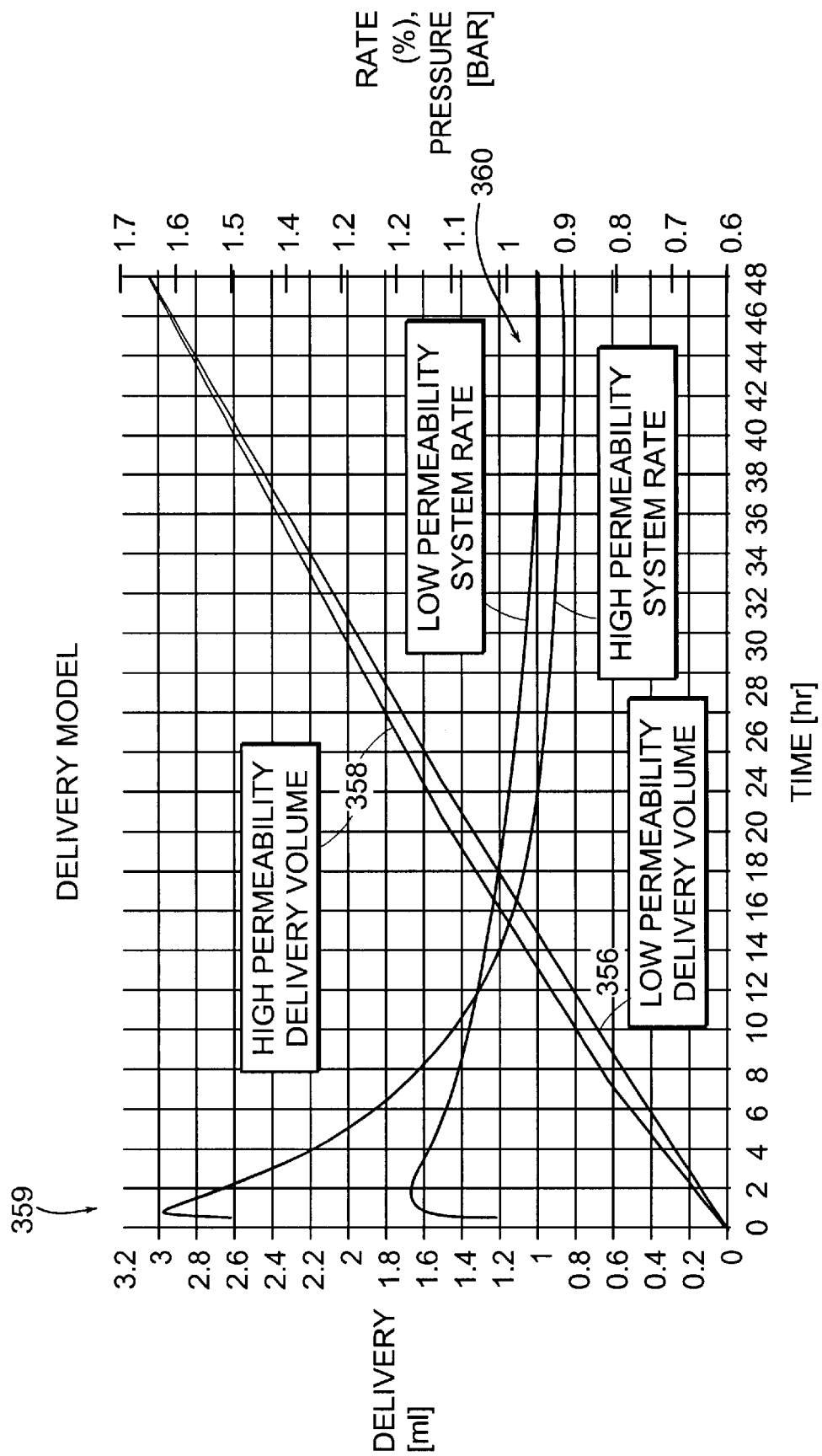
FIG. 43 graphically illustrates the delivery of drugs using a preferred embodiment of the drug delivery device which controls the system permeability in accordance with the present invention.

For example, by using PET plastic, the gas leak rate or permeability is minimized. Alternatively, a highly permeable material can allow a large amount of gas to diffuse out of the drug delivery system which can reduce the drug delivery rate. FIG. 43 illustrates a graph of delivery 356 of drugs for a low permeability system and delivery 358 for high permeability system. As shown, a high permeability yields a higher delivery rate at the onset of delivery 359 and a lower rate of delivery 360 as time goes on, compared to a delivery system having a normal permeability 356.

Packaging of a drug delivery device can be an important factor relating to the practical storage and use of the device at different altitudes and humidities. For example, proper packaging of the device can extend the storage period of the device, without an appreciable affect on the device performed. Proper packaging can also prevent environmental affects, such as, the diffusion of water from the electrolyte that provides for the gas generation from the drug delivery device without additional protection, internal to the device.

In a preferred embodiment, a hermetic packaging for a drug delivery system achieves extended shelf conditions and simplifies the barometric pressure valve and the electrolytic cell of the system.

In a previous embodiment, the drug delivery system was packaged using a blister and a Tyvek lid to maintain sterility and protect the device during a two year shelf life. In this embodiment, the Tyvek lid is gas permeable when exposed to atmospheric conditions, such as, for example, non-controlled pressure and humidity conditions. With this type of packaging, issues can arise as to the maintenance of barometric pressure valve performance and the prevention of drug evaporation from the delivery system. To maintain the desired performance of the barometric pressure valve of the delivery device, the valve has two positions. In one position, the storage position, the valve membrane can move. In another position, the working position, the valve builds pressure against the drug delivery system needle. In order to prevent evaporation of the electrolyte, the electrolytic cell can be fully protected by aluminum foil. Further, the foil seal requires the use of an activation lever. Pinching of this foil around the cell is required for system operation.

In the preferred embodiment, the blister and Tyvek lid packaging can be replaced by a hermetically sealed packaging. By changing the packaging, the issues of valve position and adverse environmental impact, such as, for example, diffusion can be solved without any internal feature protection.

Figure 44A:
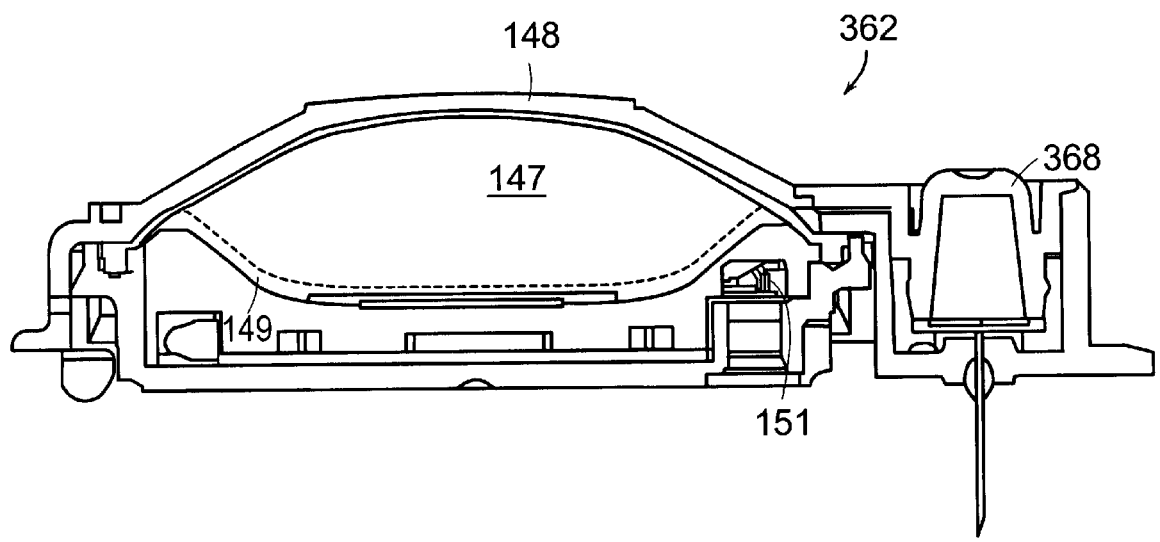
FIG. 44A illustrates a full assembly of the drug delivery device including a stationary barometric pressure valve in accordance with the present invention.

Referring to FIG. 44A, an alternative drug delivery system 362 is shown with a stationary valve 368. The drug delivery system 362 is shown without the displaceable cover 143, such as shown in FIGS. 14 and 15. The internal space of the drug delivery device 362 of FIG. 44A defines an expandable chamber 147 when the diaphragm 148 is in the position shown or a reservoir when the diaphragm is in the position shown in dotted outline at 149. The device 362 has a switch 151 which is engaged by a valve 150, such as seen in FIGS. 14–16, to close the switch to activate the process.

In contrast to the air-filled flow-regulating chamber 35 or 145 of FIGS. 1–3, 14, and 15, in which the chamber 35 moved with the flow of fluid (the drug) both above and below the chamber, the stationary valve 368 does not move. The stationary valve 368 has an airtight chamber 370 sealed by a flow diaphragm 372, similar to the airtight chamber 36 and diaphragm 26 of FIG. 3. However, another distinction is that the flow diaphragm 372 of this embodiment does not have a projection which is received in the inlet associated with the needle such as in some of the previous embodiments.

Figure 44B:
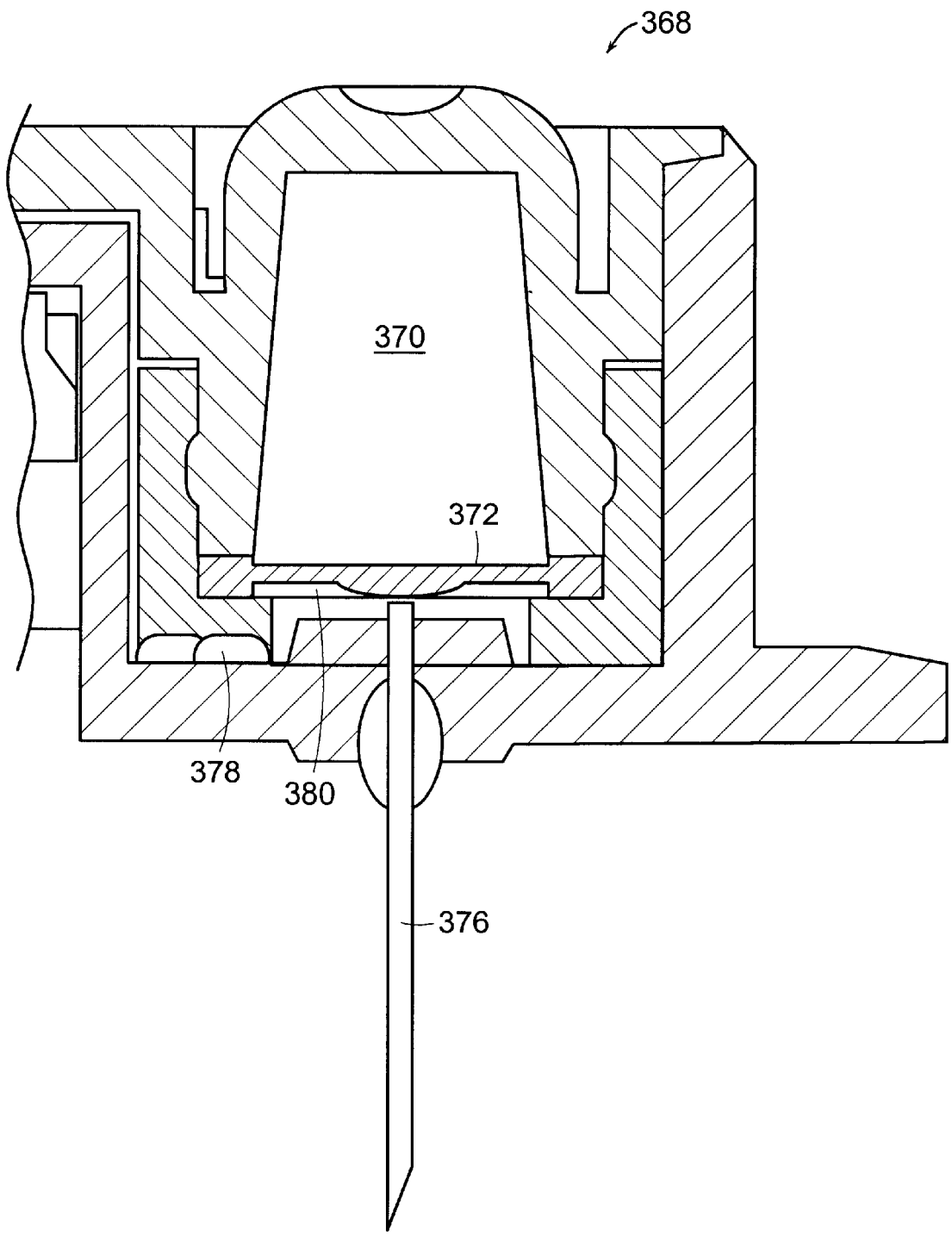
FIG. 44B is an enlarged sectional view of the stationary valve of FIG. 44A.

In contrast, referring to FIG. 44B, the flow diaphragm 372 has a flat circular portion 374 for sealing the top of the needle 376. The drug flows through a port 378 from the reservoir to an annular chamber 380 underlying the flow diaphragm 372. The pressure in the reservoir and the annular chamber 380 is equal to the pressure inside the controlled volume, the airtight chamber 370, therein stressing/flexing the flow diaphragm 372 and opening the entrance to the needle 376. In this embodiment, the valve can become a stationary valve, more accurate and with longer shelf life in extreme conditions. The aluminum protective liner and the pincher mechanism are no longer needed for the cell functioning.

Figure 45:
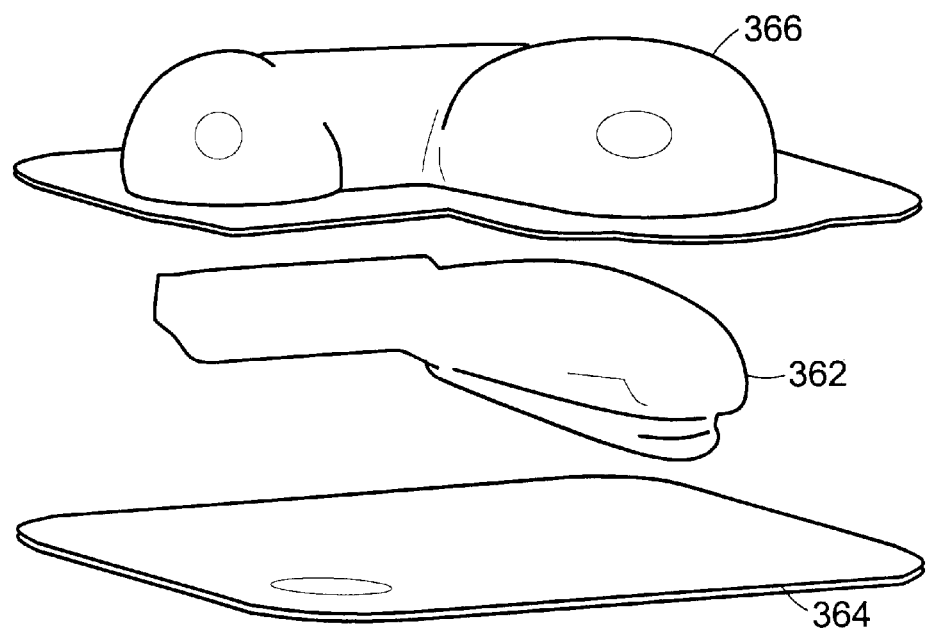
FIG. 45 illustrates a preferred embodiment of the packaging used for the drug delivery device in accordance with the present invention.

The packaging is illustrated in FIG. 45. The drug delivery system 362 can be enclosed between a foil layer 364 and a non-permeable blister 366 to maintain internal pressure despite environmental parameter changes, such as pressure and temperature. The blister is a semi-rigid package with an aluminum cover or low permeability plastic welded at its bottom. The drug delivery device is inserted into the cavity. The blister is made of PET. The cover is made of aluminum foil 38 micron with 2 micron of H.S.C. for the welding. The leak through the materials due to relative pressure at the storage time, designed to effect less than permitted by the drug delivery system specification. The surface area of the package is about 0.034 m² with an average thickness of 0.3 mm, with a permeability factor of about 0.4. Given these dimensions, the pressure in the device is calculated to decrease up to about 3% in two years. The foil layer 364 can be, for example, an aluminum foil.

Over-pressurization of the package during manufacturing can provide a longer shelf life as there is more time for the air to leak before getting to the minimum required pressure, and thus adding shelf life.

In an alternative embodiment for packaging a drug delivery device, a secondary packaging device can be used with a primary gas permeable packaging, such as a blister and Tyvek lid, to extend the storage life of the device. The use of secondary packaging can increase the shelf life of a delivery device without altering the drug delivery rate.

Figure 46:
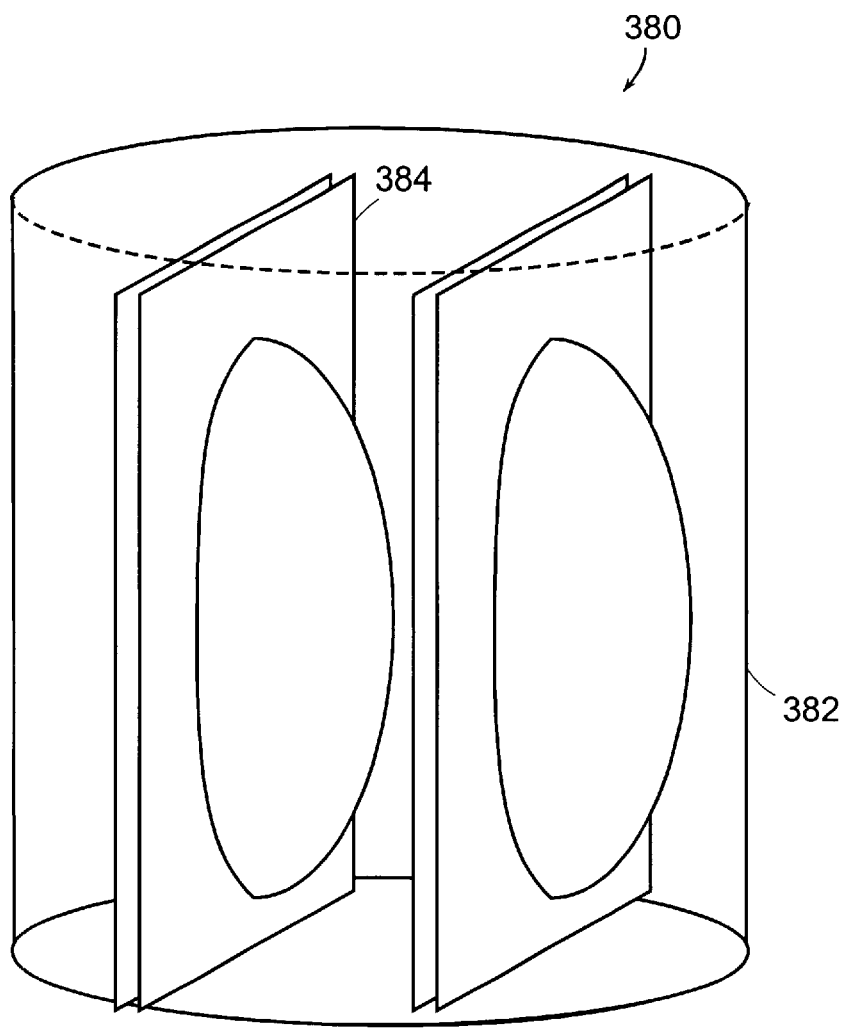
FIG. 46 illustrates an alternate embodiment of packaging used for the drug delivery device in accordance with the present invention.

In a preferred embodiment, the secondary packaging device 380 can be a cylindrical container 382, as shown in FIG. 46. The cylindrical container 382 can be an aluminum or tin can, for example. In an embodiment, the container 382 can hold either four delivery device packages 384, as shown in FIG. 46, or can hold more delivery device packages 384. Prior to storing the drug delivery packages 384 within the container 382, in one embodiment, the drug delivery device can be packaged between a blister and a Tyvek lid and then sterilized.

Figure 47A:
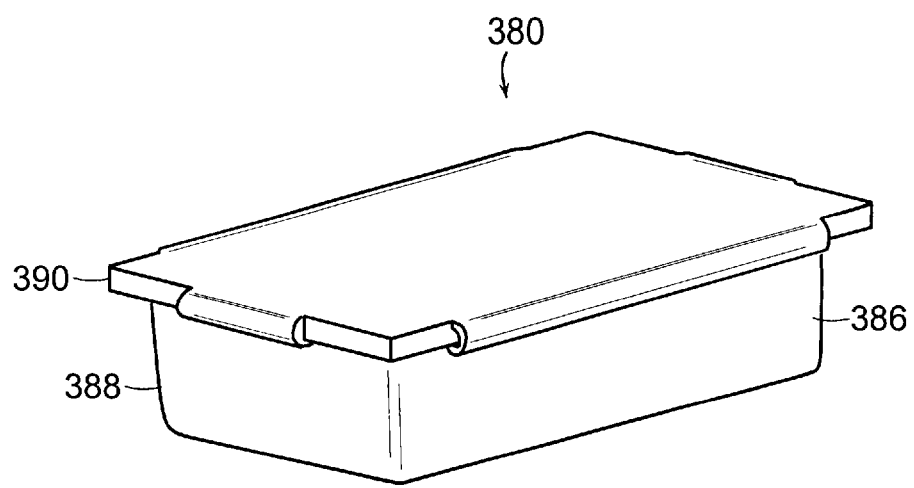
FIGS. 47A–47C illustrate another embodiment of packaging used for the drug delivery device in accordance with the present invention.
Figure 47B:
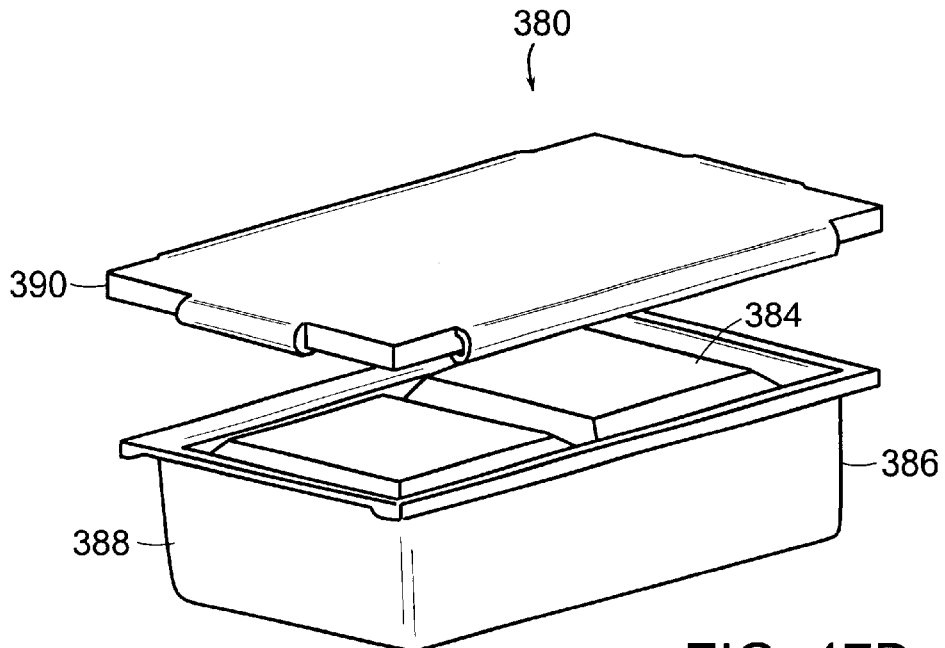
Figure 47C:
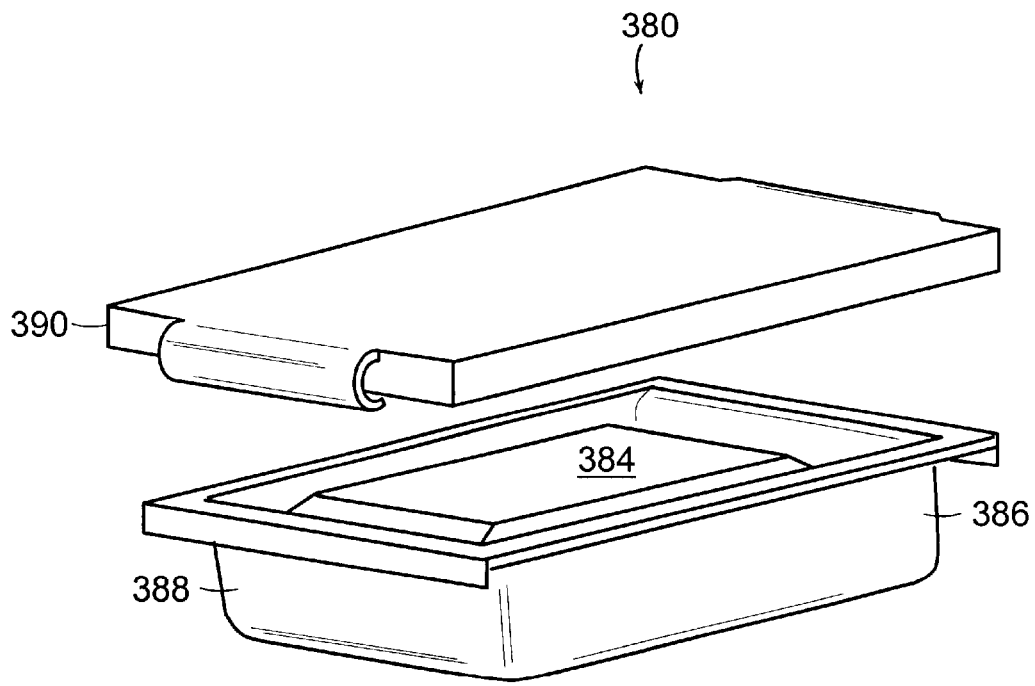

FIGS. 47A–47C illustrate an alternative embodiment for a secondary packaging device 380. In this embodiment, as shown, the secondary packaging device is a rectangular container 386. The rectangular container 386 can have a cover portion 390 and a base portion 388 where the base portion 388 can be used for storage of drug delivery packages 384. FIG. 47A shows an embodiment of the cover portion 390 in a closed position while FIG. 47B shows an embodiment of the cover portion 390 in an open position where the cover 390 can completely disconnect from the base portion 388. In an alternate embodiment, the cover portion 390 can be hingedly attached to the base portion 388.

The rectangular container 386, in one embodiment, can be designed to hold up to four drug delivery devices 384, as shown in FIG. 47B. In another embodiment, the container 386 can be sized to hold a single delivery device 384, as shown in FIG. 47C. A limitation to the use of the container 386 holding four delivery devices 384 can include using the fourth, or last, device within opening the container 386. For a container 386 holding up to four delivery devices, the dimensions of the container can be about 240 mm×148 mm×70 mm. For a container 386 holding a single delivery device, the dimensions of the container can be about 120 mm×110 mm×35 mm. The container 386 can be made from a plastic material. The container 386 can include aluminum foil covered with, for example, polyethylene lamination to close the packaging using heat.

Figure 48:
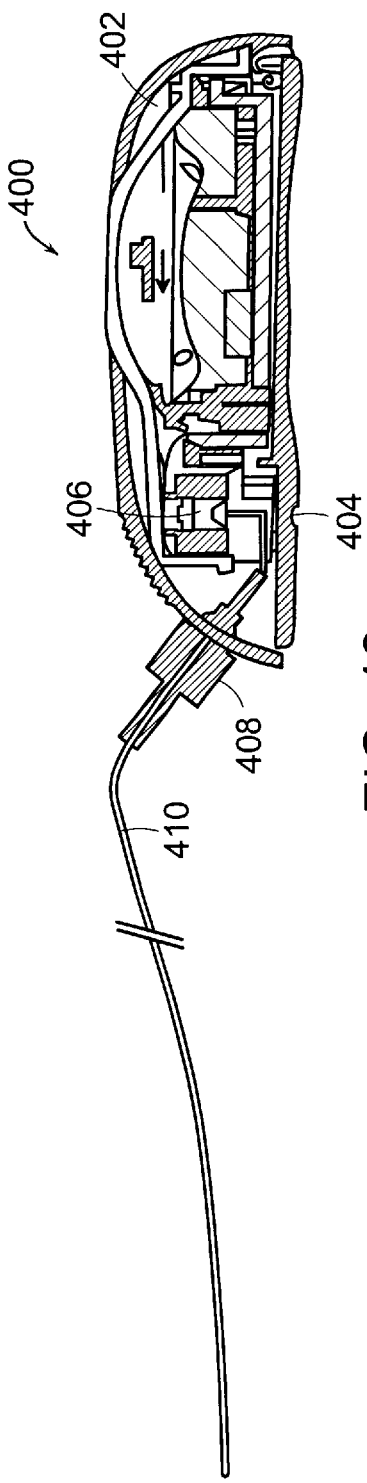
FIG. 48 is a sectional side view of an alternative embodiment of a drug delivery device.

FIG. 48 shows an alternative embodiment of the drug delivery device indicated generally at 400. The delivery system is adapted for epidural, intraterial and intrathecial administration. Instead of a hypodermic needle extending directly from a housing 402, a tube 404 extends from a barometric pressure valve 406 to a location on the housing 402. A catheter 410 is secured by a collet gripper 408 to connect to the tube 404.

Figure 49:
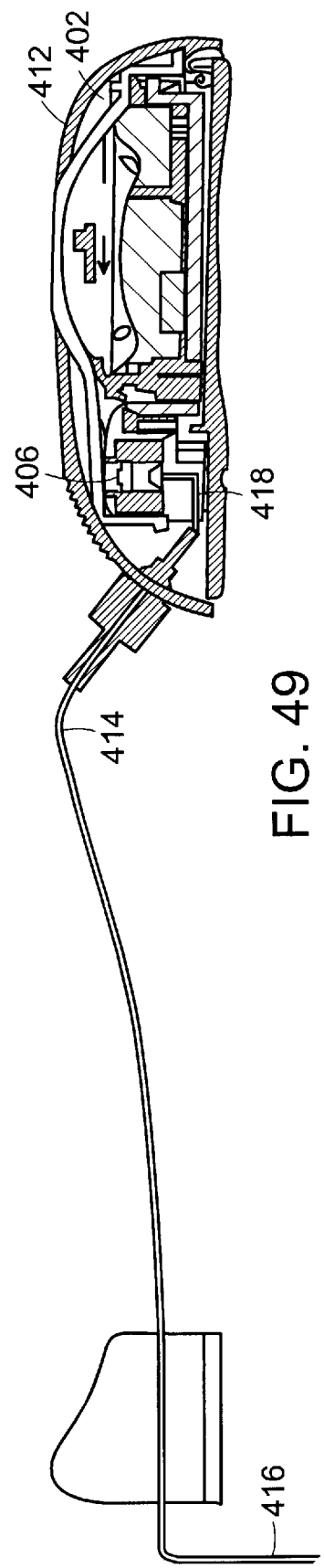
FIG. 49 is a sectional side view of an alternative embodiment of a drug delivery device.

An alternative embodiment drug delivery device 412 of FIG. 49 has a piece of tubing 414 from an epidural needle 416 connected directly to a tube 418 located within the housing 402. The tube 418 extends from the barometric valve 406.

FIG. 50A shows a drug delivery device 420 with a luer 422 for attaching a tubing 424 from an epidural needle 416. A tube 404 extends from the barometric valve 406 to the luer 422.

FIG. 50B shows the drug delivery device 420 with the luer 422. The tubing 424 from the epidural needle 416 attaches to the luer 422. The epidural needle set has a hydrophilic membrane 428 for filtration.

It is further appreciated that the present invention may be used to deliver a number of drugs. The term "drug" used herein includes but is not limited to peptides or proteins, hormones, analgesics, anti-migraine agents, anti-coagulant agents, narcotic antagonists, cleating agents, anti-anginal agents, chemotherapy agents, sedatives, anti-neoplastics, prostaglandins and antidiuretic agents.

Typical drugs include peptides, proteins or hormones such as insulin, calcitonin, calcitonin gene regulating protein, atrial natriuretic protein, colony stimulating factor, betaseron, erythrogpoietin (EPO), interferons such as a,b or g interferon, somatropin, somatotropin, somastostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; anti-emetic agents such as scopolamine, ondansetron, domperidone, metoclopramide, and analogues thereof; cardiovascular agents, anti-hypertensive agents and vasodilators such as diltiazem, clonidine, nifedipine, varapmil, isosorbide-5-mononitrate, organic nitrates, agents used in treatment of heart disorders, and analogues thereof; sedatives such as benzodiazepines, phenothiozines, and analogues thereof; chelating agents such as deferoxamine, and analogues thereof; anti-diuretic agents such as desmopressin, vasopressin, and analogues thereof; anti-anginal agents such as nitroglycerine, and analogues thereof; anti-neoplastics such as fluorouracil, bleomycin, and analogues thereof; prostaglandins and analogues thereof; and chemotherapy agents such as vincristine, and analogues thereof.

While this invention has been particularly shown and described with references to preferred embodiments thereof, it will be understood by those skilled in the art that various changes in form and details may be made therein without departing from the scope of the invention encompassed by the appended claims.

What is claimed is:

1. A drug delivery device comprising:
    a housing having an internal chamber;
    an elastomeric diaphragm within the internal chamber and defining a pair of variable area chambers, an internal drug reservoir chamber and expandable gas chamber;
    an electrolytic cell that generates a gas for expanding the area of the expandable gas chamber and decreasing the area of the internal reservoir, said electrolytic cell having an electrical resistance;
    a drug delivery outlet;
    a fluid path defined between the internal reservoir and the drug delivery outlet;
    a flow regulator, in communication with the fluid path, which is capable of volumetric changes in response to ambient conditions changes; and
    a means for maintaining a specific flow rate of drug delivery even though said electrical resistance may vary.

2. The drug delivery device of claim 1 wherein the means for maintaining a specific flow rate comprises an electrical circuit having a voltage source and resistive means in electrical communication with said electrolytic cell, said resistive means dropping the majority of the voltage supplied by said voltage source.

3. The drug delivery device of claim 2 wherein said voltage source comprises at least two batteries and said resistive means comprises at least two resistors in series.

4. The drug delivery device of claim 1 wherein said electrolytic cell is covered by a foil cover.

5. The drug delivery device of claim 4 further comprising an activation mechanism having a puncturing device for puncturing the foil cover of said electrolytic cell and an electrical contact.

6. A drug delivery device comprising:
    a housing having an internal reservoir and an expandable chamber disposed relative to the reservoir;
    a drug delivery needle extending from the housing for penetration of the skin of a subject, the needle having an outlet for drug delivery; and
    a fluid path defined between the delivery needle outlet and the reservoir,
    an electrolytic cell for generating a gas for expanding the area of the expandable chamber;
    an electrical circuit having a voltage source and resistive means in electrical communication with said electrolytic cell, said resistive means dropping the majority of the voltage supplied by said voltage source.

7. The drug delivery device of claim 6 further comprising a flow regulating chamber, in communication with the fluid path, which is capable of volumetric changes in response to ambient condition changes.

8. The device according to claim 6, wherein the flow regulating chamber is associated with a blocking member which moves within the fluid path upon expansion of the flow regulating chamber so as to restrict the flow of drug.

9. The device according to claim 8, wherein the blocking member comprises a formation provided on a displaceable member which at least partially bounds the flow regulating chamber, the formation being disposed adjacent to an inlet of a conduit forming part of the fluid path, such that restriction of the fluid path occurs when the blocking member is moved into the inlet of the conduit.

10. The device according to claim 8, wherein the blocking member is adapted to cut off the fluid path completely with a predetermined degree of expansion of the flow regulating chamber.

11. A method of controlling the rate of drug delivery comprising the steps of:
    providing a drug delivery device having a housing having an internal chamber and an elastomeric diaphragm within the internal chamber and defining a pair of variable area chambers, an internal drug reservoir chamber and expandable gas chamber;
    expanding the area of the expandable gas chamber and decreasing the area of the internal area by generating a gas in an electrolytic cell controlled by an electrical circuit that uses a resistive means to drop most of the voltage from a voltage source that is in electrical communication with the electrolytic cell; and
    altering the flow which is in communication with the fluid path between the internal reservoir and a drug delivery outlet in response to ambient condition changes.

* * * * *